(12) United States Patent
Bodor et al.

(10) Patent No.: US 6,440,933 B1
(45) Date of Patent: Aug. 27, 2002

(54) COMPOUNDS AND METHOD FOR THE PREVENTION AND TREATMENT OF DIABETIC RETINOPATHY

(75) Inventors: Nicholas Stephen Bodor, Gainesville; Maria Bartolomeo Grant, Archer, both of FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 09/144,991

(22) Filed: Sep. 1, 1998

Related U.S. Application Data

(60) Provisional application No. 60/058,423, filed on Sep. 10, 1997.

(51) Int. Cl.[7] ................ A61K 38/08; A61K 38/12; C07K 5/12
(52) U.S. Cl. ................ 514/11; 514/2; 514/9; 514/15; 514/16; 514/17; 530/300; 530/317; 530/327; 530/328; 530/345; 546/134; 546/288; 546/290; 546/314
(58) Field of Search ............ 514/2, 9, 11, 15–17; 530/345, 300, 317, 327, 328; 546/134, 288, 314, 290

(56) References Cited

U.S. PATENT DOCUMENTS

| | | | |
|---|---|---|---|
| 3,869,548 A | * | 3/1975 | Dabis ........................ 424/94 |
| 3,929,813 A | | 12/1975 | Higuchi et al. ........ 260/296 M |
| 3,962,447 A | | 6/1976 | Higuchi et al. .............. 424/263 |
| 4,530,920 A | | 7/1985 | Nestor et al. .................. 514/15 |
| 4,540,564 A | | 9/1985 | Bodor .......................... 424/9 |
| 4,619,915 A | | 10/1986 | Ives ............................ 514/17 |
| 4,888,427 A | | 12/1989 | Bodor ........................ 546/316 |
| 4,983,586 A | | 1/1991 | Bodor ........................ 514/58 |
| 5,024,998 A | | 6/1991 | Bodor ........................ 514/58 |
| 5,624,894 A | | 4/1997 | Bodor ........................ 514/2 |
| 5,763,200 A | * | 6/1998 | Dunmore et al. .......... 435/7.21 |

FOREIGN PATENT DOCUMENTS

| | | |
|---|---|---|
| EP | 0327766 | 8/1989 |
| EP | 0335545 | 10/1989 |
| EP | 0174342 | 12/1989 |
| WO | 94/06450 | 3/1994 |

OTHER PUBLICATIONS

Bodor, *S.T.P. Pharma Sci.*, "Brain targeting of drugs and neuropeptides by retrometabolic design approaches", 7(1), pp. 43–52 (1997).

* cited by examiner

*Primary Examiner*—Bennett Celsa
(74) *Attorney, Agent, or Firm*—Burns, Doane, Swecker & Mathis, L.L.P.

(57) ABSTRACT

The invention provides peptide derivatives designed to deliver peptides having growth factor inhibitory activity, especially somatostatin analogs, to the retina by sequential metabolism. The peptide derivatives, which comprise a dihydropyridine⇌pyridinium salt-type redox targetor moiety, a bulky lipophilic function and an amino acid/dipeptide/tripeptide spacer, are used in the prevention and treatment of diabetic retinopathy.

19 Claims, No Drawings

COMPOUNDS AND METHOD FOR THE PREVENTION AND TREATMENT OF DIABETIC RETINOPATHY

CROSS-REFERENCE TO RELATED APPLICATION

This application claims the priority of U.S. Provisional Patent Application No. 60/058,423, filed Sep. 10, 1997, incorporated by reference herein in its entirety and relied upon.

FIELD OF THE INVENTION

The invention relates to peptide derivatives designed to deliver peptides having growth factor inhibitory activity into the retina by sequential metabolism. These peptide derivatives, which comprise a dihydropyridine⇌pyridinium salt-type redox targetor moiety, a bulky lipophilic function and an amino acid/dipeptide/tripeptide spacer, are of use in the prevention and treatment of diabetic retinopathy.

BACKGROUND OF THE INVENTION

The leading cause of blindness in adults between the ages of 20 and 74 years is diabetic retinopathy (DR). Seven million people in the United States have diabetes. Diabetic retinopathy will affect the vast majority during their lifetime, with 8,000 to 40,000 of these people becoming blind each year. While management of diabetic retinopathy has improved as a result of landmark clinical trials, risk of complications, such as loss of visual acuity, loss of night vision and loss of peripheral vision, remains significant and treatment sometimes fails. Currently, laser photocoagulation is the most effective form of therapy for advanced disease.

Diabetic retinopathy is characterized by aberrant neovascularization of the retinal vasculature with edema and breakdown in the blood-retinal barrier (BRB) that leads to hemorrhage, tissue damage and retinal scarring. Unfortunately, current treatment options are inadequate and the disease is often progressive even with successful glucose control. An increasing body of evidence indicates that growth factor inhibitors offer the potential to treat a probable cause of diabetic retinopathy by blocking key mediating steps in disease progression.

A. Diabetic Retinopathy and Growth Hormone Inhibitors

Diabetic retinopathy is recognized as a retinal vascular disorder that includes: (i) excess capillary permeability, (ii) vascular closure, and (iii) proliferation of new vessels. The disease is characterized by a loss of retinal capillary pericytes, thickening of the basement membrane, microaneurysms, dot-blot hemorrhages, and hard exudates. The more severe form of the disease is proliferative retinopathy with extensive neovascularization, vessel intrusion into the vitreous, bleeding and scarring around new vessels that leads to severe vision impairment. However, the mechanisms of disease progression remain incompletely understood.

A half century ago, Michaelson postulated that humoral factors stimulated neovascularization in response to anoxia in his studies of retinal disease and an increasing body of evidence indicates growth factors play a pivotal role in progression of diabetic retinopathy.

Evidence linking increased growth hormone (GH) and diabetic retinopathy is substantial. An important role for growth hormone in diabetic retinopathy was indicated 40 years ago when Poulsen described DR regression in a post-partum woman with spontaneous pituitary infarction and proposed hypophysectomy to treat the disease. Controlled clinical trials have shown pituitary ablation could improve diabetic retinopathy and therapeutic success was correlated with the magnitude of growth hormone decrease. Additional support for the growth hormone hypothesis includes: (i) the observation that retinopathy accelerates during puberty when tissue sensitivity to GH is increased; (ii) diabetic patients with hemochromatosis and infiltrative destruction of the pituitary have little eye disease; and (iii) GH-deficient dwarfs with diabetes have no evidence of either macro or microvascular disease. Even diabetics with adequate glucose control show excess GH profiles and diabetic retinopathy is correlated with the magnitude of growth hormone hypersecretion.

Recognition that insulin-like growth factor 1 (IGF-1) mediates most of the anabolic effects of growth hormone has implicated IGF-1 in diabetic vascular complications. Several clinical studies support a role for IGF-1 in development of retinal neovascularization. Merimee and colleagues found increased serum IGF-1 levels from patients with rapidly accelerating diabetic retinopathy. A subsequent prospective study showed that patients had elevated IGF-1 serum levels at the time new retinal vessels first appeared compared to their serum IGF-1 levels three months before the onset of retinal neovascularization. In a large population-based study of 928 diabetic patients, higher levels of IGF-1 were correlated with an increased frequency of proliferative retinopathy.

However, other studies have shown that circulating IGF-1 levels are inappropriately low in most insulin dependent diabetes mellitus (IDDM) patients given their higher-than-normal growth hormone levels. The major source of circulating IGF-1 is the liver, where GH in the presence of insulin triggers IGF-1 gene transcription. IDDM patients have a lower IGF-1 response to exogenous GH, indicating a form of growth hormone resistance. An explanation for clinical studies that showed low IGF-1 patterns in IDDM but high IGF-1 in severe diabetic retinopathy may involve portal insulin levels in IDDM patients. Sönksen et al. recently suggested that the lower portal insulin in IDDM subjects (compared to levels seen by the liver during pancreatic insulin secretion) is responsible for decreased circulating IGF-1 in response to GH stimulation. Thus, endocrine conditions in insulin dependent diabetes mellitus are ideal for excess IGF-1 formation in local tissues, since high circulating levels of GH and insulin (an obligatory consequence of insulin injections in IDDM patients and insulin resistance in NIDDM patients) are available to stimulate IGF-1 local production in peripheral tissues, including the retina. The dynamics between endocrine serum IGF-1 and paracrine tissue IGF-1 production in IDDM subjects is not understood.

Yet other recent studies by Grant support paracrine/autocrine regulation of IGF-1 in diabetic retinopathy. Vitreous levels of IGF-1 better reflect the local levels of growth factors seen in retinal tissue and were measured in 23 diabetic patients with proliferative diabetic retinopathy and compared with age-matched control values. A 3-fold increase was observed in the DR samples compared with controls. IGF-1 secretion was augmented by basic fibroblast growth factor (b-FGF) in cultured human retinal endothelial cells, supporting a paracrine role. Other investigators have shown that IGF-1 receptors increase in retina from diabetic rats that are a model for IDDM.

IGF-1 appears to mediate retinal neovascularization. New vessel formation starts with basement membrane degradation followed by endothelial cell migration and proliferation. IGF-1 stimulates the release of tissue-type plasminogen activator (t-PA) from retinal endothelial cells derived from diabetic patients, but not from retinal endothelial cells derived from nondiabetic individuals. t-PA converts plasminogen to plasmin which can lyse thrombus as well as degrade most of the components of the extracellular matrix. Diabetic endothelial cells have a different response to growth factors. IGF-1 increases the expression of mRNA and protein for type IV collagenase in these same cells and acts synergistically with b-FGF on expression of both t-PA and type IV collagenase that are required for basement membrane degradation. IGF-1 receptors are present on retinal microvascular cells and these cells respond to IGF-1 with a five-fold increase in DNA synthesis. IGF-1 significantly promotes chemotaxis (migration) of human and bovine retinal endothelial cells and fetal bovine aorta endothelial cells in a dose-dependent manner. Thus, IGF-1 seems to act in concert with other growth factors in diabetic retinopathy.

Several studies indicate a role for b-FGF, endothelial growth factor (EGF) and transforming growth factor-α (TGF-α) in neovascularization. The precise functions of each of these factors in angiogenesis is yet to be elucidated. A common link may be response of the receptors upon binding these growth factors. IGF-1, insulin, b-FGF, platelet derived growth factor (PDGF), and EGF receptors belong to an expanded family of growth factor receptors, each sharing the common feature of a tyrosine kinase domain in the cytoplasmic portion of the molecule. Receptor binding induces autophosphorylation of the β-subunit of the receptor that activates the protein tyrosine kinase (PTK). Autophosphorylation renders PTK constituitively active, even when the growth factor is subsequently removed from the binding site. Consequently, dephosphorylation, and not merely dissociation of the growth factor, is required to terminate PTK activity. Activated PTKs are inactivated by protein tyrosine phosphatases (PTPases) which dephosphorylate the receptor.

The physiological inhibitor of GH and IGF-1 is somatostatin, a tetradecapeptide, found throughout the body, which has the structural formula: [SEQ ID NO.: 1]

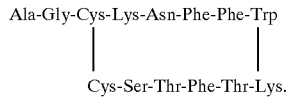

Native somatostatin, however, has limited therapeutic use due to its extremely short half-life and wide range of inhibitory activities. Enzymatically stable somatostatin analogs have been developed with longer half-lives, such as octreotide, which is also known as sandostatin, and which has the structural formula: [SEQ ID NO.: 2]

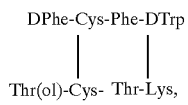

and lanreotide (LNT), which has the structural formula: [SEQ ID NO.: 3]

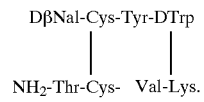

In vitro studies have shown that the somatostatin analogs activate PTPases and therefore function at the biochemical level by promoting inactivation of the autophosphorylated growth factor receptor. Somatostatin and the somatostatin analogs do not cross the blood-brain barrier (BBB), which is consistent with their size, charge and lipid solubility.

Several somatostatin analogs are used for treating neuroendocrine neoplasms and as labeled diagnostic agents to identify tumor tissue. Preclinical studies suggest the agents may be therapeutically useful for treating restenosis following cardiac intervention procedures and chronic graft rejection which may be mediated in part by IGF-1 effects on smooth muscle cells. Clinical tolerance studies show that lanreotide is better tolerated than octreotide and the peptides appear to be equally effective in most preclinical and clinical studies.

The GH inhibitory and antiproliferative effects of somatostatin analogs stimulated several clinical trials in severe proliferative diabetic retinopathy. Initial clinical results were generally disappointing, but the studies were limited to a short dosing duration and doses that were inadequate to suppress GH or IGF-1 levels. More promising results were reported with lanreotide administered via continuous infusion pump for 4 weeks. The study enrolled 17 diabetic retinopathy patients with "low risk" proliferative disease and 8 of 11 subjects completed the lanreotide dosing schedule. Disease progression halted in 8 of 8 patients during lanreotide treatment (and disease regressed in 2 patients), while disease progressed in half the 6 control subjects. Retinal function improved during several months of continuous infusion with octreotide in an uncontrolled clinical trial with 4 patients.

Several factors suggest to the present inventors that drug efficacy could be improved by enhanced delivery of these peptides to the retina: (i) somatostatin receptors are present in retinal tissue that bind octreotide; (ii) octreotide and lanreotide do not cross the BBB; (iii) the inner retinal layer is protected by the BRB, the blood-retinal barrier; and (iv) the BRB is compromised in severe proliferative diabetic retinopathy where somatostatin analogs have shown efficacy.

One of the present inventors (Grant) has used octreotide in six patients (1987–1994) with severe proliferative diabetic retinopathy who previously received maximal pan-retinal photocoagulation, but still had persistent areas of neovascularization of the disk (NVD) and elsewhere (NVE). All six patients received octreotide in doses ranging from 25 to 100 µg three times a day. None of the six patients showed disease progression during their treatment period with octreotide and four patients had regression of their NVD. Whether this represented regression due to octreotide, a delayed response to pan-retinal photocoagulation, or spontaneous regression, is not known. Two of these patients have now been followed for more than 5 years. They continue to do well on octreotide.

A seventh diabetic retinopathy patient had severe bilateral neovascular glaucoma requiring treatment with bilateral Molteno implants in addition to retinal neovascularization. This patient's iris neovascularization regressed completely with the initiation of octreotide, but the posterior pole neovascularization was not affected. The drug was stopped because of gastrointestinal side effects and the iris vessels reappeared. The drug was restarted and there was complete regression of the iris neovascularization. Because the iris has no barrier which is equivalent to the BRB, these results support the hypothesis that somatostatin analogs can be effective in halting neovascularization when they reach their target site.

All seven study patients enjoyed an improved sense of well-being, reductions in their $HgA_{1c}$, and improved visual acuity while on treatment with octreotide.

These encouraging clinical results led to a pilot study by Grant, begun in 1991, to establish whether octreotide can prevent the progression of diabetic retinopathy from either non-proliferative diabetic retinopathy or "low risk" proliferative diabetic retinopathy to "high risk" proliferative diabetic retinopathy. Previous studies have demonstrated that continuous infusion of somatostatin analogs has resulted in greater suppression of GH than intermittent injections. The current clinical study was designed to extend the study duration previously examined by McCombie and coworkers (one year rather than 8 weeks and continuous octreotide infusion with doses up to 5000 µg/day). The results to date are summarized below.

Of the four patients receiving octreotide, no patient showed clear clinical or angiographic improvement. Laser therapy was initiated in all four patients (in at least one eye) when diabetic retinopathy progressed to high risk characteristics as defined by the Diabetic Retinopathy Study recommendations. Suppression of GH and IGF-1 levels into the hypopituitary range was not achieved in any patient. While this inability to induce a "medical hypophysectomy" probably indicates that insufficient octreotide doses were used, a more important factor is whether adequate drug was delivered to retinal tissue.

In the control group (n=5), all patients showed disease progression to the point of requiring laser therapy in both eyes. Results suggest some positive somatostatin analog effects occurred; however, differences between the two groups in measured outcomes are not statistically significant. All four octreotide-treated subjects have shown normalized $HgA_{1c}$ within the first 6 months of therapy, which could not be achieved in the control group. In addition, the patients receiving octreotide had a statistically significant improvement in visual acuity that could be attributable to an improved blood glucose control.

Studies conducted on rapidly proliferating human retinal endothelial cells (HREC) that were stimulated with IGF-1 and b-FGF in vitro have demonstrated direct inhibitory effects of somatostatin analogs in these cells. Octreotide results in a dose-dependent inhibition in [$^3$H] thymidine incorporation measured in both IGF-1 and b-FGF stimulated HREC. This effect of octreotide was examined using HREC derived from diabetic and nondiabetic donors. Growth factors (IGF-1 and b-FGF) were found to stimulate HREC proliferation. Octreotide had minimal effect on cell proliferation in cells grown in control medium. Octreotide significantly decreased the proliferation of HREC in the IGF-1 stimulated cultures and this inhibitory effect was doubled to 40–45% in the b-FGF stimulated cultures. In summary, these in vitro studies support the presence of somatostatin receptors in human retinal tissue and demonstrate a direct inhibition by octreotide on both cell proliferation and DNA synthesis.

In view of the foregoing, it is apparent that a serious need exists for a means of delivering therapeutic concentrations of peptides having growth factor inhibitory activity to the retina in a site-specific and sustained manner for the prevention and treatment of diabetic retinopathy.

B. Blood Retinal Barrier (BRB) and Blood Brain Barrier (BBB) Functions

Several similarities exist between the BRB and the BBB. Zona occludens or tight junctions are the predominant structural feature of non-fenestrated endothelial cells in capillary beds from both brain and retina areas that exclude dye markers injected in the systemic circulation. In contrast, fenestrated capillary endothelium are found in brain and eye areas that permit dye penetration. Pericytes also contribute to barrier function for both the BRB and BBB. However, the simple lipid bilayer model is often used to explain barrier function since this model is consistent with the correlation between the octanol/water partition coefficients and brain uptake measured for many drugs.

The barrier function is not absolute since compounds do enter parenchymal tissue. Transcytosis occurs in both brain and retinal endothelial cells via carrier transport. Paracellular permeation and vesicular transport appear to play little if any role in barrier penetration. These similarities have been used to design an in vivo model to test carrier-mediated brain delivery of conjugated nerve growth factor with septal tissue transplants into the anterior eye chamber.

There is also evidence for functional differences between the BRB and BBB. First, there is clear evidence that the BRB is compromised in diabetes, but no evidence that the BBB is comparably damaged. Second, the few available transport and uptake studies of the BRB analogous to those developed to study the BBB suggest differences. Two research groups have shown a higher permeability surface area product for sucrose in the retina than the brain while another group found no difference. A recent study in normal rats concluded that the BRB is approximately 4 times as permeable to a labeled amino acid compared to the BBB. The investigators concluded that the more numerous pericytes may play an increased protective function for the retina. Pericytes decrease relatively early in diabetes. Third, systemically administered drugs are more effective in reaching retinal tissue than the CNS. An example is the case report for an AIDS patient treated for cytomegalovirus (CMV) retinitis and encephalitis with ganciclovir. Despite successful treatment of CMV retinitis verified at autopsy, there was widespread CMV-encephalitis. Finally, some histocytochemical differences in the vascular beds indicate functional differences between the BBB and BRB, as shown in the following table:

| GENERAL FEATURE COMPARISON OF MICROVESSELS IN RAT EYE AND BRAIN | | | | |
|---|---|---|---|---|
| | Brain | Retina | Iris | Ciliary body |
| Luminal diameter ($\mu$m) | 4.4 ± 0.11 | 4.8 ± 0.23 | 6.7 ± 0.28 | 7.4 ± 0.24 |
| Wall thickness ($\mu$m) | 0.33 ± 0.02 | 0.39 ± 0.02 | 0.46 ± 0.02 | 0.45 ± 0.02 |
| Cytoplasmic area/profile ($\mu m^2$) | 4.2 ± 0.34 | 7.0 ± 0.87 | 11.4 ± 0.65 | 11.1 ± 0.08 |
| Fenestrations (#/100 $\mu$m perimeter) | 0 | 0 | 0 | 31.6 ± 3.92 |
| Junctions with wide clefts (%) | 0 | 0 | 11.8 | 18 |
| Pericyte area/profile ($\mu m^2$) | 1.4 ± 0.21 | 3.8 ± 0.54 | not measured | not measured |

Mean±SEM data after Stewart, P. A. and Tuor, U. I. (1994) *J. Comp. Neurol.* 340, 566–576.

All of these functional differences suggest that drug delivery could be designed to preferentially enhance BRB penetration without significant BBB interaction.

C. Redox-Based Chemical Delivery System (CDS) for Brain Targeting of Centrally Acting Drugs Various strategies have been developed for directing centrally acting drugs, including in some cases peptides, into the brain. A dihydropyridine⇌pyridinium redox system has recently been successfully applied to delivery to the brain of a number of drugs. Generally speaking, according to this system, a dihydropyridine derivative of a biologically active compound is synthesized, which derivative can enter the CNS through the blood-brain barrier following its systemic administration. Subsequent oxidation of the dihydropyridine species to the corresponding pyridinium salt leads to delivery of the drug to the brain.

Five main approaches have been used thus far for delivering drugs to the brain using a redox system. The first approach involves derivation of selected drugs which contain a pyridinium nucleus as an integral structural component. This approach was first applied to delivering to the brain N-methylpyridinium-2-carbaldoxime chloride (2-PAM), the active nucleus of which constitutes a quaternary pyridinium salt, by way of the dihydropyridine latentiated prodrug form thereof. Thus, a hydrophilic compound (2-PAM) was made lipoidal (i.e. lipophilic) by making its dihydropyridine form (Pro-2-PAM) to enable its penetration through lipoidal barriers. This simple prodrug approach allowed the compound to get into the brain as well as other organs, but this manipulation did not and could not result in any brain specificity. On the contrary, such approach was delimited to relatively small molecule quaternary pyridinium ring-containing drug species and did not provide the overall ideal result of brain-specific, sustained release of the desired drug, with concomitant rapid elimination from the general circulation, enhanced drug efficacy and decreased toxicity. No "trapping" in the brain of the 2-PAM formed in situ resulted, and obviously no brain-specific, sustained delivery occurred as any consequence thereof: the 2-PAM was eliminated as fast from the brain as it was from the general circulation and other organs. Compare U.S. Pat. Nos. 3,929,813 and 3,962,447; Bodor et al, *J. Pharm. Sci.*, 67, No. 5, 685 (1978). See also Bodor, "Novel Approaches for the Design of Membrane Transport Properties of Drugs", in *Design of Biopharmaceutical Properties Through Prodrugs and Analogs,* Roche, E. B. (ed.), APhA Academy of Pharmaceutical Sciences, Washington, D.C., 98–135 (1976). Subsequent extension of this first approach to delivering a much larger quaternary salt, berberine, to the brain via its dihydropyridine prodrug form was, however, found to provide site-specific sustained delivery to the brain of that anticancer agent. See Bodor et al, *Science*, Vol. 214, Dec. 18, 1981, pp. 1370–1372. This approach is not applicable to the delivery of peptides, however, since they do not comprise active quaternary pyridinium salts.

The second approach for delivering drugs to the brain using a redox system involves the use of a dihydropyridine/pyridinium carrier chemically linked to a biologically active compound. Bodor et al, *Science*, Vol. 214, Dec. 18, 1981, pp. 1370–1372, outlines a scheme for this specific and sustained delivery of drug species to the brain, as depicted in the following Scheme A:

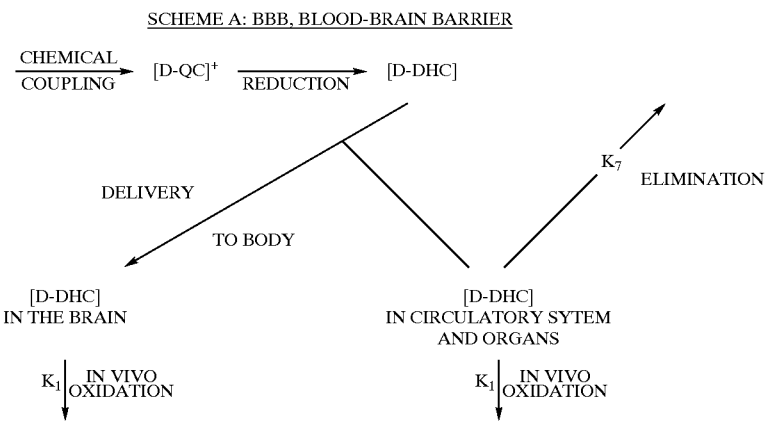

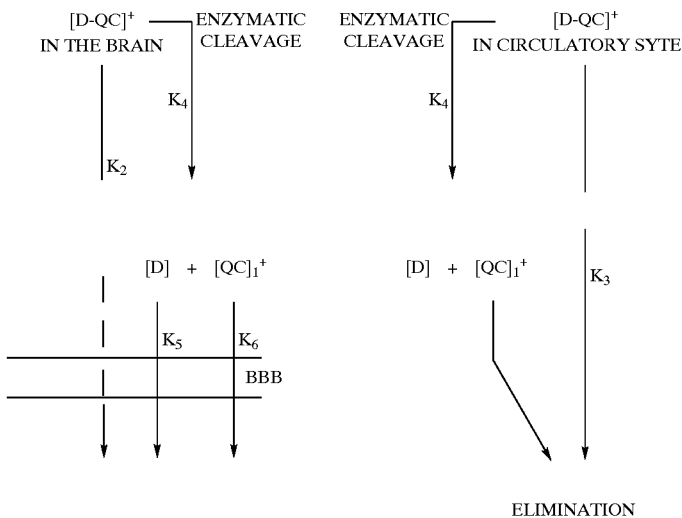

According to the scheme in *Science,* a drug [D] is coupled to a quaternary carrier [QC]$^+$ and the [D-QC]$^+$ which results is then reduced chemically to the lipoidal dihydro form [D-DHC]. After administration of [D-DHC] in vivo, it is rapidly distributed throughout the body, including the brain. The dihydro form [D-DHC] is then in situ oxidized (rate constant, $k_1$) (by the NAD⇌NADH system) to the ideally inactive original [D-QC]$^+$ quaternary salt which, because of its ionic, hydrophilic character, should be rapidly eliminated from the general circulation of the body, while the blood-brain barrier should prevent its elimination from the brain ($K_3 \gg k_2$; $k_3 \gg k_7$). Enzymatic cleavage of the [D-QC]$^+$ that is "locked" in the brain effects a sustained delivery of the drug species [D], followed by its normal elimination ($k_5$), metabolism. A properly selected carrier [QC]$^+$ will also be rapidly eliminated from the brain ($k_6 \gg k_2$). Because of the facile elimination of [D-QC]$^+$ from the general circulation, only minor amounts of drug are released in the body ($k_3 \gg k_4$); [D] will be released primarily in the brain ($k_4 > k_2$). The overall result ideally will be a brain-specific sustained release of the target drug species. Specifically, Bodor et al worked with phenylethylamine as the drug model. That compound was coupled to nicotinic acid, then quaternized to give compounds of the formula

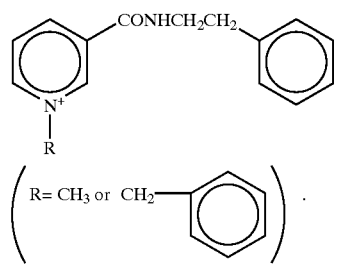

which were subsequently reduced by sodium dithionite to the corresponding compounds of the formula

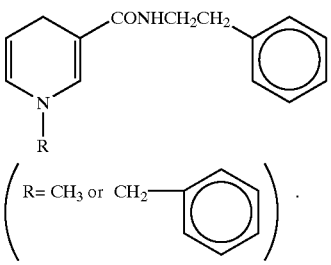

Testing of the N-methyl derivative in vivo supported the criteria set forth in Scheme A. Bodor et al speculated that various types of drugs might possibly be delivered using the depicted or analogous carrier systems and indicated that use of N-methylnicotinic acid esters and amides and their pyridine ring-substituted derivatives was being studied for delivery of amino- or hydroxyl-containing drugs, including small peptides, to the brain. No other possible specific carriers were disclosed. Other reports of this work with the redox carrier system have appeared in *The Friday Evening Post,* Aug. 14, 1981, Health Center Communications, University of Florida, Gainesville, Fla.; *Chemical & Engineering News,* Dec. 21, 1981, pp. 24–25; and *Science News,* Jan. 2, 1982, Vol. 121, No. 1, page 7. Subsequently, the redox carrier system was substantially extended in terms of possible carriers and drugs to be delivered. See International Patent Application No. PCT/US83/00725, filed May 12, 1983 and published Nov. 24, 1983 under International Publication No. WO83/03968. Also see Bodor et al, *Pharmacology and Therapeutics,* Vol. 19, No. 3, pp. 337–386 (1983); and Bodor U.S. Pat. No. 4,540,564, issued Sep. 10, 1985.

The aforementioned Bodor U.S. Pat. No. 4,540,564 specifically contemplates application of the dihydropyridine⇌pyridinium salt carrier system to amino acids and peptides, particularly small peptides having 2 to 20 amino acid units. Among the amino acids and peptides mentioned in the patent are GABA, tyrosine, tryptophan, met$^5$-enkephalin, leu$^5$-enkephalin, LHRH and its analogs and others. Thus, in the carrier system as applied to amino acids and peptides, the free carboxyl function is protected in an effort to prevent premature metabolism, e.g. with an ethyl ester, while the trigonelline-type carrier is linked to the amino acid or peptide through its free amino function. Oxidation of the dihydropyridine carrier moiety in vivo to the ionic pyridinium salt carrier/drug entity prevents elimination thereof from the brain, while elimination from the general circulation is accelerated, and subsequent cleavage of the quaternary carrier/drug species results in sustained delivery of the amino acid or peptide (e.g. tryptophan, GABA, leu$^5$-enkephalin, etc.) in the brain and facile elimination of the carrier moiety. This method is quite useful for delivery of amino acids; in the case of peptides, however, the typical suggested carboxyl protecting groups do not confer sufficient lipophilicity on the peptide molecule. Moreover, this approach does not address the problem of the enzymatic blood-brain barrier or suggest a means of avoiding that problem.

The third approach for delivering drugs to the brain using a redox system provides derivatives of centrally acting amines in which a primary, secondary or tertiary amine function has been replaced with a dihydropyridine/pyridinium salt redox system. These brain-specific analogs of centrally acting amines have been described in International Patent Application No. PCT/US85/00236, filed Feb. 15, 1985 and published Sep. 12, 1985 under International Publication No. WO85/03937. The dihydropyridine analogs are characterized by the structural formula

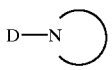

wherein D is the residue of a centrally acting primary, secondary or tertiary amine, and

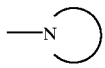

is a radical of the formula

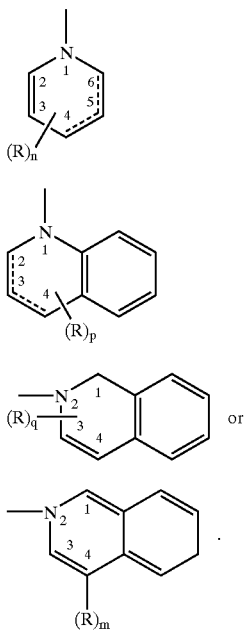

These dihydropyridine analogs act as a delivery system for the corresponding biologically active quaternary compounds in vivo. Due to its lipophilic nature, the dihydropyridine analog will distribute throughout the body and has easy access to the brain through the blood-brain barrier. Oxidation in vivo will then provide the quaternary form, which will be "locked" preferentially in the brain. In contradistinction to the drug-carrier entities described in Bodor U.S. Pat. No. 4,540,564 and related publications, however, there is no readily metabolically cleavable bond between drug and quaternary portions, and the active species delivered is not the original drug from which the dihydro analog was derived, but rather is the quaternary analog itself.

The aforementioned International Publication No. WO85/03937 contemplates application of its analog system to amino acids and small peptides, e.g., the enkephalins, tryptophan, GABA, LHRH analogs and others. In this analog system as applied to amino acids and peptides, the free carboxyl function is thus protected to prevent premature metabolism while the dihydropyridine⇌pyridinium salt type redox system replaces the free amino function in the amino acid or peptide.

As described in International Publication No. WO85/03937, the chemical processes for preparing the redox analog derivatives replace any free amino function in the selected drug with the redox analog system. When these processes are applied to amino acids, they provide a redox amino acid which no longer contains a free amino function for linkage to another amino acid or peptide via a peptide bond (—CONH—). Such an analog amino acid can thus only be used to prepare a peptide having the analog amino acid located at the peptide's N-terminus. This limits use of the redox analog amino acids in peptide synthesis. Moreover, as noted hereinabove, this approach is not designed to ultimately deliver the original peptide to the brain, since there is no cleavable bond between peptide and quaternary portions; rather, the redox portion in this approach becomes an inherent, essentially inseparable part of a new peptide analog. Furthermore, this approach does not address the problem of the enzymatic blood-brain barrier or suggest a means for avoiding the premature degradation caused by the highly active neuropeptide degrading enzymes.

The fourth redox approach is designed to provide redox amino acids which can be used to synthesize peptides having a redox analog system inserted at a variety of locations in the peptide chain, including non-terminal positions, and has been described in Bodor U.S. Pat. No. 4,888,427, issued Dec. 19, 1989. These amino acids contain a redox system appended directly or via an alkylene bridge to the carbon atom adjacent to the carboxyl carbon. The peptides provided by U.S. Pat. No. 4,888,427 have an amino acid fragment of the formula

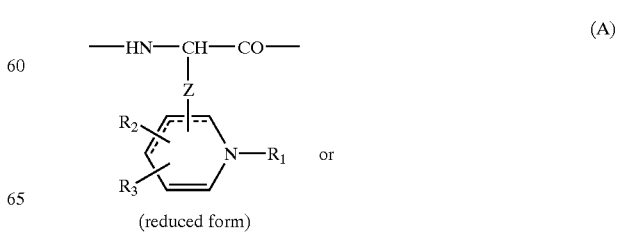

-continued

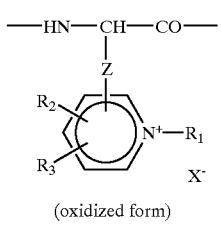

(oxidized form)

(B)

incorporated therein at a non-critical position in the peptide chain, i.e., at a final redox peptide of U.S. Pat. No. 4,888,427 preferably contains a total of 2 final redox peptide of U.S. Pat. No. 4,888,427 preferably contains a total of 2 amino acid fragment of structure (A) or (B) and the possible protection of terminal amino and carboxyl functions, the structure of the redox peptide is identical to that of a known, naturally occurring bioactive peptide or of a known bioactive synthetic peptide (particularly one which is an analog of a naturally occurring bioactive peptide).

It is apparent from the foregoing, that the fourth redox approach, like the third approach discussed above, is not designed to ultimately deliver the original peptide to the brain because there is again no cleavable bond between peptide and quaternary portions. Again, the redox system becomes an integral part of a new peptide analog, not a means for ultimately delivering the original peptide to the brain. Still further, this approach also does not address the problem of the enzymatic blood-brain barrier or suggest a means for avoiding deactivation of the peptide by enzymes before it achieves its therapeutic objective.

The fifth and most recent redox approach provides for brain-enhanced delivery of neuroactive peptides by sequential metabolism. This approach provides a means for "molecular packaging" of peptides which addresses the problems of the physical blood-brain barrier as well as the problems of the enzymatic blood-brain barrier. According to this fifth redox approach, a pharmacologically active peptide is placed in a molecular environment which disguises its peptide nature. This environment provides a biolabile, lipophilic function to penetrate the blood-brain barrier by passive transport; a dihydropyridine-type redox moiety for targeting the peptide to the brain and providing "lock-in" as the pyridinium salt; and an amino acid or di- or tripeptide spacer between redox moiety and peptide designed to enhance the sequential metabolism of the "molecularly packaged" peptide.

Consistent with the foregoing, the fifth redox approach provides, for brain-targeted peptide delivery, "packaged" peptide systems of the formula

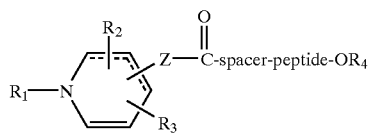

wherein Z is either a direct bond or $C_1$–$C_6$ alkylene and can be attached to the heterocyclic ring via a ring carbon atom or via the ring nitrogen atom; $R_1$ is $C_1$–$C_7$ alkyl, $C_1$–$C_7$ haloalkyl or $C_7$–$C_{12}$ aralkyl when Z is attached to a ring carbon atom; $R_1$ is a direct bond when Z is attached to the ring nitrogen atom; $R_2$ and $R_3$, which can be the same or different, are selected from the group consisting of hydrogen, halo, cyano, $C_1$–$C_7$ alkyl, $C_1$–$C_7$ alkoxy, $C_2$–$C_8$ alkoxycarbonyl, $C_2$–$C_8$ alkanoyloxy, $C_1$–$C_7$ haloalkyl, $C_1$–$C_7$ alkylthio, $C_1$–$C_7$ alkysulfinyl, $C_1$–$C_7$ alkylsulfonyl, —CH=NOR'" wherein R'" is hydrogen or $C_1$–$C_7$ alkyl, and —CONR'R" wherein R' and R", which can be the same or different, are each hydrogen or $C_1$–$C_7$ alkyl; or one of $R_2$ and $R_3$ together with the adjacent ring carbon atom forms a benzene ring fused to the heterocyclic ring, which benzene ring may optionally bear one or two substituents, which can be the same or different, selected from the group consisting of hydroxy, protected hydroxy, halo, cyano, $C_1$–$C_7$ alkyl, $C_1$–$C_7$ alkoxy, $C_2$–$C_8$ alkoxycarbonyl, $C_2$–$C_8$ alkanoyloxy, $C_1$–$C_7$ haloalkyl, $C_1$–$C_7$ alkylthio, $C_1$–$C_7$ alkylsulfinyl, $C_1$–$C_7$ alkylsulfonyl, —CH=NOR'" wherein R'" is hydrogen or $C_1$–$C_7$ alkyl, and —CONR'R" wherein R' and R", which can be the same or different, are each hydrogen or $C_1$–$C_7$ alkyl; the dotted lines indicate that the compound of formula (I) contains a 1,4- or 1,6-dihydropyridine, a 1,4- or 1,2-dihydroquinoline, or a 1,2-dihydroisoquinoline ring system; "spacer" is an L-amino acid unit or a di- or tripeptide consisting of 2 or 3 L-amino acid units, the N-terminal amino acid of said spacer being bonded to the depicted carbonyl carbon via an amide bond; and "peptide" is a pharmacologically active peptide having 2 to 20 amino acid units, the N-terminal amino acid of said peptide being bonded to the C-terminal amino acid of said spacer via a peptide bond, the C-terminal amino acid of said peptide having an esterified carboxyl function —$COOR_4$ wherein $R_4$ is $C_8$–$C_{22}$ alkyl, $C_8$–$C_{22}$ alkenyl, $C_6$–$C_{30}$ polycycloalkyl-$C_pH_{2p}$— wherein p is 0, 1, 2 or 3, or $C_6$–$C_{30}$ polycycloalkenyl-$C_pH_{2p}$— wherein p is defined as above. See, for example, Bodor U.S. Pat. No. 5,624,894, issued Apr. 29, 1997, incorporated by reference herein in its entirety and relied upon.

In specific embodiments of the brain-targeted molecular packaging of the aforementioned U.S. Pat. No. 5,624,894, packaged TRH-type peptides and enkephalin-type peptides are described and shown to deliver pharmacologically significant amounts of the peptides to the brain. As is apparent from the foregoing, both the COOH-terminus and the $NH_2$-terminus of the peptide molecule are modified in such a way as to increase the lipid solubility of the peptide, and also to prevent cleavage by the BBB aminopeptidases. Additionally, the representative 1,4-dihydrotrigonellinate redox targetor (T) exploits the unique architecture of the BBB which allows for the influx of the lipid soluble neutral form, but is not permeable to the positively charged form. The enkephalins are sensitive to cleavage by endopeptidases at the $Gly^3$-$Phe^4$ peptide bond. Cholesteryl, a bulky and lipophilic steroidal moiety (L), provides a representative ester function that increases the lipid solubility and also hinders the C-terminal portion of the peptide from being recognized by peptide-degrading enzymes. This part of the molecule is, however, labile toward esterase or lipase, which permits its removal after delivery. The lipases or esterases expose the peptide unit that can interact with specific receptors, or that may serve as a substrate for various neuropeptide processing and degrading enzymes. A spacer function (S) is also incorporated in order to preserve the integrity of the peptide unit by spatially separating the important segment of the molecule (important in terms of central activity) from the targetor (T). In essence, the peptide unit of this brain delivery system appears as a pertubation on a bulky molecule dominated by the lipophilic steroidal portion and the targetor, which also prevents recognition by the peptidases.

The "packaged" peptide system of U.S. Pat. No. 5,624,894 thus offers a means of deliverying neuropeptides to the brain. There is no suggestion therein, however, that the system could be adapted to the targeting of peptides to tissues of the body other than the brain.

SUMMARY AND OBJECTS OF THE INVENTION

One object of the present invention is to provide a method for the prevention or treatment of diabetic retinopathy.

Another object of the present invention is to provide a means for enhancing the delivery of peptides having growth factor inhibitory activity, particularly somatostatin analogs, into the retina.

Another object of the present invention is to overcome the blood-retina barrier (BRB) and provide sustained delivery of a growth factor inhibitory peptide drug to the retina.

Yet another object of the present invention is to halt, slow or delay the progression of diabetic retinopathy at an early stage before severe neovascularization occurs and to thus prevent visual impairment.

Still another object of the present invention is to adapt the molecular "packaging" of neuroactive peptides for sustained, brain-targeted delivery to overcome the blood-brain barrier to the packaging of peptides having growth factor inhibitory activity such as somatostatin analogs for sustained, retina-targeted delivery to overcome the blood-retinal barrier.

These objects are achieved in whole or in part by the present invention, in which a peptide having growth factor inhibitory activity, particularly a somatostatin analog, is placed in a molecular environment which disguises its peptide nature. This environment provides a lipophilic dihydropyridine⇌pyridinium salt-type redox targetor (T) which functions to first enhance peptide penetration through the BRB and then "locks" the packaged peptide behind the lipophilic BRB via oxidation to the quaternary form. A protective bulky biolabile lipophilic group (L) also facilitates BRB penetration by passive transport and also assists in disguising the peptide nature of the active portion of the molecule from degrading enzymes. An amino acid, dipeptide or tripeptide spacer (S) between redox targetor and peptide further disguises the active portion and modulates the rate of cleavage of the packaged peptide for sustained release of the free active peptide in the retina.

Consistent with the foregoing, the present invention provides "packaged" peptide systems of the formula:

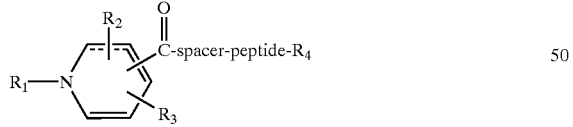

(I)

and the non-toxic pharmaceutically acceptable salts thereof, wherein:

$R_1$ is $C_1$–$C_7$ alkyl, $C_1$–$C_7$ haloalkyl or $C_7$–$C_{12}$ aralkyl;

$R_2$ and $R_3$, which are the same or different, are each selected from the group consisting of hydrogen, halo, cyano, $C_1$–$C_7$ alkyl, $C_1$–$C_7$ alkoxy, $C_2$–$C_8$ alkoxycarbonyl, $C_2$–$C_8$ alkanoyloxy, $C_1$–$C_7$ haloalkyl, $C_1$–$C_7$ alkylthio, $C_1$–$C_7$ alkylsulfinyl, $C_1$–$C_7$ alkylsulfonyl, —CH=NOR''' wherein R''' is hydrogen or $C_1$–$C_7$ alkyl, and —CONR'R'' wherein R' and R'', which are the same or different, are each hydrogen or $C_1$–$C_7$ alkyl;

or one of $R_2$ and $R_3$ together with the adjacent ring carbon atom forms a phenyl ring fused to the six-membered heterocyclic ring, which phenyl ring is unsubstituted or is substituted with one or two substituents, which are the same or different, selected from the group consisting of hydroxy, protected hydroxy, halo, cyano, $C_1$–$C_7$ alkyl, $C_1$–$C_7$ alkoxy, $C_2$–$C_8$ alkoxycarbonyl, $C_2$–$C_8$ alkanoyloxy, $C_1$–$C_7$ haloalkyl, $C_1$–$C_7$ alkylthio, $C_1$–$C_7$ alkylsulfinyl, $C_1$–$C_7$ alkylsulfonyl, —CH=NOR''' wherein R''' is hydrogen or $C_1$–$C_7$ alkyl, and —CONR'R'' wherein R' and R'', which are the same or different, are each hydrogen or $C_1$–$C_7$ alkyl;

the dotted lines represent a double bond in one of the two indicated positions, the depicted ring system being a 1,4- or 1,6-dihydropyridine, a 1,4- or 1,2-dihydroquinoline, or a 1,2-dihydroisoquinoline;

"spacer" is an L-amino acid unit or a di- or tripeptide consisting of 2 or 3 L-amino acid units, the N-terminal amino acid of said spacer being bonded to the depicted carbonyl carbon via an amide bond;.

and "peptide" is a peptide having 2 to 20 amino acid units which has growth factor inhibitory activity, wherein the N-terminal amino acid of said peptide is bonded to the C-terminal amino acid of said spacer via a peptide bond, and wherein the C-terminal amino acid of said peptide:

(a) has a C-terminal carboxyl group —COOH which has been replaced with a —COOR$_4$ group wherein R$_4$ is $C_6$–$C_{30}$ polycycloalkyl-$C_pH_{2p}$— wherein p is 0, 1, 2 or 3, or $C_6$–$C_{30}$ polycycloalkenyl-$C_pH_{2p}$— wherein p is defined as above;

(b) has a C-terminal —CH$_2$OH group which has been replaced with a —CH$_2$OCOR$_4$ group wherein R$_4$ is defined as above;

(c) has a C-terminal —CONH$_2$ group which has been replaced with a —CO-Gly-OR$_4$ group wherein R$_4$ is defined as above, said —CO-Gly-OR$_4$ group regenerating the C-terminal —CONH$_2$ group in vivo;

(d) has a C-terminal —CONH$_2$ group; or (e) has a C-terminal —CH$_2$OH group;

with the provisos that:

(1) when the C-terminal amino acid is as defined in (a), (b) or (c) above and when the peptide has a basic amino acid unit therein, then the free amino group —NH$_2$ of said basic amino acid unit has been replaced with a —NHCOOR$_5$ group wherein R$_5$ is $C_1$–$C_7$ alkyl or benzyl; and (2) when the C-terminal amino acid is as defined in (d) or (e) above, then the peptide also has a basic amino acid unit therein whose free amino group —NH$_2$ is replaced with a —NHCOOR$_4$ group wherein R$_4$ is defined as above.

The molecularly packaged peptides of formula (I) are the reduced, dihydropyridine forms of the new redox system provided by the present invention, and the form intended for administration.

The present invention further provides novel quaternary intermediates to the peptides of formula (I), which intermediates have the structural formula

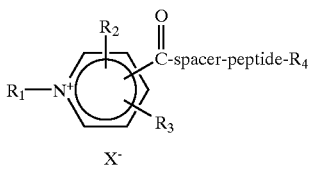

(II)

wherein:

X⁻ is the anion of a non-toxic, pharmaceutically acceptable acid;

and "spacer", "peptide", $R_1$, $R_2$, $R_3$ and $R_4$ are as defined with formula (I) above. In addition to being chemical intermediates to the corresponding dihydropyridine final products of formula (I), the quaternaries of formula (II) are produced in vivo by enzymatically mediated oxidation of the reduced form (I). The resultant polar conjugate is trapped ("locked-in") behind the lipoidal blood-retinal barrier. Over time, cleavage of the lipophilic ester from the oxidized form of the system by esterase or lipase enzymes (which affords the corresponding quaternary conjugates in which the —$OR_4$ group has been replaced with an —OH group, which are likewise "locked in" the retina and which may exert characteristic peptide-like activity) and enzymatic cleavage of the targetor-spacer portion from the peptides results in release of active peptides in the retina.

DETAILED DESCRIPTION OF THE INVENTION AND THE PREFERRED EMBODIMENTS

More particularly in accord with the present invention, the following definitions are applicable:

The term "lipoidal" as used herein is intended to mean lipid-soluble or lipophilic.

The term "halo" encompasses fluoro, chloro, bromo and iodo.

The term "$C_1$–$C_7$ alkyl" includes straight and branched lower alkyl radicals having up to seven carbon atoms. When $R_2$ and/or $R_3$ are $C_1$–$C_7$ alkyl, they are preferably methyl or ethyl. When $R_1$ is $C_1$–$C_7$ alkyl, it is preferably methyl.

The term "$C_1$–$C_7$ alkoxy" includes straight and branched chain lower alkoxy radicals having up to seven carbon atoms. When $R_2$ and/or $R_3$ are $C_1$–$C_7$ alkoxy, they are preferably methoxy or ethoxy.

The term "$C_2$–$C_8$ alkoxycarbonyl" designates straight and branched chain radicals of the formula

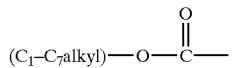

wherein the $C_1$–$C_7$ alkyl group is defined as above. When $R_2$ and/or $R_3$ are alkoxycarbonyl, they are preferably ethoxycarbonyl or isopropoxycarbonyl.

The term "$C_2$–$C_8$ alkanoyloxy" designates straight and branched chain radicals of the formula

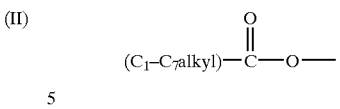

wherein the $C_1$–$C_7$ alkyl group is defined as above. When $R_2$ and/or $R_3$ are alkanoyloxy, they are preferably acetoxy, pivalyloxy or isobutyryloxy.

The term "$C_1$–$C_7$ haloalkyl" designates straight and branched chain lower alkyl radicals having up to seven carbon atoms and bearing one to three halo substituents (F, Cl, Br or I), which can be the same or different. Specific examples of the contemplated monohaloalkyl and polyhaloalkyl groups include chloromethyl, dichloromethyl, trichloromethyl, bromomethyl, fluoromethyl, difluoromethyl, trifluoromethyl, 1-fluoroethyl, 1-chloroethyl, 2-chloroethyl, 2,2,2-trichloroethyl, 2,2,2-trifluoroethyl, 1,2-dichloroethyl, 1-chloropropyl, 3-chloropropyl, 1-chlorobutyl, 1-chloropentyl, 1-chlorohexyl, 4-chlorobutyl and the like. Preferably, the haloalkyl group contains 1 or 2 carbon atoms and bears 1 to 3 halogen substituents, e.g. chloromethyl or trifluoromethyl.

The term "$C_1$–$C_7$ alkylthio" includes straight and branched chain radicals of the type

wherein $C_1$–$C_7$ alkyl is defined as before. When $R_2$ and/or $R_3$ are alkylthio, they are preferably methylthio.

The terms "$C_1$–$C_7$ alkylsulfinyl" and "$C_1$–$C_7$ alkylsulfonyl" designate radicals of the formulas

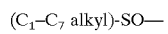

and

respectively, wherein $C_1$–$C_7$ alkyl is defined as before. When $R_2$ and/or $R_3$ are alkylsulfinyl or alkylsulfonyl, methylsulfinyl and methylsulfonyl are preferred.

When $R_2$ and/or $R_3$ are —CH=NOR''', they are preferably —CH=NOH or —CH=NOCH$_3$.

When $R_2$ and/or $R_3$ are —CONR'R'', they are preferably —CONH$_2$ or —CON(CH$_3$)$_2$.

The term "$C_7$–$C_{12}$ aralkyl" as used herein designates radicals of the type

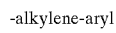

wherein the aryl portion is phenyl or naphthyl and the alkylene portion, which can be straight or branched, can contain up to 6 carbon atoms, e.g., methylene, ethylene, propylene, trimethylene, 1,2-butylene, 2,3-butylene, tetramethylene and the like. When $R_1$ is aralkyl, it is preferably benzyl.

The expression "non-toxic pharmaceutically acceptable salts" as used herein generally includes the non-toxic salts of compounds of formula (I) formed with non-toxic, pharmaceutically acceptable inorganic or organic acids HX. For example, the salts include those derived from inorganic acids such as hydrochloric, hydrobromic, sulfuric, sulfamic, phosphoric, nitric and the like; and the salts prepared from organic acids such as acetic, propionic, succinic, glucolic, stearic, lactic, malic, tartaric, citric, ascorbic, pamoic, maleic, hydroxymaleic, phenylacetic, glutamic, benzoic, salicyclic, sulfanilic, fumaric, methanesulfonic, toluenesulfonic and the like. The expression "anion of a non-toxic pharmaceutically acceptable acid" as used herein, e.g., in connection with structure (II), is intended to include anions of such organic or inorganic acids HX.

The expression "hydroxyl protective group" as used herein is intended to designate a group (Y) which is inserted in place of a hydrogen atom of an OH group or groups in order to protect the OH group(s) during synthesis and/or to improve lipoidal characteristics and prevent premature metabolism of the OH group(s) prior to the compound's reaching the desired site in the body. The expression "protected hydroxy substituent" designates an OY group wherein Y is a "hydroxyl protective group" as defined above. Preferably, however, the redox portion of the molecule does not bear either a hydroxy or protected hydroxy group. Such protective groups are, on the other hand, frequently used during synthesis of the "spacer-peptide" section of the molecule and occasionally are retained in the final product if it contains a particularly vulnerable hydroxy function.

Typical hydroxyl protective groups contemplated by the present invention are acyl groups and carbonates. When the hydroxyl protective group is acyl (i.e., when it is an organic radical derived from a carboxylic acid by removal of the hydroxyl group), it preferably represents an acyl radical selected from the group consisting of alkanoyl having 2 to 8 carbon atoms; alkenoyl having one or two double bonds and 3 to 8 carbon atoms;

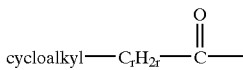

wherein the cycloalkyl portion contains 3 to 7 ring atoms and r is zero, one, two or three; phenoxyacetyl; pyridinecarbonyl; and

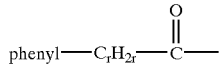

wherein r is zero, one, two or three and phenyl is unsubstituted or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 2 to 6 carbon atoms.

When the acyl group is alkanoyl, there are included both unbranched and branched alkanoyl, for example, acetyl, propionyl, butyryl, isobutyryl, valeryl, isovaleryl, 2-methylbutanoyl, pivalyl (pivaloyl), 3-methylpentanoyl, 3,3-dimethylbutanoyl, 2,2-dimethylpentanoyl and the like. Pivalyl, isobutyryl and isovaleryl are especially preferred.

When the acyl group is alkenoyl, there are included, for example, crotonyl, 2,5-hexadienoyl and 3,6-octadienoyl.

When the acyl group is

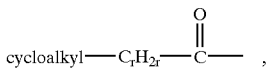

there are included cycloalkanecarbonyl and cycloalkanealkanoyl groups wherein the cycloalkane portion can optionally bear 1 or 2 alkyl groups as substituents, e.g., cyclopropanecarbonyl, 1-methylcyclopropanecarbonyl, cyclopropaneacetyl, α-methylcyclopropaneacetyl, 1-methylcyclopropaneacetyl, cyclopropanepropionyl, α-methylcyclopropanepropionyl, 2-isobutylcyclopropanepropionyl, cyclobutanecarbonyl, 3,3-dimethylcyclobutanecarbonyl, cyclobutaneacetyl, 2,2-dimethyl-3-ethylcyclobutaneacetyl, cyclopentanecarbonyl, cyclohexaneacetyl, cyclohexanecarbonyl, cycloheptanecarbonyl and cycloheptanepropionyl. Cyclohexanecarbonyl is especially preferred.

When the acyl group is pyridinecarbonyl, there are included picolinoyl(2-pyridinecarbonyl), nicotinoyl(3-pyridinecarbonyl) and isonicotinoyl(4-pyridinecarbonyl).

When the acyl group is

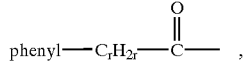

there are included, for example, benzoyl, phenylacetyl, α-phenylpropionyl, β-phenylpropionyl, p-toluyl, m-toluyl, o-toluyl, o-ethylbenzoyl, p-tert-butylbenzoyl, 3,4-dimethylbenzoyl, 2-methyl-4-ethylbenzoyl, 2,4,6-trimethylbenzoyl, m-methylphenylacetyl, p-isobutylphenylacetyl, β-(p-ethylphenyl)propionyl, p-anisoyl, m-anisoyl, o-anisoyl, m-isopropoxybenzoyl, p-methoxyphenylacetyl, m-isobutoxyphenylacetyl, m-diethylaminobenzoyl, 3-methoxy-4-ethoxybenzoyl, 3,4,5-trimethoxybenzoyl, p-dibutylaminobenzoyl, 3,4-diethoxyphenylacetyl, β-(3,4,5-trimethoxyphenyl) propionyl, o-iodobenzoyl, m-bromobenzoyl, p-chlorobenzoyl, p-fluorobenzoyl, 2-bromo-4-chlorobenzoyl, 2,4,6-trichlorobenzoyl, p-chlorophenylacetyl, α-(m-bromophenyl)propionyl, p-trifluoromethylbenzoyl, 2,4-di(trifluoromethyl)benzoyl, m-trifluoromethylphenylacetyl, β-(3-methyl-4-chlorophenyl)propionyl, p-dimethylaminobenzoyl, p-(N-methyl-N-ethylamino)benzoyl, o-acetamidobenzoyl, m-propionamidobenzoyl, 3-chloro-4-acetamidophenylacetyl, p-n-butoxybenzoyl, 2,4,6-triethoxybenzoyl, β-(p-trifluoromethylphenyl)propionyl, 2-methyl-4-methoxybenzoyl, p-acetamidophenylpropionyl and 3-chloro-4-ethoxybenzoyl.

When the hydroxyl protective group is a carbonate grouping, it has the structural formula

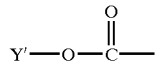

i.e., it is an organic radical which can be considered to be derived from a carbonic acid by removal of the hydroxyl group from the COOH portion. Y' preferably represents alkyl having 1 to 7 carbon atoms; alkenyl having one or two double bonds and 2 to 7 carbon atoms;

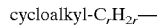

wherein the cycloalkyl portion contains 3 to 7 ring atoms and r is zero, one, two or three; phenoxy; 2-, 3-, or 4-pyridyl; or

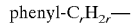

wherein r is zero, one, two or three and phenyl is unsubstituted or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 2 to 6 carbon atoms. Most preferably, Y' is $C_1$–$C_7$ alkyl, particularly ethyl or isopropyl.

The polycycloalkyl-$C_pH_{2p}$— radicals represented by $R_4$ are bridged or fused saturated alicyclic hydrocarbon systems consisting of two or more rings, optionally bearing one or more alkyl substituents and having a total of 6 to 30 carbon atoms in the ring portion, including the possible alkyl substituents but not including the carbon atoms in the —$C_pH_{2p}$— portion. The corresponding bridged or fused unsaturated alicyclic hydrocarbon systems are intended by the term "$C_6$–$C_{30}$ polycycloalkenyl —$C_pH_{2p}$—". In both cases, p is preferably 0, 1 or 2. Such polycycloalkyl and polycycloalkenyl radicals are exemplified by adamantyl (especially 1- or 2-adamantyl), adamantylmethyl (especially 1-adamantylmethyl), adamantylethyl (especially 1-adamantylethyl), bornyl, norbornyl, (e.g., exo-norbornyl or endo-norbornyl), norbornenyl (e.g., 5-norbornen-2-yl), norbornylmethyl (e.g., 2-norbornylmethyl) and norbornyl-ethyl (e.g., 2-norbornylethyl), decahydronaphthyl (e.g., cis or trans decahydronaphthyl-2-yl), 6,6-dimethylbicyclo[3.1.1]hept-2-en-2-ethyl, (±)-(3-methylnorborn-2-yl) methyl, 1,3,3-trimethyl-2-norbornyl and 5-norbornene-2-methyl; and by radicals of the type —$C_pH_{2p}$-steryl where p is defined as above but is preferably zero, and "steryl" is: (i) the residue of a steroidal alcohol, i.e., the portion which would remain after removal of the hydroxy group therefrom, or (ii) the residue of a steroidal carboxylic acid, i.e., the portion which would remain after removal of the —COOH group therefrom.

The following structures are representative of steryl residues derived from steroidal alcohols for use herein:

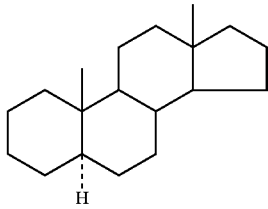

androstanes/androstenes
-$\Delta^5$-3β, 17 β-diol
-$\Delta^{16}$-3 α-ol
-3α-ol-17-one
-3β-ol-17-one
-$\Delta^5$-3β-ol-17-one

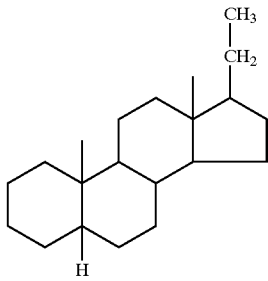

pregnanes/pregnenes
-3α, 20-diol
-3α-ol-20-one
-$\Delta^4$-21-ol-3,11-dione
-$\Delta^4$-17α- 20, 21-triol-3-one
-$\Delta^5$-3β-ol-20-one

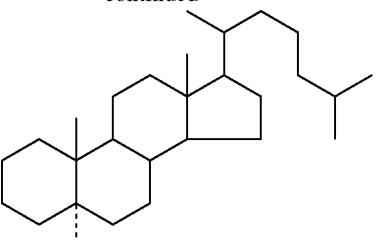

cholestanes/cholestenes
-3β-ol
-$\Delta^5$-3β-ol (cholesterol)

Among the foregoing, the residue of cholesterol is especially preferred.

The following structures are representative of steroidal carboxylic acids from which steryl residues are preferably derived:

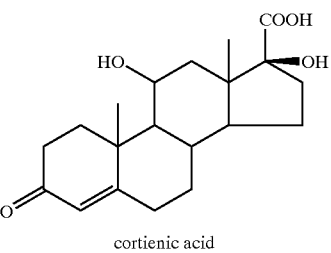

cortienic acid

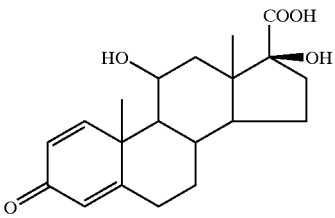

$\Delta^1$-cortienic acid

In the case of cortienic acid and $\Delta^1$-cortienic acid, the 17-hydroxy group is suitably protected as a $C_1$–$C_7$ alkyl ether, preferably a methyl ether. The corresponding steryl groups are

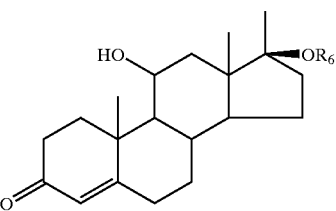

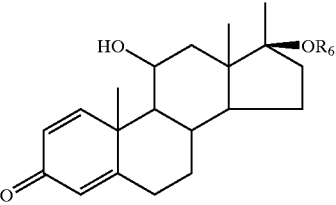

Introduction of the $R_4$ group into the formula (I) or (II) compounds, or more usually into their synthetic precursors, depends on the nature of the functional group to which $R_4$ is to be attached in the peptide. When attachment to a terminal —COOH group in a peptide or peptide precursor is desired, the carboxyl group of what will ultimately be the C-terminal amino acid of the peptide can be reacted with the selected alcohol $R_4OH$, e.g. steryl-$C_pH_{2p}$—OH or adamantyl-$C_pH_{2p}$—OH, typically cholesterol or adamantaneethanol, to replace the terminal —COOH with —COOR$_4$. When the peptide has a C-terminal —CH$_2$OH group to which $R_4$ is to be attached, the —CH$_2$OH group of what will ultimately be the C-terminal amino acid can be reacted with $R_4COOH$ (e.g. cortienic acid 17-methyl ether or adamantaneacetic acid) to replace the terminal —CH$_2$OH with —CH$_2$OCOR$_4$. When the peptide has a C-terminal —CONH$_2$ group to which $R_4$ is to be attached, a C-terminal —CO-Gly-OR$_4$ group is formed [by reacting the corresponding peptide having a C-terminal —COOH group and an N-terminal protected amin with a reactant such as Gly-O-cholesteryl (formed from $R_4OH$ as described in Scheme VII below)], which will regenerate the desired —CONH$_2$ group in vivo. When it is desired to attach the $R_4$ group to a basic amino acid function in the peptide, generally a Lys unit, the free —NH$_2$ group of that unit can be reacted with cholesteryl chloroformate or adamantaneethyl chloroformate to convert the —NH$_2$ group to a —NHCOOR$_4$ group.

Especially preferred compounds of the present invention are the "packaged" peptides of formula (I) in which the

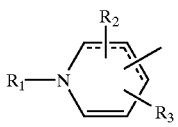

portion of the molecule has one of the following structures:

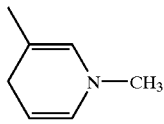 (a)

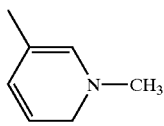 (b)

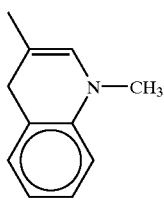 (c)

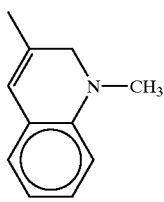 (d)

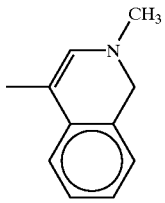 (e)

The corresponding quaternary salts of formula (II) have the partial structures:

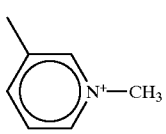 (a'/b')

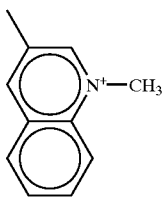 (c'/d')

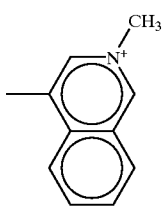 (e')

The expression "carboxyl protective group" as used herein is intended to designate a group (W) which is inserted in place of a hydrogen atom of a COOH group or groups in order to protect the COOH group(s) during synthesis and/or to improve lipoidal characteristics and prevent premature metabolism of said COOH group or groups prior to the compound's reaching the desired site in the body, but excluding any C-terminal —COOH group in formulas (I) and (II), at which location an $R_4$ group will be incorporated. Typical of such other carboxyl protective groups W are the groups encompassed by Y' above, especially $C_1$–$C_7$ alkyl, particularly ethyl, isopropyl and t-butyl. Such groups are not intended for use in place of $R_4$, as they are ineffective. Each compound of formulas (I) and (II) must contain an $R_4$ group. Usually, carboxyl protecting for other positions are solely for protection during synthesis, and then only the usual synthetic requirements will generally apply.

Carboxyl protecting groups for use in peptide synthesis are well-known to those skilled in the art. See, for example, M. Bodanszky, *Principles of Peptide Synthesis,* Springer-Verlag, New York 1984, Ives U.S. Pat. No. 4,619,915 and the various publications on peptide chemistry referred to in the Ives patent. See also *Methoden der Organischen Chemie,* Houben-Weyl, Volume 15/1 for protecting groups and Volume 15/2 for methods of peptide synthesis. Representative carboxyl protecting groups for synthetic purposes include various silyl esters (e.g., trialkylsilyl and trihalosilyl esters), alkyl esters (e.g., tert-butyl esters), benzyl esters and the other carboxyl protecting groups mentioned in the Ives patent.

The expression "amino protective group" as used herein is intended to designate a group which is inserted in place of a hydrogen atom of an amino group or groups in order to protect the amino group(s) during synthesis. Appropriate amino protecting groups are known in the art and are described, for example, in the Bodanszky, Ives and Houben-Weyl references cited above. Representative amino protecting groups for synthetic use include acyl groups such as tert-butoxycarbonyl, benzyloxycarbonyl, benzoyl, acetyl and the like. Yet other conventional amino protecting groups for use in synthesis are described in the literature, e.g., in the Bodanszky publication and Ives patent referred to hereinabove.

When the peptide contains a basic amino acid such as lysine, which has a free amino group not involved in a peptide bond with an adjacent amino acid, then the free amino group needs to be protected both for synthetic purposes and for use in vivo. This can be accomplished in certain instances by introducing the $R_4$ group at that location, converting —$NH_2$ to —$NHCOOR_4$ as discussed above. However, when the $R_4$ group is introduced at a different location, then the —$NH_2$ group should be protected as a —$NHCOOR_5$ group wherein $R_5$ is $C_1$–$C_7$ alkyl or benzyl (preferably t-butyl).

The various protecting groups for hydroxyl, carboxyl and amino functions discussed above can be substituted for the hydroxyl, carboxyl and amino functions in the instant peptides or their precursor molecules by methods well-known in the art. Methods for chemical removal of the protecting groups (when such are not to be retained in the pharmaceutically useful end product) are likewise well-known to those skilled in the art. Typically, amine protecting groups are chemically removed by acidolysis (acid hydrolysis) or hydrogenation, depending on the particular protecting group employed. Hydroxyl and carboxyl protecting groups are typically removed chemically by acid or base hydrolysis. Protecting groups which are incorporated in the pharmaceutical end product must be amenable to hydrolytic or metabolic cleavage in vivo.

The "spacer" portion of the compounds of the invention is composed of from 1 to 3 L-amino acid units. Each unit is a naturally occurring L-amino acid. Any natural amino acid may be present as each of the 1 to 3 units, which may be the same or different; however, those which have excess reactive functional groups beyond those needed to attach to the redox moiety at one end and the rest of the peptide at the other may be disadvantageous as compared to the neutral amino acids (e.g., glycine, alanine, valine, leucine, isoleucine, phenylalanine, proline, tryptophan, asparagine and glutamine). Preferred amino acid segments are alanine, proline, glycine and phenylalanine. Preferred spacers include Ala, Ala-Ala, Ala-Pro, Pro, Pro-Pro and Pro-Ala. Spacers utilizing alanine and proline segments are particularly preferred because there are peptidases which specifically cleave between alanine and an adjacent amino acid and between proline and an adjacent amino acid. For example, alanine-aminopeptidase and proline-endopeptidase can facilitate cleavage of the growth factor inhibitory peptide from a spacer having those amino acids, in addition to numerous less specific degrading enzymes for which any of the "packaged" peptides serve as substrates. A most especially preferred spacer for use herein is -Pro-Pro-.

The "peptide" portion of the compounds of the invention is a peptide having growth factor inhibitory activity and 2–20 amino acid units. This peptide is typically a known synthetic peptide having activity which inhibits growth hormone or insulin-like growth factor 1 or other growth factor mentioned earlier in this description. Preferred growth factor inhibitors for delivery to the retina in accord with the present invention are somatostatin analogs. Preferred somatostatin analogs for the purposes of the present invention include octreotide and lanreotide (whose structures are set forth earlier in this description) and analogs of these peptides, for example the following peptides which can be considered analogs of octreotide:

[SEQ ID NO.:4]

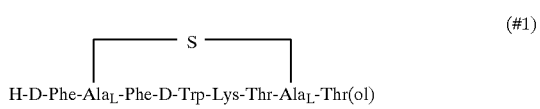

(#1)

[SEQ ID NO.:5]

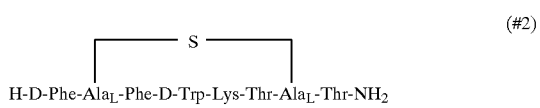

(#2)

[SEQ ID NO.:6]

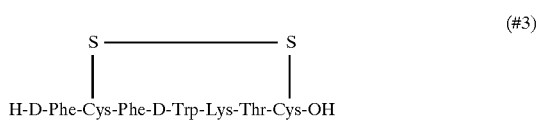

(#3)

In the present discussion of peptides suitable for "packaging" in accord with the present invention, the conventional peptide representation (amino terminus on left, carboxyl terminus on right) will be used, as will the conventional abbreviations for the individual amino acid units (Phe for phenylalanine, Gly for glycine, and so forth). Insofar as concerns configuration, in this general discussion the configuration of optically active amino acids will be assumed to be L unless otherwise specified.

In general, the peptide derivatives provided by the present invention are prepared by sequential addition of one or more amino acids or protected amino acids, with the precursor redox system being either first added to an amino acid or dipeptide which is then added to the growing spacer-peptide or peptide chain, or else added directly to the spacer-peptide after that portion has been completed. Methods for sequential addition of amino acids to form peptides, utilizing protecting groups where appropriate, are well-known in the art. An excellent summary of such methods, including both solid phase synthesis and synthesis in solution, in contained in Nestor et al. U.S. Pat. No. 4,530,920, which is incorporated in reference herein in its entirety and relied upon. See also *SOLID PHASE PEPTIDE SYNTHESIS*, second edition, John Morrow Stewart and Janis Dillaha Young, Pierce Chemical Company, Rockford, Ill., 1984.

Peptides provided by the present invention can also be prepared by segment condensation methods described in the literature, e.g., in the Bodanszky and Houben-Weyl references cited above.

The precusor of the redox portion of the compounds of formulas (I) and (II) may be introduced before or after introduction of the $R_4$ group, depending upon the particular peptide being derivatized. It is often convenient to add the redox precursor to the spacer, and then add the redox precursor-spacer to the remainder of the molecule, for example, as set forth in EXAMPLES 2 and 3 hereinbelow. The precursor of the redox portion of the molecule has the formula

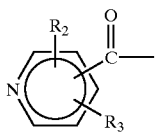

wherein $R^2$ and $R^3$ are defined as above.

Generally, the last two steps of the synthesis consist of oxidizing the intermediate of the formula

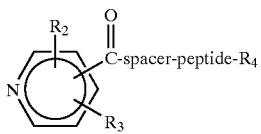

to the corresponding quaternary pyridinium salt of formula (II), followed by reduction to afford the corresponding compound of formula (I).

When an anion is desired which is different from the one obtained by one of the processes described above, the anion in the quaternary salt of formula (II) may be subjected to anion exchange via an anion exchange resin or, more conveniently, by use of the method of Kaminski et al, *Tetrahedron*, Vol. 34, pp. 2857–2859 (1978). According to the Kaminski et al method, a methanolic solution of an HX acid will react with a quaternary ammonium halide to produce the methyl halide and the quaternary .X salt.

Reduction of the quaternary salts of formula (II) to the corresponding dihydro derivatives of formula (I) is usually conducted at a temperature from about −10° C. to room temperature, for a period of time from about 10 minutes to 3 hours, conveniently at atmospheric pressure. The process is conducted in the presence of a suitable reducing agent. Selection of an appropriate reducing agent needs to take into consideration any amino acid units in the molecule which might not readily withstand the reduction conditions. Many somatostatin analogs, including octreotide and lanreotide, are cyclic amino acids containing a disulfide bridge —S—S— which will not withstand the conditions which are acceptable to analogs containing the more stable —S— bridge. For the compounds not having a disulfide bridge or other susceptible moiety, the reducing agent is preferably an alkali metal dithionite such as sodium dithionite, an alkali metal borohydride such as sodium borohydride or lithium aluminum borohydride, or a more reactive dihydropyridine such as 1-benzyl-1,2-dihydroisonicotinamide.

Sodium dithionite reduction is conveniently carried out in an aqueous solution, e.g., aqueous methylene chloride, in the presence of base, e.g., sodium bicarbonate, and, in the case of pyridinium and quinolinium starting materials, generally affords a preponderance of 1,4-dihydro isomer. The dihydro product is usually insoluble in water and thus can be readily separated from the sodium dithionite reaction medium.

In the case of sodium borohydride reduction, an organic reaction medium is typically employed, e.g., a lower alkanol such as methanol, an aqueous alkanol or other protic solvent. For pyridinium and quinolinium starting materials, sodium borohydride reduction typically affords a preponderance of the 1,6-dihydropyridine and 1,2-dihydroquinoline isomers, respectively.

Other useful reducing agents include dihydropyridines which are more reactive than the quaternary salts which are to be reduced. A particularly suitable reagent of this type is the highly reactive 1-benzyl-1,2-dihydroisonicotinamide, which can be used for selective reduction of the quaternary salts by a direct hydride transfer reaction under neutral conditions [Nuvole et al, *J. Chem. Research,* 1984, (S), 356]. Thus, for example, pyridinium and quinolinium salts of the invention can be regioselectively reduced to the corresponding 1,4-dihydropyridines and 1,4-dihydroquinolines, respectively, utilizing 1-benzyl-1,2-dihydroisonicotinamide as the reducing agent, typically in a suitable organic reaction medium, e.g., anhydrous methanol. Other possible reducing agents of the reactive dihydropyridine type include ribosyl N-methyl dihydronicotinamide (derived from NADH).

When the peptide is octreotide, lanreotide or other peptide containing a disulfide bridge, the reducing agent of choice is 1-benzyl-1,2-dihydroisonicotinamide. Appropriate solvents and reaction conditions are described in the EXAMPLES hereinafter.

The SCHEMES and EXAMPLES which follow illustrate the preparation of a variety of representative compounds of formula (I) and intermediates thereto. Many modifications in these methods may be utilized, including use of a peptide synthesizer, variations in protecting groups for the various functional groups used to build the peptide sequence, variations in solvents, reaction conditions, and of course variations in the reactants containing the redox moiety or the bulky ester group —$OR_4$, in the spacer and in the growth factor inhibitory peptide.

Especially desirable alternates for the nicotinic acid reactant, used to introduce alternate redox moieties into the compounds of formula (I), include isonicotinic acid, picolinic acid, 4-isoquinolinecarboxylic acid, 3-quinolinecarboxylic acid, 4-quinolinecarboxylic acid, and substituted derivatives of these compounds or of nicotinic acid.

Especially desirable alternates for the N-protected-L-prolines used to build the spacer portion of the compounds of formula (I) are the corresponding alanine, glycine and phenylalanine protected derivatives, used singly or combined with proline and/or alanine protected derivatives.

Especially desirable alternates for cholesterol, the alcohol ($R_4OH$) used to introduce the bulky $R_4$ function, are other sterols such as 3β-hydroxyandrostan-17-one, β-sitosterol and pregnane-3α,20-diol; and cyclic alcohols such as those depicted below:

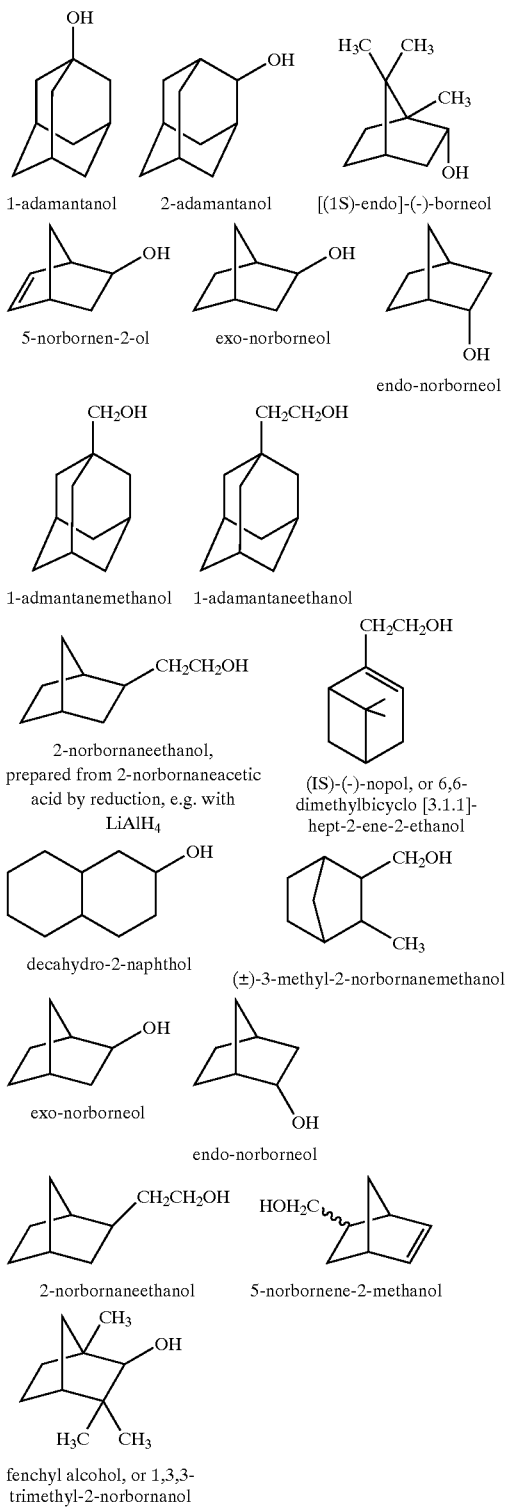

Variations in the amino acids used to build the active peptide portion of the compounds of formula (I) will be apparent from the discussion of such peptides earlier in this description.

The rationale for investigating octreotide and lanreotide in advanced diabetic retinopathy includes their potent suppression of pituitary GH and growth factor inhibiting activity. Clinical responses outlined hereinabove provide evidence that the strategy can be effective in halting the progression of diabetic retinopathy, but these trials were effective in patients with compromised BRB integrity. The envisioned therapeutic role for packaged peptides of the present invention preferably involves treating insulin dependent diabetes mellitus patients for critical periods in diabetic retinopathy disease progression, before laser photocoagulation is indicated. The drug would preferably be used for 1–4 month intervals when a patient is experiencing severe nonproliferative DR or is found to have low risk proliferative DR. Enhanced and sustained peptide delivery to retinal tissues in accord with the present invention would permit increased dosing intervals (i.e., every 24–48 hours) compared to multiple or continuous injection of the non-packaged peptide. The interval dosing strategy would circumvent somatostatin receptor down regulation that has been suggested after 6 months treatment with octreotide in patients with severe proliferative DR refractory to pan-photocoagulation. Several other advantages are offered by limited interval therapy compared to continuous, prolonged parenteral treatment. Advantages range from drug development issues to patient compliance and economics.

Documented differences in BBB and BRB permeability indicate that drug design can succeed in enhancing retinal delivery without significant CNS effects. Somatostatin receptors are widely distributed throughout the body including the brain and the endogenous peptide has numerous inhibitory roles that are mediated through several types of somatostatin receptors. While studies have shown both native somatostatin and somatostatin receptors in the retina, retinal receptors are not yet completely characterized for possible differences with CNS receptors.

Available evidence indicates that packaged somatostatin analogs should be well-tolerated by peripheral tissues. The stable somatostatin analogs have been found to be better tolerated than native somatostatin in dose tolerance studies. The clinical picture in diabetics given somatostatin or somatostatin analogs shows peptide benefits with lower amplitude and frequency for serum glucose fluctuations. While lanreotide is known to suppress insulin secretion in normal physiological conditions, insulin suppression is not a factor in IDDM patients. The somatostatin analogs are approximately 45 times more potent than natural somatostatin in inhibiting GH secretion, yet exert much less inhibition on insulin, glucagon, and gastric acid secretion. Similarly, structure activity studies have shown that the stable analogs are more potent inhibiting angiogenesis than the native tetradecapeptide. Clinically, what is observed in diabetics treated with stable somatostatin analogs is fewer and less dramatic daily fluctuations of serum glucose. If peripheral tissue excretion of the oxidized metabolite of a CDS of the present invention proves too rapid, the CDS can be supplemented with unmodified somatostatin analog for peripherally mediated beneficial effects of improved glucose control.

Adequate experimental models for proliferative diabetic retinopathy are not available in either spontaneous genetic or chemically induced animal models of diabetes. An experimental in vivo model for proliferative diabetic retinopathy can be used to identify the potential efficacy and dosing requirements for drug candidates. Clinical evidence supports a role for IGF-1 in development and progression of diabetic retinopathy as outlined hereinabove and in vitro studies have implicated growth factors in basement membrane changes, cell chemotaxis and cell proliferation. While studies have shown that stable somatostatin analogs demonstrate significant inhibitory activity in the chorioallantoic membrane of the developing chick embryo, this assay for angiogenesis cannot evaluate targeted drug delivery systems. Therefore, an in vivo animal model for retinal angiogenesis has been developed that does not involve endogenous insulin suppression or exogenous insulin treatment. Specific objectives for an animal model include evaluating IGF-1 as an angiogenic agent in retinal neovascularization. The efficacy of packaged peptide of formula (I) can be tested in this new animal model of retinal angiogenesis.

Pigmented rabbits were selected for study after considering the ocular anatomy, animal supply and established use of the species in ophthalmology. Growth factor was injected into the vitreous of pigmented rabbits (n=30) as previously described. Briefly, rabbits were anesthetized with ketamine and xylazine and a 30 g needle was used to withdraw 80 μl of fluid from the anterior eye chamber under an operating microscope. Then a 30 g needle was used to administer 0.1 ml of balanced salt solution containing 600 ug of IGF-1 adjacent to the surface of the retina near the optic nerve head. The rabbits were placed in a supine position for 30–60 minutes to facilitate solution dispersal onto the vascularized medullary ray and disc. Control animals (n=10) received the same dose of heat-inactivated protein (IGF-1 held at 100° C. for 30 min). Animals were periodically examined using indirect ophthalmoscopy, fundus photography, and fluorescein angiography from days 2 through 21.

The temporal sequence of the anatomical changes seen in the IGF 1-injected eyes is as follows. Ophthalmoscopy revealed hyperemia with vascular engorgement in all rabbits, 3 days after intravitreal IGF-1 injection. Vascular tortuosity, intraretinal hemorrhage, and severe increased hyperemia surrounding the optic disc were noted by day 7 in all rabbits. Fibrosis developed over the optic disc and medullary ray in all rabbits by day 21 of the study. The fundus of control eyes remained normal in appearance. Microscopically, abnormal vessels were observed on the surface of the retina in all eyes treated with IGF-1. Numerous distended vessels with edematous endothelial cells were found on the surface of the retina along with extensive proliferation of their extracellular matrix. Control eyes injected with heat-inactivated IGF-1 showed sparse vascular channels lined by flat endothelial cells with minimal extracellular matrix. Electron microscopic studies revealed that edematous endothelial cells with increased smooth and rough endoplasmic reticulum were a prominent feature of retinal vessels in eyes injected with IGF-1. Reduplication of the basement membrane, a strong indicator of endothelial cell hyperreactivity, was a consistent finding in all IGF-1 treated eyes. Endothelial cell mitosis was validated using antibody to proliferating cell nuclear antigen. Systemic unpackaged peptide, e.g. lanreotide can be tested for its ability to inhibit IGF-1 induced neovascularization in this rabbit model.

In one aspect, the present invention is directed toward improved retinal delivery of the enzymatically stable somatostatin analog, lanreotide (LNT), a cyclic peptide that shows inhibitory action on angiogenesis in preclinical studies and appears to impede diabetic retinopathy disease progression in patients with compromised BRB. Applying molecular packaging principles, developed for enhanced delivery of peptides through the BBB, to LNT for enhanced delivery through the BRB, the following studies are deemed appropriate and are representative of the types of studies to be used for "packaged" versions of other somatostatin analogs in accord with the present invention:

First, the distribution of unmodified LNT to retina, brain, blood, plasma and selected peripheral tissues in vivo is characterized. As discussed more fully below, this includes: (i) adapting techniques previously used to examine the distribution profile in rats to studies in the guinea pig; and (ii) developing analytical techniques compatible with dihydropyridine chemistry for evaluating LNT tissue levels. This phase of the study establishes the baseline to quantitatively evaluate effects of molecular packaging strategy on LNT delivery to the retinal tissue as well as in characterizing differences in BBB and BRB penetration of packaged and unpackaged peptides. The series of studies in this phase include: (i) examining $^{125}$I-LNT distribution profiles from 5 minutes through 24 hours following an i.v. bolus of LNT; (ii) adapting radioimmunoassay (RIA) methods published for rat tissues to guinea pig tissues; (iii) using immunocytochemical techniques to visualize LNT in retina; and (iv) adapting mass spectroscopy methods used to evaluate brain enkephalin profiles to retinal LNT profiles. The guinea pig was chosen after considering the size of retinal tissue relative to rats and mice, animal husbandry and cost relative to dogs. An important consideration involves species compatability with sensitive RIA detection methods for LNT. The only validated RIA method employs a polyclonal first antibody that was generated in a rabbit, therefore, the guinea pig was selected for distribution studies. Howeer, other appropriate animal models can be designed.

Secondly, the enzymatic activities in retinal tissue that are critical for molecular packaging to achieve enhanced, sustained peptide delivery through retrometabolic processing are characterized. Studies in vitro are used to verify that oxidation of the T functional group precedes hydrolysis of the L and S functional groups. Studies include: (i) adapting techniques developed to examine metabolic profiles in the rat brain to guinea pig retinal tissue; and (ii) studying retinal processing of packaged CDS-enkephalin and CDS-TRH compounds as model compounds. This will guide design of target CDS compounds for enhanced LNT retinal delivery.

Thirdly, LNT-CDS compounds are designed and synthesized. In this step: (i) design considers results from in vitro metabolism studies of model compounds; (ii) synthesis establishes synthetic routes; and (iii) scale-up procedures can be considered. This will include, for example, synthesizing new LNT-CDS compounds having the following structure (Ia): [SEQ ID NO. :7]

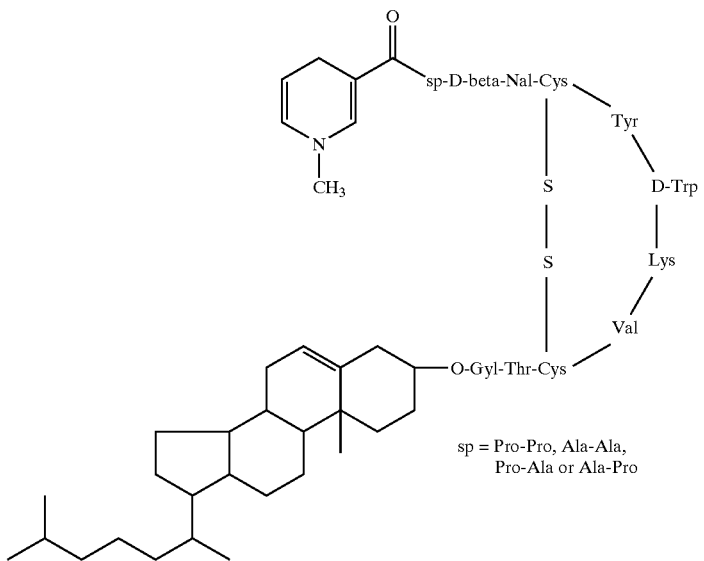

Fourthly, the LNT-CDS compounds are evaluated for enhanced retinal delivery. This aspect of the study involves: (i) characterizing the metabolism in vitro to show that oxidation precedes hydrolysis in retinal tissue; (ii) comparing the distribution profile of LNT-CDS to unmodified LNT in vivo in guinea pigs; and (iii) assessing the pharmacological activity of LNT-CDS in an animal model of growth factor-induced ocular neovascularization.

The rationale for these studies is to first show that the barrier function of the BRB does limit penetration of LNT, and secondly, to establish baseline parameters for unmodified LNT that can be used to evaluate the degree of enhanced peptide delivery afforded by molecular packaging. The guinea pig was chosen for study after considering: animal and retina size, animal supply and husbandry, and species compatibility with characterized and specific LNT antibody that was generated in a rabbit.

Several studies have shown that retinal tissue has somatostatin receptors and evidence for the role of growth factors in DR indicates that stable somatostatin analogs should be effective in treating DR. Yet, clinical studies suggested octreotide or LNT were only effective in advanced disease where the BRB is severely compromised. An important aspect of this step characterizes the magnitude of LNT penetration and duration profile in the intact retina.

A first study examines the $^{125}$I-LNT distribution profile from 5 minutes through 24 hours after intracardiac injection of radiolabelled LNT(200 μg/kg). Procedures follow the published study characterizing LNT distribution in the rat which was unable to detect significant LNT levels in rat eyes after a similar dose. Unmodified LNT (obtained from the Henri Beaufour Institute, Washington, D.C.) is iodinated with $^{125}$Iodine using the standard chloramine-T procedure of Hunter and Greenwood and diluted with unlabelled LNT to result in approximately 1 μCi/200 μg/ml saline. Groups of 8 guinea pigs are anesthetized with ketamine (40 mg/kg) and xylazine (5 mg/kg) via s.c. injection and injected with radiolabelled LNT (about 1 μCi/kg) via the intracardiac route. A group of animals is sacrificed at 5, 15, 60, 120, 240 minutes and 24 hours post-dosing, a blood sample is obtained (2 ml) and the cerebrum, eyes, lungs, heart, stomach, duodenum, spleen, kidney, peritoneal fat pad, and testes are dissected and weighed. Animals in the last 3 groups are re-anesthetized prior to sacrifice if required. Tissues are homogenized in ground glass homogenizers with saline and counted in a gamma counter. The concentration of LNT is calculated in ng/g tissue as well as standard pharmacokinetic parameters for $t_{1/2}$ values, total body clearance, volume of distribution and area under the plasma concentration curve.

Results from this study could verify LNT exclusion in the guinea pig brain and eye tissue or indicate that there is some degree of penetration by the radiolabelled moiety and establish a baseline level of LNT that penetrates the intact BRB. Because previous studies in the rat have demonstrated the enzymatic stability of LNT, counts should reflect the amount of intact LNT in the tissue. The difference between tissue levels and radioactivity associated with blood is unlikely to be a major factor, since peptide is rapidly cleared from the systemic circulation. Demonstration that LNT is excluded from eye tissue would provide compelling evidence that the peptide is unable to penetrate the intact BRB and that the observed clinical effects may be attributed to peptide delivery through a damaged BRB.

A second study adapts RIA methods used to characterize the plasma and tissue LNT distribution profile in rats to guinea pigs. Tissues that have evidence of detectable LNT levels from the first study are evaluated in this phase to verify the estimates of tissue LNT levels and establish the extraction efficiency of peptide recovery from processed tissue samples. This aspect of study is important to establish analytical techniques that can quantify the amount of enhanced retinal delivery afforded by LNT-CDS. Dihydropyridines are not stable after radiolabelling with usual radioactive tracers including: $^{125}$I, $^{3}$H or $^{14}$C. This precludes direct comparison of unpackaged and packaged LNT using techniques outlined in the first study. The level of sensitivity required to monitor LNT delivery in retinal tissue cannot be achieved with traditional HPLC methods. However, RIA methods capable of measuring 50 pg/ml serum can be adapted to pooled guinea pig retinal tissue.

Groups of 8 guinea pigs are injected with unlabelled LNT (200 μg/kg) as outlined in the first study. Tissues are collected from animals sacrificed at 10 minutes and 60 minutes following LNT dosing and extracted for peptides following the methods developed in validation of the LNT antibody and RIA methods as provided by Dr. M. Foegh. Briefly, tissues are extracted with 5 volumes of methanol-acetic acid (180:1), centrifuged and the solvent is evaporated under nitrogen. The dried extract is dissolved in 0.1% trifluroacetic acid and chromatographed. The extract is injected onto a Nucleosil 5 μm-C18 column and eluted at a flow rate of 1 ml/min with a 30 minute linear gradient of 5–95 % where 0.1% trifluroacetic acid, 95% acetonitrile, 5% water is solvent B and 0.1% trifluoroacetic acid, 5% acetonitrile, 95% water is solvent A. Fractions are lyophilized and dissolved in RIA buffer. Recovery is >80% and assay sensitivity defined at 15% label displacement is capable of detecting 50 pg/ml from serum samples.

To further characterize the LNT distribution profile in the guinea pig retina, LNT is localized within the retina and brain using immunocytochemical techniques. Colloidal gold immunocytochemistry studies of LNT provide a direct morphological comparison of the passage of LNT across the BRB versus the BBB in the guinea pig. The technique enables visualizing retinal distribution of LNT peptide after packaged LNT administration. It offers a powerful analytical tool to differentiate brain and retinal LNT distribution afforded by LNT-CDS.

Animals are treated with unlabelled LNT (200 μg/kg) rather than $^{125}$I-LNT using the same design described for the first study above. Ocular tissue is fixed and processed as previously described. Controls for non-specific labeling include incubation with the secondary antibody only and incubation with antibody absorbed with LNT. Grids are examined by transmission electron microscopy both with and without staining with 2% aqueous uranyl acetate. Sources of antibodies are as follows: polyclonal rabbit anti-LNT antibody, IgG fraction (Henri Beaufour Institute, Washington, D.C.); goat anti-rabbit IgG labeled with colloidal gold (Jackson ImmunoResearch Laboratories, West Grove, Pa.). LNT immunolocalization may use intravitreal colchicine injection (10 kg/50 μl) 24 hours prior to sacrifice to enhance the intensity of detection by blocking the axonal transport as previously reported for somatostatin.

Pharmacokinetic analysis uses a previously published method. The sample size of 8 guinea pigs/group is based on variance reported in the rat and may be extrapolated to the larger guinea pig. Validation procedures for RIA adaptation to guinea pigs include establishing intra-assay co-efficient of variance based on high and low spiked sample quadruplicates and interassay variance is estimated from duplicate values of serum standard pools determined in at least 4 assays. All samples are assayed in duplicate. For histocytochemistry, semiquantitation of the localization of LNT is done from representative electron micrographs at a final magnification of 30,000× by two observers masked to the identity of the tissue origin. Colloidal gold particles are counted and final counts are expressed per unit area, as previously described. These quantitative studies are performed only on specimens which have been labeled at the same time using the identical reagents. Guinea pig retinas and brains from animals injected with saline are compared to retinas and brains of animals injected with LNT using the same aliquot of reagents. A minimum of 6 saline injected and 6 LNT injected retinas are analyzed. Mass spectral data analysis follows previous procedures to verify signal identities.

Assay sensitivity and instability of radiolabelled dihydropyridine compounds are the primary factors that necessitate a variety of analytical approaches to establish baseline LNT penetration values into retinal tissue of intact normal animals. RIA techniques are most sensitive and can detect values of less than 1 ng, while mass spectral analysis is at least 2 orders of magnitude less sensitive. It is fully expected that LNT is excluded from the ocular tissue due to the BRB. Therefore, recovery studies are designed to carefully validate extraction methods to collaborate the anticipated absence of measurable levels. Mass spectral data is used in in vitro processing studies where conditions can be modified to accommodate the level of assay sensitivity.

Additionally, somatostatin receptors in the retina are sensitive to anesthetics; however, both ketamine and sodium pentobarbital have been used by other investigators in studies examining the somatostatin receptor in the rabbit retina. The endogenous somatostatin of the retina is primarily in the ganglion cell layer where somatostatin receptor is present. Because the vascular component of the retina is anterior to the ganglion cells, high "background levels" of LNT binding to the somatostatin receptor are not anticipated in the areas of the retina in which immunocytochemistry is performed.

The next study aims to characterize the retinal enzymatic activity profile involved in oxidation of the T function and cleavage of the L and S functions used in molecular packaging for enhanced, sustained peptide delivery to retinal tissue.

The rationale for this aim is to test the ability of retinal tissues to accomplish retrometabolic processing required for enhanced sustained peptide delivery from the molecular packaging strategy. Characterizing possible differences in rates of T dihydropyridine oxidation or hydrolysis of L and S groups provides guidelines for selecting S functional group incorporation and prioritizing synthesis of several possible LNT-CDS compounds.

The stability of model packaged peptides is examined in guinea pig retina and brain homogenates and whole blood to characterize the enzymatic processing each of these tissues is likely to exert on critical components involved in targeted peptide delivery. Oxidation must precede hydrolysis in the molecular packaging strategy and the rate of hydrolysis must exceed the rate of peptide efflux from the tissue for sustained peptide delivery. This step utilizes robust HPLC analytical methods capable of detecting low ng quantities of peptide with routine UV detection procedures.

The model packaged peptides include the enkephalin and TRH analogs which have been studied in rat brain and blood and demonstrated centrally mediated sustained pharmacological activity that was greater than unpackaged peptide in rat models. Methods for examining retinal processing are adapted from routine methods used to examine metabolic profiles in brain homogenates. In these studies, guinea pig brain tissue is used exactly as described for rats, and guinea pig retinal tissue is similarly studied after pooling tissues from 5 animals to yield an adequate amount of tissue for study (85–100 mg).

In these studies, freshly obtained guinea pig brain is homogenized in a ground glass tissue grinder with phosphate buffered saline (pH 7.4) to produce 20% w/v homogenate. Heparinized guinea pig blood is used diluted with the same buffer to 40% v/v. The CDS peptide dihydropyridine compounds (30 μmol/100 mg tissue), dissolved in DMSO or ethanol/50% hydroxypropyl-β-cyclodextrin, are then added to each biological matrix (maintained at 37° C. in water bath). At various times after addition of the dihydrotrigonellinate, 100 μl of the homogenate or blood is removed, and rapidly mixed with an appropriate organic solvent, and an internal standard is added. Incubation methods for retinal tissue are scaled from 1 ml to 0.5 ml and 50 μl aliquots are assayed to accommodate the small tissue sample and reduce the number of animals required to 5/incubation.

For the highly lipophilic packaged compounds, the sample is shaken with 1 ml ice-cold methylene chloride/1-butanol (9/1, v/v), then centrifuged at 12,000 rpm (Beckman Microfuge 12). The organic layer is removed, and the extraction is repeated twice with 1 ml organic solvent. The combined organic fractions are evaporated to dryness. The residue is solubilized in the mobile phase and analyzed by HPLC (Spectra Physics SP 8810 precision isocratic pump, Rheodyne 7125 injection valve, SP 8450 variable wavelength UV/VIS detector and SP 4290 computing integrator). Normal-phase separation (25 cm×4.6 mm ID Lichrosorb Diol column, hexane/isopropanol/methanol eluent adjusted to the appropriate solvent strength) is better suited to the HPLC assay of the CDS's containing both T and L moieties (UV detection at 360 nm), because of their highly lipophilic nature, than the reversed-phase separation. In other cases, the sample is mixed with 400 $\mu$l ice-cold acetonitrile and centrifuged at 12,000 rpm. The supernatant is analyzed by reversed phase HPLC (5 cm×4.6 mm ID Supelcosil LC-18-DB or NOVAPACK Phenyl column, aqueous/organic eluent buffered and adjusted as necessary to obtain optimal separation conditions).

The next aspect of this step is adapting analytical methods used to measure enkephalin in tissue to quantify LNT levels from tissue. These studies adapt mass spectroscopy methods used to evaluate brain enkephalin profiles to retinal LNT profiles. Analytical procedures are established to characterize retrometabolic processing of packaged peptides in retinal tissue analogous to the procedures previously established for enzymatic processing in rat brain homogenates. This step is required for analysis of compounds in experiments outlined in other steps. Previous studies used 200 mg aliquots of rat brain tissue processed in pH 7.4 Tris buffer to yield 20% homogenates. Retina weight in guinea pigs is approximately 18 mg/animal (considerably larger than rats) mandating that pooled retinas must be used to prepare homogenates. Pooled retinal tissue from 5 guinea pigs is used for in vitro studies and methods previously described for analyzing peptide profiles are followed. Various amounts of packaged and unpackaged peptide are added to retinal homogenates as described in experiments above. Tissue homogenates are processed according to published methods.

Tissue homogenates (0.25 ml aliquots containing 20% (w/v) retina tissue) are processed by adding one volume of cold 1 M acetic acid and centrifuging the mixture. The supernatant is passed through Supelclean LC-18 cartridges. Poorly retained compounds are eluted with 3% acetic acid and the sample is eluted with 70% methanol in water containing 3% acetic acid. The solvent is removed under dry $N_2$ and reconstituted in 10 $\mu$l of a methanol:3% aqueous acetic acid solvent (50:50). The sample is analyzed by electrospray ionization mass spectrometry at a flow rate of 5 $\mu$l/min with a limit of detection of approximately 500 pM. The disappearance of the compounds is analyzed and enzyme kinetic models are used to determine the rate of loss as previously described. For the predicted oxidation and/or hydrolysis products, their rate of appearance will also be determined and correlated with the rate of disappearance of the compound under study. Should the kinetics not correlate, efforts are made to identify other decomposition products by mass spectrometry (using FAB and ESI) or LC-MS (ESI or thermospray/discharge/filament/chemical ionization available on the VESTEC ES 200A system).

Plasma protein binding is also examined in this phase of compound screening to provide an index of body distribution. Guinea pig plasma (1 ml) is spiked with various amounts of the compounds to give concentrations ranging from 500 to 2000 ng/ml. The plasma is then transferred to an Amicon centrifugal concentrator equipped with a low-adsorbance hydrophilic YM membrane with a 10,000 MW cutoff and centrifuged for 5 minutes at 6,000 rpm at 27° C. The filtrate is then extracted and analyzed by HPLC. The fraction bound ($F_b$) is calculated as:

$$F_b = (C_t - C_f)/C_t$$

where $C_t$ is the total drug concentration and $C_f$ is the unbound drug concentration.

Rabbit retinas have also been considered for study, since this animal species is included to test pharmacological action of the new compounds in the IGF-1 induced neovascularization models. However, it is suggested that the distribution studies be conducted in the guinea pig due to antibody considerations. While it is certainly possible that the retinal enzymatic processing varies considerably between species, little evidence is available to indicate fundamentally different roles for the retina between species. The purpose of studying model compounds is to guide design of LNT-CDS functional groups. After synthesizing the selected LNT-CDS compounds, they are examined for in vitro metabolism using the same procedures employed for the model CDS compounds which have previously been synthesized.

Studies to examine stability of the unmodified LNT are not necessary because the peptide is known to be stable and has been shown to be >90% excreted intact. However, the identification of the peptidolytic products of modified packaged peptide is an aspect of this phase. The method is based principally on the extensive use of the state-of-the-art mass spectrometric techniques, FAB and ESI. In order to remove inorganic contaminants adversely affecting these desorption ionization techniques, ion-exchange chromatography (disposable Supelclean SCX minicolumns) is applied. The supernatant from the centrifuged samples is transferred through the cartridges at 1 droplet/s rate, and the column is washed with slightly acidified (weak acid) acetonitrile. This procedure does not affect the weak quaternary pyridinium cations. The solvent from the eluate is evaporated under nitrogen stream. (This may not be necessary for the very sensitive electrospray ionization). FAB mass spectra is recorded (KRATOS MS80RFA sector instrument, saddle-field xenon gun operated at 6–8 keV particle energy, mostly 3-nitrobenzyl alcohol matrix). Continuous-flow (dynamic) FAB technique is used, if and when suppression of the sputtering of lipophilic peptides is observed. Alternatively, the sample solution is "infused" at a rate of 5–10 $\mu$l/min into an electrospray ion source of the mass spectrometer (VESTEC ES 200A quadrupole instrument). Should LC-MS be necessary for separation of complex mixtures, packed microcolumns (10 cm×0.32 or 0.5 mm ID, octadecyl silica packing) are applied. For gradient elution, a conventional isocratic HPLC (Spectroflow 4000) pump with low-pressure solvent mixer (Spectroflow 430) and a dynamic balance column (10 cm×4.6 mm ID HPLC column) are applied to achieve the required 5–10 $\mu$l/min flow rate. Injections are made by a Valco C4W valve with 0.5 $\mu$l internal loop. For isocratic separations, a syringe pump (ISCO 260D) is used which delivers a pulseless flow of mobile phase down to 1 $\mu$l/min. Identifying the degradation product structures provides insights on: (a) the possible sites of peptide cleavage; (b) the enzymes responsible for cleaving the peptide; (c) the relative importance of the individual cleavage reactions; and (d) delivery of the peptide to the site of action.

Design and synthesis of chemical delivery systems (CDS) for the somatostatin analog LNT using the molecular packaging approach produces the new LNT-CDS moieties in order to test the enhanced delivery afforded to retinal tissue in normal guinea pigs. Design, synthesis, and stability in experimental formulations are the primary components for this phase of the proposal.

The rationale for selecting specific LNT-CDS moieties to synthesize is based on optimizing retinal penetration and sustained peptide delivery without pharmacologically significant drug concentrations occurring in the central nervous system. Since the retina is reported to be more permeable to amino acids as well as other compounds, rapid oxidation relative to the CDS developed for enkephalin should facilitate delivery. Evidence summarized above indicates that significant metabolic differences distinguish the BBB and BRB which support the less restrictive barrier action of the retina endothelium and pericytes compared to protection afforded the brain.

Structure activity studies predict that LNT is more potent in inhibiting angiogenesis compared to the natural somatostatin tetradecapeptide. This potency has been confirmed in the chick chorioallantoic membrane assay for angiogenesis. Structure activity relationship studies demonstrate the importance of lysine in position 5 and the cyclic structure formed by 2 cysteine residues that serves to orient the lysine side amino function in the proper configuration for potent angiogenic inhibition.

The representative synthetic procedures discussed below, as well as those depicted in the SCHEMES and the EXAMPLES which follow, utilize only the trigonellinate$\rightleftharpoons$1,4 dihydrotrigonellinate T function shown in formula (Ia) above and throughout the Schemes and Examples. Several other redox moieties are contemplated; however, the neurotoxicity of the selected T function has been extensively studied and clinical trials have been conducted that used this redox targetor. This particular T functional group has been selected to mimic the endogenous $NAD(P)^+\rightleftharpoons NAD(P)H$ interconversion. Early studies have indicated that the cleaved trigonelline group is readily excreted from brain tissue. Toxicity studies in rodents and primates have demonstated that a CDS which utilized the 1,4-dihydrotrigonelline T moiety was safe for clinical exploration.

The bulky, lipophilic L segment selected initially will be derived from cholesterol or adamantaneethanol, or from cortienic acid or $\Delta^1$-cortienic acid. The 17-OH positions of the latter two functions are protected from possible dehydration by using the methyl ether. The selection of these L elements has considered the safety profile of the lipophilic groups. The cholesteryl and adamantaneethyl functions give rise in vivo to the inactive and practically non-toxic lipophilic alcohols, while the other preferred functions are derivatives of the inactive and non-toxic metabolites of hydrocortisone.

The S groups initially contemplated are Pro-Pro, Ala-Ala, Pro-Ala and Ala-Pro. Results from the TRH compounds have suggested that prolyl endopeptidase could be involved in optimizing LNT release. Alternatively, carboxypeptidase B-like activity could help optimize LNT delivery. Attachment of basic amino acid pairs (Lys-Lys, Lys-Arg, Arg-Arg) is possible; however, inclusion of these sequences into the CDS molecules is synthetically more demanding.

Compound design also involves theoretical calculations that concentrate on specific parts of the entire molecule to elucidate the incremental changes resulting from T, L or S modification. These calculations help predict whether a particular LNT peptide structure is adequately protected for retinal delivery.

CDS components are subjected to geometry and energy optimization using molecular mechanics (MM2), and the AM1 and other available (MNDO) semiempirical methods. These calculations are now routine with CAChE computers and software. A MicroVAX can also be employed. The obtained optimum geometries and molecular properties data also are used to calculate lipophilicities (partition properties–log P, and aqueous solubilities–log W). The calculated values are compared with experimental log Ps. The optimized geometries are also used to calculate molecular volumes (V), molecular surfaces (S) and dipole moments (D) using numeric integration techniques based on dividing the molecules into cubic grids and setting up criteria for summation of the atomic contributions. The molecular descriptors, V, S, D, log W and log P, are compared to values obtained with the unmanipulated LNT to estimate the likely susceptibility of new compounds to peptidase cleavage.

Three structural features of LNT are to be considered in the synthesis of redox-based CDS moieties. The first is protecting the lysine amino side group. The second consideration is whether or not to protect the threonine hydroxy group. The third is protecting the disulfide bond during reduction of the quaternary T functional group in the final synthetic reduction step. Specific procedures to address these factors are considered in the following paragraphs.

If chemical considerations preclude direct modification of commercially produced LNT, synthesis of the packaged LNT-CDS can start with the L functional groups and sequentially add amino acid residues from the amide terminus of LNT. In this case, solid phase synthesis routinely used for peptide synthesis is not readily applied to molecular packaging of LNT. The quaternary pyridinium T group is then added, and the disulfide bonds are formed to cyclize the peptide. The final synthetic step is reducing the quaternary pyridinium to a dihydronicotinate. Solid phase synthesis can be used for the analytical internal standards that are critical in showing that the L group is hydrolyzed in both in vitro and in vivo studies.

Results from the in vitro studies guide the S group selection. No systematic evaluation of retinal tissue metabolism has previously been conducted on redox-based CDS moieties. Therefore, several CDS's will be evaluated including the enkephalin and TRH packaged peptide CDS's that are available and the new LNT-CDS moieties.

LNT-CDSs are synthesized by a solution-phase, sequential deprotection-coupling procedure based on the Fmoc chemistry which is compatible with more gentle resin cleaving conditions required for the LNT peptide that contains lysine, threonine and a cysteine bridge compared to the t-butoxycarbonyl (BOC) chemistry previously reported.

The synthetic procedures generally involve the following specific methods:

Procedure 1—Synthesis of lipophilic esters of amino acids: The C-terminus $—CONH_2$ present in LNT prevents direct coupling of cholesteryl to the peptide backbone since hydrolysis to carboxylic acid is the first step in synthesis. This problem is circumvented by incorporating glycine that can function as an amide donor due to action of peptidyl glycine a-amidating monooxyygenase (PAM) that is present in brain tissue and is expected to be similarly processed in retinal tissue.

For synthesis, 0.02 mmol cholesterol (7.62 g) or equimolar amount of adamantaneethanol, 0.028 mmol 4-dimethylaminopyridine (3.41 g) and 0.028 mmol Fmoc-protected glycine are dissolved in 200 ml of chloroform. To this mixture, 0.028 mmol (5.77 g) of N,N'-dicyclohexyl carbodiimide (DCC) is added and the reaction is carried out at room temperature for 48 hours. Then the reaction is stopped by adding a few drops of dilute acetic acid and the precipitated dicyclohexylurea (DCU) is filtered off. The chloroform solution is washed successively with aqueous 0.1 N citric acid solution three times, with sodium bicarbonate (5% w/v) solution three times, and finally with water. The chloroform solution is dried over anhydrous magnesium sulfate and evaporated to dryness. The compound is isolated by passing the crude product through a silica gel column using a mixture of hexane and chloroform as an eluent. The purity of the compound is routinely determined by thin-layer chromatography (TLC; silica gel plate using chloroform as an eluent, and the spots are visualized after spraying with 50% (w/w) sulfuric acid and the plate is kept at 120° C. for 5 minutes.

Procedure 2—Obtaining amino acid ester hydrochloride: The compound obtained from the above reaction is dissolved in 100 ml of methylene chloride and the solution is cooled down to 0° C. (ice bath). Thirty ml of anhydrous trifluoroacetic acid is then added, and the reaction mixture is allowed to stand for 30 minutes at 0° C. Then the cooling is removed, and after 30 minutes at room temperature, the solution is evaporated to dryness under reduced pressure. The residue is dissolved in 50 ml of methylene chloride, and again evaporated to dryness. This procedure is repeated three times to remove the excess of trifluoroacetic acid. The oily material is dissolved in 50 ml of anhydrous ether and neutralized with 1.9 ml of triethylamine at 0° C. An equivalent amount of hydrochloric acid in anhydrous ether is added to this solution and the precipitated hydrochloride salt is separated by decanting the supernatant. After washing several times with anhydrous ether, the remaining solvent is then evaporated under reduced pressure resulting in an amorphous powder.

Procedure 3—Coupling of Fmoc-threonine to an amino acid ester hydrochloride: The compound obtained from the above reaction is dissolved in 40 ml of methylene chloride and the solution is cooled down to 0° C. Triethylamine (18.04 mmol; 1.82 g) in 10 ml of methylene chloride, 1.99 g of hydroxybenzotriazole in 15 ml of anhydrous dimethylformamide (DMF), 13 mmol of Fmoc-protected threonine in 20 ml of methylene chloride and 2.68 g of DCC in 20 ml of methylene chloride are added to the mixture, respectively. The solution is stirred for 1 hour at 0° C., then the cooling is removed. The stirring is continued overnight at room temperature. The reaction is stopped by adding a drop of dilute acetic acid, the precipitated DCU is filtered off, and the solvent is evaporated to dryness in vacuo. The residue is dissolved in 100 ml of chloroform and washed several times with sodium chloride solution, 0.1 N citric acid, 7% sodium bicarbonate solution and with a saturated solution of sodium chloride, respectively. The organic layer is dried over magnesium sulfate and evaporated to dryness. The TLC of the compound (chloroform: methanol, 96:4) usually indicates the presence some unreacted compound, the Fmoc-amino acid, and some very non-polar compound. The target compound is obtained by column chromatography (silica gel) using chloroform:methanol (96:4, v/v) mixture as an eluent.

Procedure 4—Removing the Fmoc protecting group: The Fmoc group is removed using trifluoroacetic acid, and then the product is converted to the hydrochloride salt, as described under Procedure 2. The peptide hydrochloride salt is then coupled to another Fmoc amino acid according to Procedure 3. The deprotection and coupling steps are continued until the desired peptide is obtained.

Procedure 5—N-terminal acylation of the peptide: The hydrochloride salt of the deprotected peptide (Procedure 4) is coupled to the acid as described under Procedure 2. (Obviously, the Fmoc-protected amino acid is substituted with an equimolar amount of acylating agent such as nicotinic acid, or 4,4-dimethyl-1,4-dihydrotrigonellic acid—introducing the suggested non-oxidizable control group).

Procedure 6—Quaternization of the nicotinoyl peptide: The nicotinoyl peptide obtained according to the above procedure is dissolved in dimethylformamide and two equivalents of dimethylsulfate are added. The reaction mixture is stirred at room temperature overnight. The compound is isolated by evaporating the solution in vacuo, washing several times with anhydrous ether and purifying by precipitating from a methanol-ether mixture.

Procedure 7—Reduction of the quaternary pyridinium salt to 1,4-trigonellinate: The trigonellinate is dissolved in a mixture of degassed water and methanol (4:1). N-benzyl 1,6-dihydroisonicotinamide (1-benzyl-1,2-dihydroisonicotinamide) is used to function as a hydride donor at 0° C. in methanol to reduce the pyridine ring as previously described for an alkylamine. To this solution, six equivalents of sodium bicarbonate and four equivalents of N-benzyl 1,6-dihydroisonicotinamide are added, and the mixture is cooled down to 0° C. The reaction is allowed to proceed at 0° C. for 2 hours under nitrogen atmosphere. The dihydro derivative is isolated by extracting the reaction mixture with methylene chloride. The organic layer is dried over magnesium sulfate and evaporated to dryness under reduced pressure.

Preformulation solubility and stability profiles are examined. Pharmaceutically acceptable vehicles are emphasized including ethanol, propylene glycol and various lipids. Additionally, incorporation in modified cyclodextrins, especially aqueous parenteral formulations of modified cyclodextrins, will be examined, as discussed in more detail hereinbelow.

The sequence of reactions is carried out under careful analytical control. While TLC is obviously the method of choice for routine synthesis monitoring, FAB and electrospray mass spectrometry, combustion analysis, and high-performance liquid chromatography (and LC-MS) are used to confirm the structure, identify the contaminants, and determine the purity of the samples. It is then decided if and when additional separation steps are necessary to prevent extensive carryover of contaminants ultimately affecting the purity of the target compound. The purification is done by semi-preparative HPLC. Reversed-phase conditions (octadecyl silica cartridge system, SP 8810 preparative HPLC pump, 0.01–0.1% (v/v) aqueous trifluoroacetic acid solution containing acetonitrile as organic modifier) are applied to obtain pure intermediate compounds. The final stage of purification, if necessary, is immediately before the reduction step; usually no further clean-up can be expected, once the 1,4-dihydrotrigonellinate is obtained. This is due to the limited oxidative stability of the dihydropyridine compounds.

For both the chemical characterization procedures and the in vitro metabolism studies, key fragments as well as the parent LNT will be required. While the LNT will be available, the $T^+$ (S)LNT and other intermediates can be made by automated solid-phase peptide synthesis. The first amino acid is coupled to the appropriate resin, and the successive deprotection-coupling reactions are carried out with the resin-bound peptide. Finally, the peptide is cleaved from the resin with hydrogen fluoride, and the product is purified, if necessary, by semi-preparative HPLC. Efforts are made to develop methods that allow for "assembling" target compounds from fragments that already contain given numbers of amino acid residues. This considerably increases synthetic productivity, since building up peptide chains can be done in parallel. The yield also increases.

The new LNT-CDS derivatives are compared with the unpackaged LNT in terms of distribution and pharmacological activity by: (a) characterizing metabolism in vitro to verify that oxidation precedes hydrolysis in retinal tissue; (b) comparing the distribution profile of LNT-CDS to unmodified LNT in vivo in guinea pigs; and (c) assessing the pharmacological activity of LNT-CDS in a rabbit model of growth factor-induced ocular neovascularization.

Methods used here to evaluate the degree of improved LNT delivery to retinal tissue are the same procedures described above. The pharmacological activity is tested in the rabbit model of IGF-1 induced neovascularization that is described above. This model is capable of directly evaluating the magnitude of growth factor inhibitor activity in retinal tissue.

The first studies to be conducted with newly synthesized LNT-CDS compounds should verify that oxidation precedes hydrolysis in retinal tissue homogenates using procedures identical to those described hereinabove. These in vitro studies must also demonstrate that free LNT is generated in retinal homogenates. Mass spectrographic methods are used to quantify the amount of LNT generated in retinal homogenates. Sample preparation procedures are identical to those already described above.

The second aspect of study for new packaged LNT compounds examines the in vivo distribution of LNT in blood, retina and brain tissues after LNT or LNT-CDS administration. RIA procedures validated for earlier studies described above are used to quantify the amount of LNT peptide delivered over time. Study design includes groups of 8 guinea pigs injected with 200 $\mu$g/kg unpackaged LNT or equimolar LNT-CDS. Vehicle selected is the formulation identified above which is capable of solubilizing at least an amount of LNT-CDS equimolar to 50 $\mu$g/ml unpackaged LNT. A preferred vehicle is ethanol and aqueous hydroxypropyl-$\beta$-cyclodextrin with small amounts of dimethylsulfoxide added if required. Another preferred formulation is aqueous hydroxyalkylated $\beta$- or $\gamma$-cyclodextrin solution, especially 20–50% aqueous cyclodextrin solution. Animals are sacrificed at 5, 15, 60, 120, 240 and 480 minutes and 24 hours following drug administration and tissues are collected and processed to extract LNT as described hereinabove. Assay sensitivity levels of 0.05 ng should be adequate to detect LNT in the early time points and may detect retinal concentrations at the late time points.

Immunohistocytochemistry offers the ability to localize the distribution of LNT within retinal tissue and may offer an increased level of detection sensitivity. Anesthetized guinea pigs receive a single intracardiac injection of LNT or LNT-CDS (200 $\mu$g/kg) in the same vehicle selected for the above distribution study. Groups of animals (n=8) are sacrificed at 5, 15, 60, 120 and 480 minutes and 24 hours following drug injection and retinal tissue is processed to visualize immunoreactive LNT using immunohistochemical methods developed as described hereinabove. Specifically, ocular tissue is fixed and processed as previously described. Controls for non-specific labeling include incubation with the secondary antibody only and incubation with antibody absorbed with LNT. Grids are examined by transmission electron microscopy both with and without staining with 2% aqueous uranyl acetate. Sources of antibodies are as follows: polyclonal rabbit anti-LNT antibody, IgG fraction (Henri Beaufour Institute, Washington, D.C.); goat anti-rabbit IgG labeled with colloidal gold (Jackson ImmunoResearch Laboratories, West Grove, Pa.).

Semiquantitative localization of LNT is done from representative electron micrographs at a final magnification of 30,000× by two observers masked to the treatment group. Colloidal gold particles are counted and final counts are expressed per unit area. These quantitative studies are done only on specimens which have been labeled at the same time using the identical reagents. Guinea pig retinas and brains from animals injected with LNT are compared to retinas and brains of animals injected with equimolar LNT-CDS using the same aliquot of reagents. A minimum of 6 LNT injected and 6 LNT-CDS injected retinas are analyzed. A vehicle control is not included as no differences are expected between vehicle and LNT treatments.

Pharmacological activity compares the effects of LNT and LNT-CDS in the newly developed rabbit model of IGF-1 induced neovascularization. Methods for inducing neovascularization are identical to those previously published. Briefly, pigmented rabbits (n=18) are anesthetized with ketamine and pupils are dilated with topical tropicamide 0.25% and phenylephrine 0.5%. An 80 $\mu$l aliquot of fluid is withdrawn from the anterior eye chamber via a 27 g needle and a 30 g needle is inserted through the sclera and retina 4 mm posterior to the corneoscleral junction in the supertemporal quadrant of one eye. Under stereomicroscopic control, the bevel of the needle is directed up and 600 $\mu$g of IGF-1 is injected in a saline solution (0.1 ml) directly over the optic nerve head. Animals undergo fundus photography and fluorescein angiograms every second day for 2 weeks and on day 21 post-IGF-1. Groups of 6 animals are treated with vehicle, LNT or LNT-CDS daily at a dose equimolar to 100 $\mu$g/kg of LNT beginning on the day of IGF-1 treatment.

Animals are sacrificed on day 21 post-IGF-1, eyes are enucleated and small slits made at the scleral-limbal junction prior to placing the eyes in Trump's fixative. Collates are cut along the meduallary rays to include the optic disc and washed in potassium phosphate-sodium hydroxide buffer and post-fixed overnight in 1% buffered osmium tetroxide. Specimens are dehydrated through graded ethanol baths to a propylene oxide bath, infiltrated, and embedded in epoxy resin. Ultrathin sections are then post-stained with 2% aqueous uranyl acetate followed by Reynolds lead citrate, examined and photographed by transmission electron microscopy at an accelerating voltage of 75 KV.

The first studies evaluate oxidation and hydrolytic processing of the LNT-CDS using standard evaluation techniques to identify disappearance and appearance of metabolites. The second studies compare the amounts of immunoreactive LNT measured in tissues after treatment with LNT-CDS or LNT. Eight animals are injected with LNT and another eight animals with the packaged LNT-CDS. It is anticipated that retinal tissue levels of unpackaged LNT will be below detection limits in all 8 animals. With this sample size, a convincing demonstration of transport across the BRB (p=0.005) can be obtained with a two-sided Wilcoxon rank-sum test with continuity correction (1, p6), even if 2 of the retinal levels after LNT-CDS are below detection limits. A marginally significant result (p=0.05) can be obtained when half of the animals have detectable LNT. When LNT-treated brain and retinal samples are below assay detection limits, as expected, non-parametric statistics can be used to evaluate the significance of measured differences between treatment. Treatment related differences in the pharmacological study afforded by packaged and unpackaged LNT on induced ocular neovascularization can be evaluated by several methods. Of particular relevance is the classification of each retina into one of four severity categories for neovascularization. Micrographs are rated by masked comparison to a set of standards, and the effect of packaging is evaluated using a Wilcoxon test. The power of the test is approximated by that of Student's t-test. Scoring the categories as 0, 1, 2, or 3, a mean difference of 1 is physiologically meaningful and well defined by the reference micrographs. It is expected that the response to unpackaged LNT will resemble the IGF-1 plus vehicle control treated model of neovascularization, with the responses divided about equally between the highest scores of 3 and 4, with a standard deviation of 0.5. Doubling the variance, to allow for variation in delivery of LNT-CDS yields a standard deviation of 0.71 which is used to estimate power.

The "packaged" peptides of formula (I) provided by the present invention are typically administered to a mammal, particularly a human, dog or cat, any of which is intended to be encompassed by the term "patient" herein, in need of the prevention or treatment of diabetic retinopathy, by incorporating the selected "packaged" peptide in a pharmaceutical composition comprising a compound of formula (I) or a non-toxic pharmaceutically acceptable salt thereof and a non-toxic pharmaceutically acceptable carrier therefor. The packaged peptide or its salt is employed in an effective amount i.e. an amount sufficient to evoke the desired pharmacological response. This is generally an amount sufficient to produce lessening of one or more of the effects of diabetic retinopathy. Preferably, it is an amount sufficient to produce regression of neovascularization and/or an amount sufficient to produce improved visual acuity. Since the compounds of the invention are preferably delivery systems for somatostatin analogs, they are typically used to provoke the type of pharmacological response which would be achieved if the peptides which they are designed to deliver were to be administered directly to the retina.

Suitable non-toxic pharmaceutically acceptable carriers for use with the selected peptide derivative of formula (I) will be apparent to those skilled in the art of pharmaceutical formulation. See, for example, *Remington's Pharmaceutical Sciences,* seventeenth edition, ed. Alfonso R. Gennaro, Mack Publishing Company, Easton, Pa. (1985). Obviously, the choice of suitable carriers will depend upon the exact nature of the particular dosage form selected, as well as upon the identity of the "packaged" peptide to be administered. The therapeutic dosage range can be estimated on the basis of animal tests. Naturally, such therapeutic dosage ranges will vary with the particular compound of formula (I) used, the size, species and physical condition of the subject, the severity of the subject's medical condition, the particular dosage form employed, the route of administration and the like. And the quantity of given dosage form needed to deliver the desired dose will of course depend upon the concentration of the "packaged" peptide of formula (1) in any given pharmaceutical composition/dosage form thereof. Generally speaking, on a molar basis, the dosage levels of the "packaged" peptides needed to provoke the desired pharmacological response will be much lower than those needed of the corresponding "unpackaged" peptides.

In addition, a route of administration may be selected to slowly release the chemical, e.g., slow intravenous infusion.

At the present time, it is believed that parenteral administration, especially intravenous administration, is the desired route of administration appropriate for the compounds of formula (I) and pharmaceutical compositions containing them. Parenteral dosage forms should be sterile and pyrogen-free, and are prepared in accord with accepted pharmaceutical procedures, for example as described in *Remington's Pharmaceutical Sciences,* seventeenth edition, ed. Alfonso R. Gennaro, Mack Publishing Company, Easton, Pa. (1985), pp. 1518–1552. The parenteral formulations may be organic or aqueous or mixed organic/aqueous formulations and may further contain anti-oxidants, buffers, bacteriostats, isotonicity adjusters and like additions acceptable for parenteral formulations. In a preferred embodiment, the parenteral formulation contains an effective amount of compound of formula (I) in an aqueous solution containing from about 20% to about 50% cyclodextrin selected from the group consisting of hydroxypropyl, hydroxyethyl, glucosyl, maltosyl and maltotriosyl derivatives of β- and γ-cyclodextrin, preferably of hydroxypropyl-β-cyclodextrin. Parenteral formulations of this type for administration of lipophilic and/or water-labile drugs are described in U.S. Pat. Nos. 4,983,586 and 5,024,998 and their foreign counterparts, for example, European Patent No. 0335545, all of which are incorporated by reference herein in their entireties and relied upon.

Methods for synthesizing the packaged peptides of the present invention have already been discussed hereinabove, and are shown in detail in the SCHEMES and EXAMPLES which follow. These Schemes and Examples are for the purpose of illustration only, as many modifications of materials, methods and reaction sequences will be apparent to those of ordinary skill in the art.

In one specific preferred embodiment of the present invention, molecular "packaging" has been used for octreotide (SCHEME I and EXAMPLES 1–6) in order to circumvent both the physical blood retinal barrier and the enzymatic blood retinal barrier and deliver the peptide to the retina by sequential metabolism. In the case of the trigonellinate intermediate, it is of course the quaternary cation, not necessarily the particular salt thereof shown in the EXAMPLES, which is found in vivo; the anion may be any anion present in vivo.

In SCHEMES I through IX and the EXAMPLES which follow, abbreviations generally follow IUPAC-IUB recommendations as published in *J. Biol. Chem.* 264, 668–643 (1989). Other abbreviations are set forth below. All amino acids are L-configuration except as otherwise indicated. Abbreviations follow the recommendations of the IUPAC-IUB Commission on Biological Nomenclature as given in *Eur. J. Biochem.* 138, 9–37 (1964).

| TEA | triethylamine |
|---|---|
| BocN$_3$ | tert-butoxycarbonylazide |
| HOAC | acetic acid |
| DIEA | N,N-diisopropylethylamine |
| Fmoc | 9-fluorenylmethyloxycarbonyl |
| DMF | dimethylformamide |
| PyBOP | benzotriazole-1-yl-oxy-tris-pyrrolidino-phosphonium hexafluorophosphate |
| DMA | dimethylacetamide |
| TFE | trifluoroethanol |
| TFA | trifluoroacetic acid |
| HOBt | 1-hydroxybenzotriazole |
| DIC | dissopropylcarbodiimide |
| Et | ethyl |
| EtOEt | diethyl ether |
| MeCN | acetonitrile |
| EtOAc | ethyl acetate |
| DCCI | dicyclohexylcarbodiimide |
| Boc | tert-butoxycarbonyl |

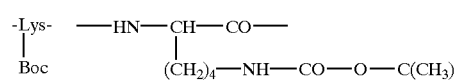

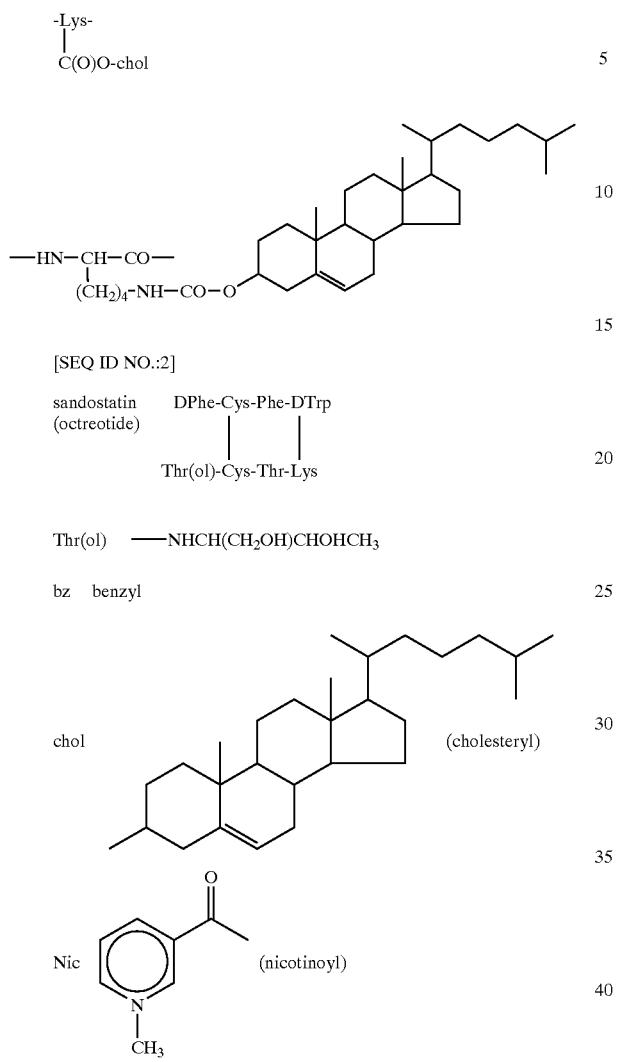
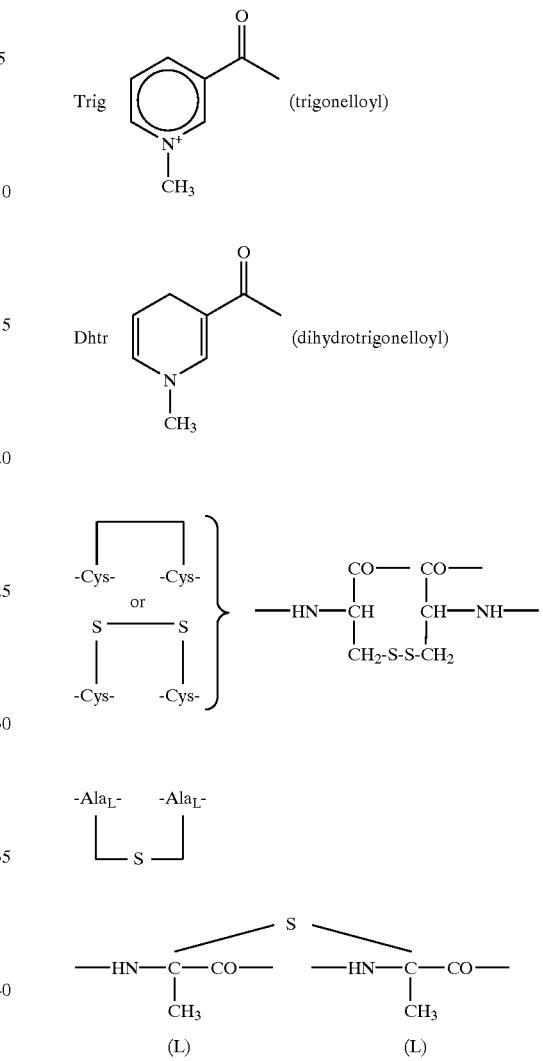
SCHEME 1
Synthesis of octreotide-CDS₁
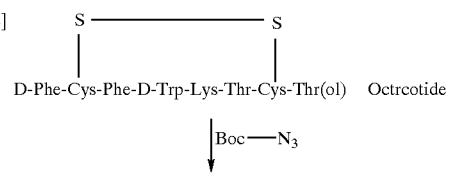

-continued

[SEQ ID NO.: 8]
```
        S ——————— S
        |         |
D-Phe-Cys-Phe-D-Trp-Lys-Thr-Cys-Thr(ol)
            |
            Boc
```

↓ Nic-Pro-Pro-OH (as benzotriazole ester)

[SEQ ID NO.: 9]
```
                    S ——————— S
                    |         |
Nic-Pro-Pro-D-Phe-Cys-Phe-D-Trp-Lys-Thr-Cys-Thr(ol)
                        |
                        Boc
```

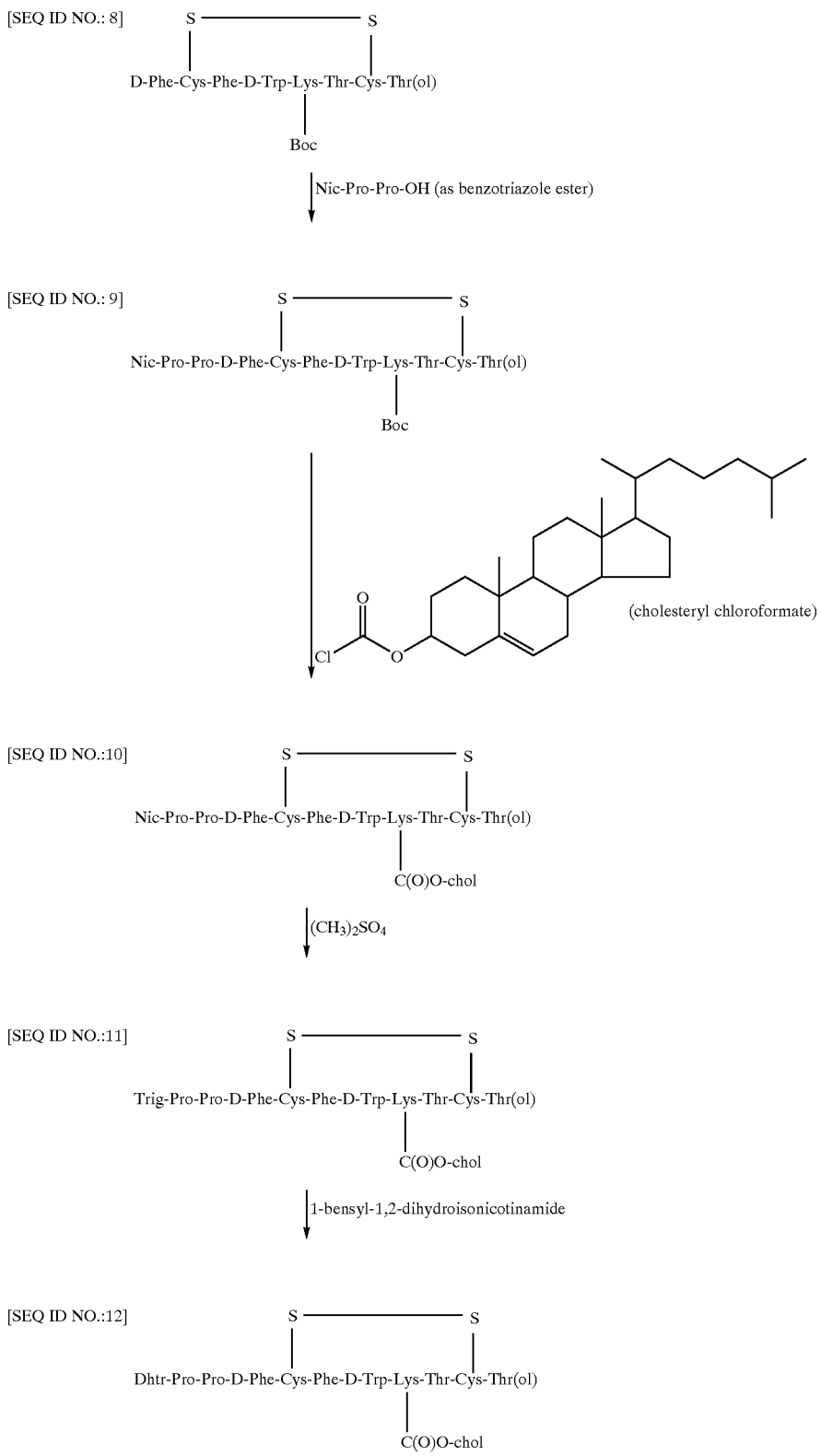

(cholesteryl chloroformate)

[SEQ ID NO.:10]
```
                    S ——————— S
                    |         |
Nic-Pro-Pro-D-Phe-Cys-Phe-D-Trp-Lys-Thr-Cys-Thr(ol)
                        |
                        C(O)O-chol
```

↓ (CH$_3$)$_2$SO$_4$

[SEQ ID NO.:11]
```
                    S ——————— S
                    |         |
Trig-Pro-Pro-D-Phe-Cys-Phe-D-Trp-Lys-Thr-Cys-Thr(ol)
                        |
                        C(O)O-chol
```

↓ 1-bensyl-1,2-dihydroisonicotinamide

[SEQ ID NO.:12]
```
                    S ——————— S
                    |         |
Dhtr-Pro-Pro-D-Phe-Cys-Phe-D-Trp-Lys-Thr-Cys-Thr(ol)
                        |
                        C(O)O-chol
```

The trigonellinate quaternary salt predecessor of the CDS can also be represented as follows:

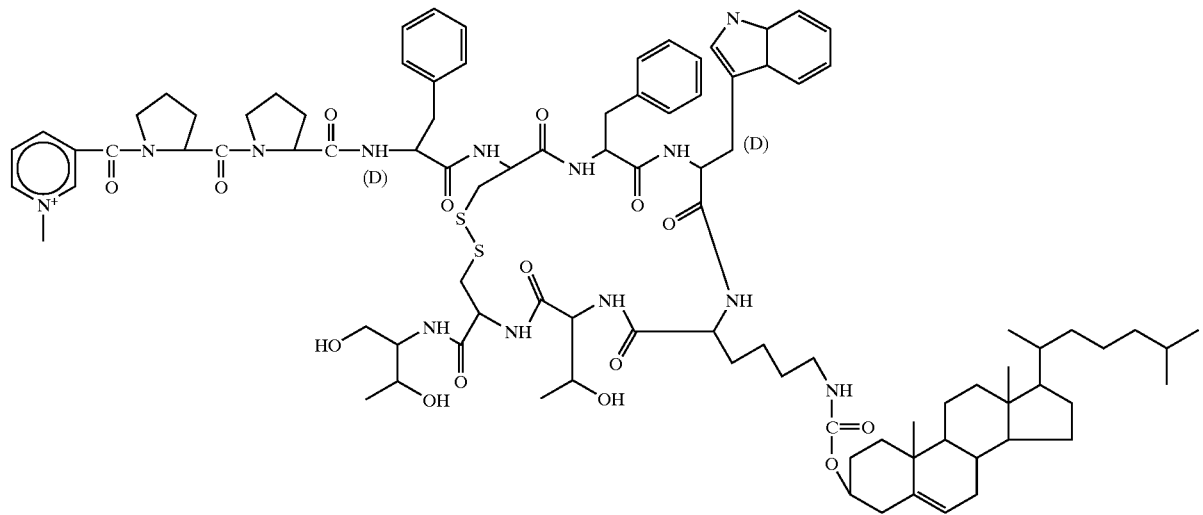

The final product, octreotide-CDS$_1$, can also be represented as follows:

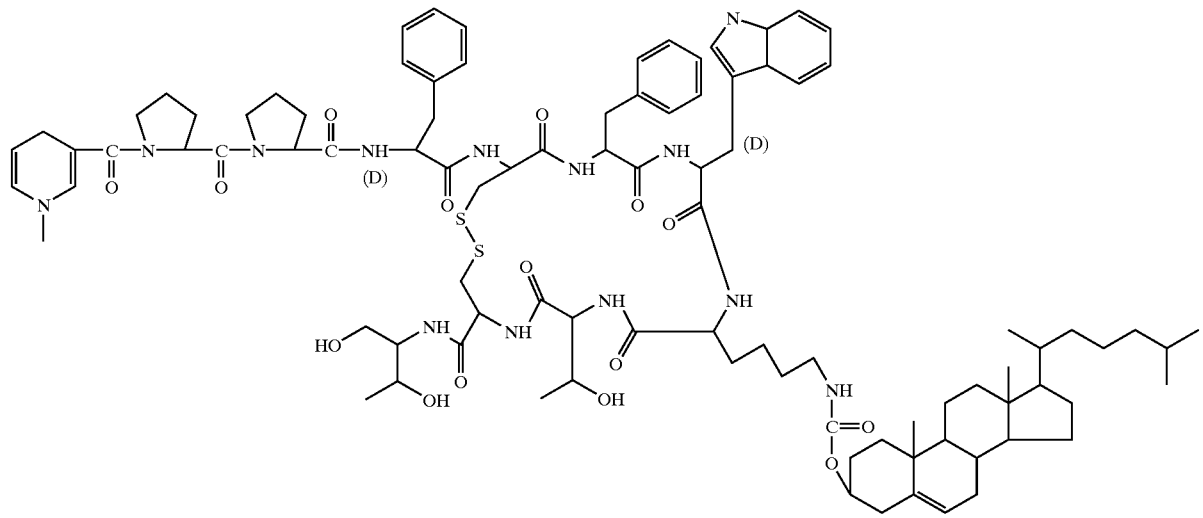

The process of SCHEME I is described in more detail in EXAMPLES 1–6 hereinafter.

Repetition of the steps of SCHEME I utilizing Nic-Ala-Ala-OH (as the benzotriazole ester) in place of the Nic-Pro-Pro-OH (as the benzotriazole ester) reactant and otherwise proceeding as above affords, in the reaction with dimethylsulfate,

[SEQ ID NO.: 13]

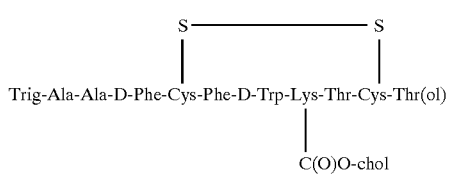

and, after reduction, the octreotide-CDS$_2$,

[SEQ ID NO.: 14]
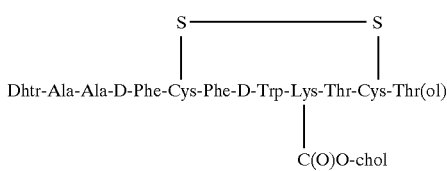

Repetition of the steps of SCHEME I, but substituting adamantaneethyl chloroformate (prepared from adamantaneethanol and phosgene) for the cholesteryl chloroformate used there affords, after the quaternization reaction,

[SEQ ID NO.: 15]
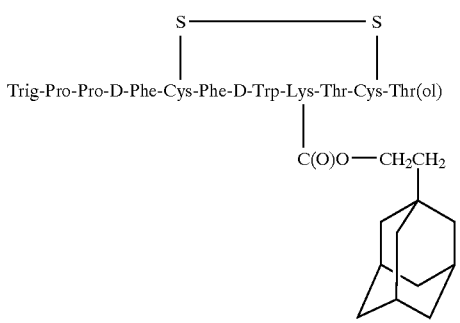

and, after reduction, the octreotide-CDS$_3$,

[SEQ ID NO.: 16]
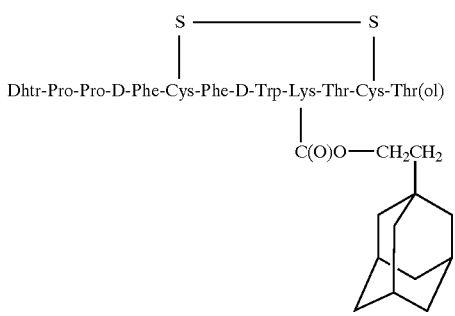

SCHEME II
Synthesis of octreotide analog #1-CDS$_1$

[SEQ ID NO.: 4]
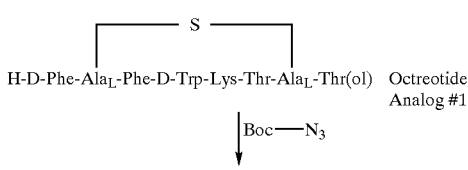  Octreotide Analog #1

[SEQ ID NO.: 17]
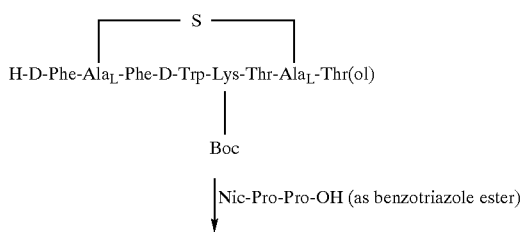

[SEQ ID NO.: 18]
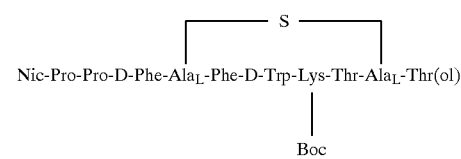

[SEQ ID NO.: 19]
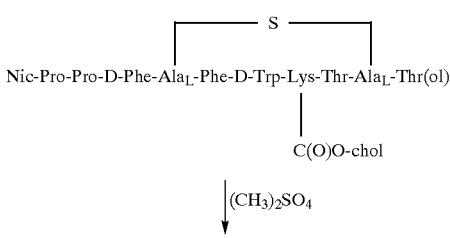

[SEQ ID NO.: 20]
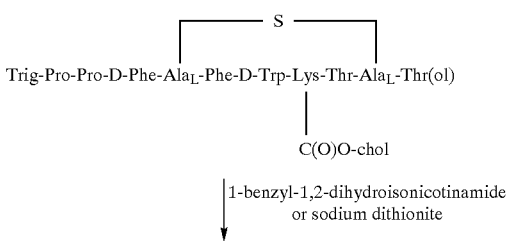

[SEQ ID NO.: 21]
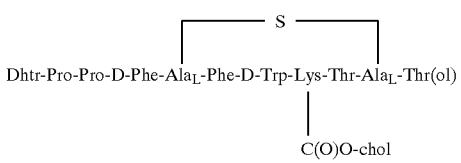

Scheme II can be modified to introduce other spacers, for example -Ala-Ala-, and/or to utilize a different R$_4$ group, for example adamantaneethyl rather than cholesteryl, as described with Scheme I above.

SCHEME III
Synthesis of lanreotide-CDS$_1$
[SEQ ID NO.: 3]
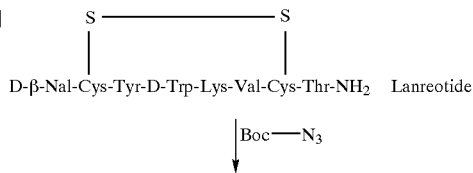
Lanreotide
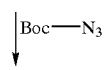
Boc—N$_3$
[SEQ ID NO.: 22]
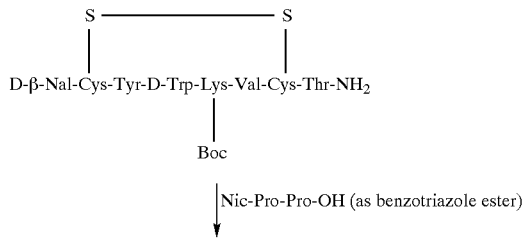
Nic-Pro-Pro-OH (as benzotriazole ester)
[SEQ ID NO.: 23]
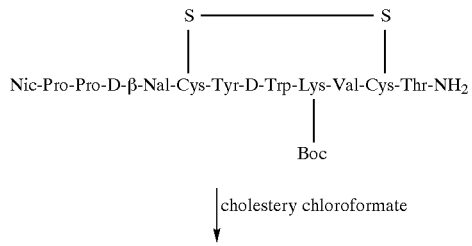
cholestery chloroformate
[SEQ ID NO.:24]
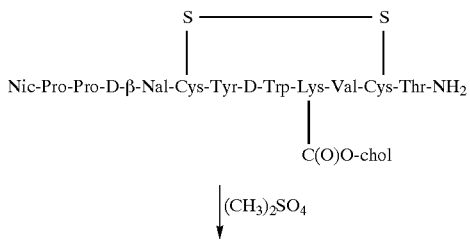
$(CH_3)_2SO_4$
[SEQ ID NO.:25]
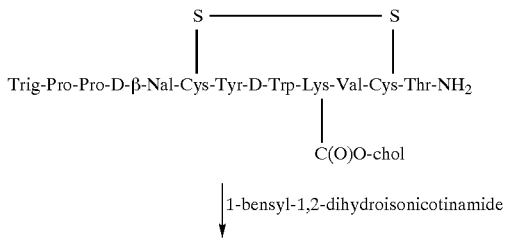
1-bensyl-1,2-dihydroisonicotinamide
[SEQ ID NO.:26]
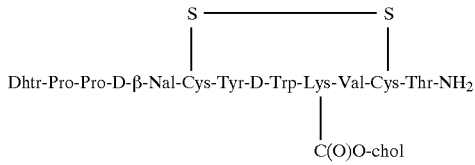

The trigonellinate quaternary salt predecessor of the CDS can also be represented as follows:
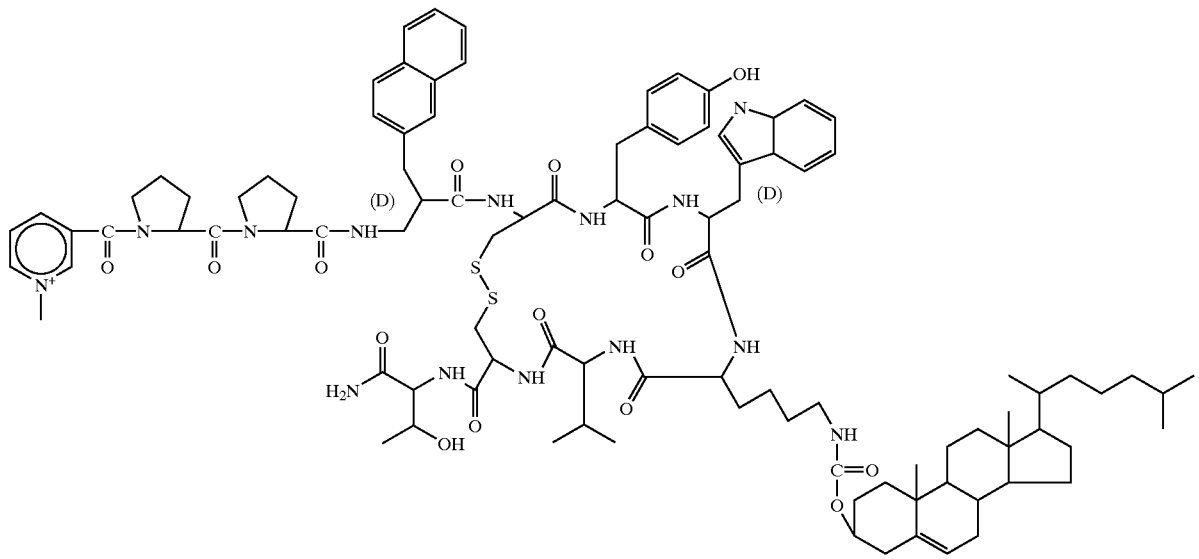
The final product, lanreotide-CDS$_1$, can also be represented as follows:
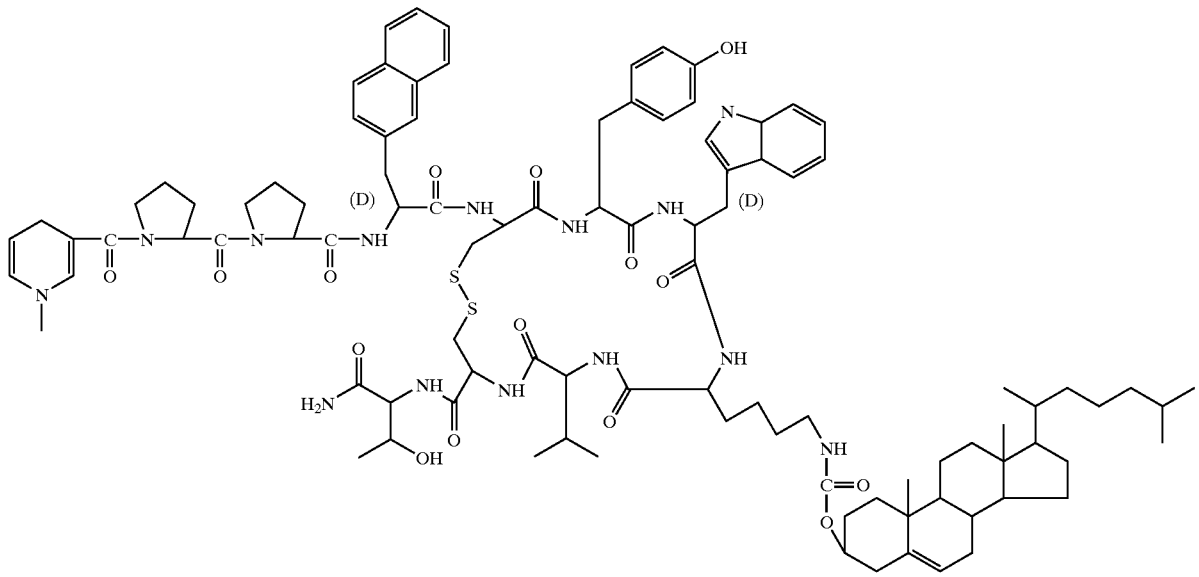

As with SCHEMES I and II, SCHEME III can be modified to introduce other spacers for example -Ala-Ala-, and/or to utilize a different $R_4$ group, for example adamantaneethyl rather than cholesteryl, as described with Scheme I above.

SCHEME IV

Synthesis of octreotide analog #2-$CDS_1$

[SEQ ID NO.: 5]

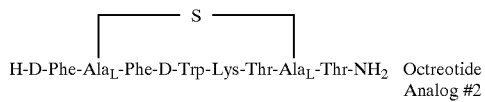

H-D-Phe-$Ala_L$-Phe-D-Trp-Lys-Thr-$Ala_L$-Thr-$NH_2$   Octreotide Analog #2

| Boc—$N_3$

[SEQ ID NO.: 27]

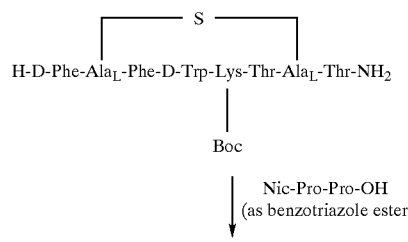

H-D-Phe-$Ala_L$-Phe-D-Trp-Lys-Thr-$Ala_L$-Thr-$NH_2$

|
Boc

| Nic-Pro-Pro-OH (as benzotriazole ester)

[SEQ ID NO.: 28]

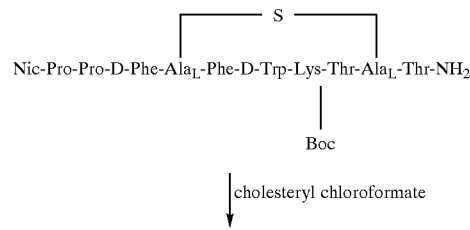

Nic-Pro-Pro-D-Phe-$Ala_L$-Phe-D-Trp-Lys-Thr-$Ala_L$-Thr-$NH_2$

|
Boc

| cholesteryl chloroformate

[SEQ ID NO.:29]

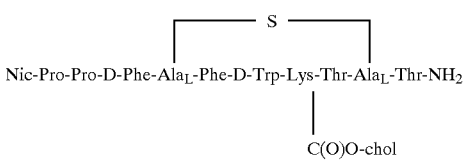

Nic-Pro-Pro-D-Phe-$Ala_L$-Phe-D-Trp-Lys-Thr-$Ala_L$-Thr-$NH_2$

|
C(O)O-chol

| $(CH_3)_2SO_4$

[SEQ ID NO.: 30]

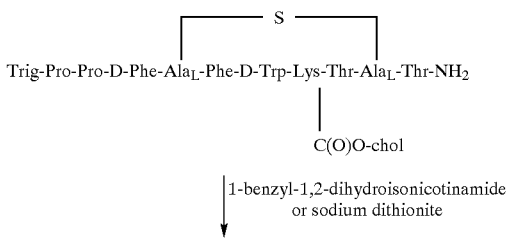

Trig-Pro-Pro-D-Phe-$Ala_L$-Phe-D-Trp-Lys-Thr-$Ala_L$-Thr-$NH_2$

|
C(O)O-chol

| 1-benzyl-1,2-dihydroisonicotinamide or sodium dithionite

[SEQ ID NO.: 31]

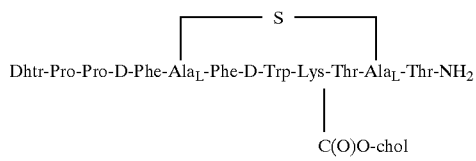

Dhtr-Pro-Pro-D-Phe-$Ala_L$-Phe-D-Trp-Lys-Thr-$Ala_L$-Thr-$NH_2$

|
C(O)O-chol

SCHEME IV can be modified as described with SCHEME I and the other schemes above by use of other spacers, for example -Ala-Ala, or to utilize a different $R_4$ moiety, for example, adamantaneethyl in place of cholesteryl.

SCHEME V

Synthesis of octreotide-$CDS_4$

[SEQ ID NO.: 2]

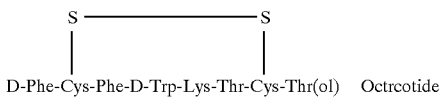

D-Phe-Cys-Phe-D-Trp-Lys-Thr-Cys-Thr(ol)   Octrcotide

 Boc—$N_3$

[SEQ ID NO.: 8]

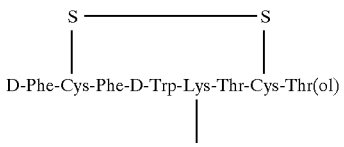

D-Phe-Cys-Phe-D-Trp-Lys-Thr-Cys-Thr(ol)

|
Boc

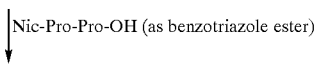 Nic-Pro-Pro-OH (as benzotriazole ester)

-continued

[SEQ ID NO.: 9]

Nic-Pro-Pro-D-Phe-Cys-Phe-D-Trp-Lys-Thr-Cys-Thr(ol)
            |
           Boc (with S—S bridge between the two Cys residues)

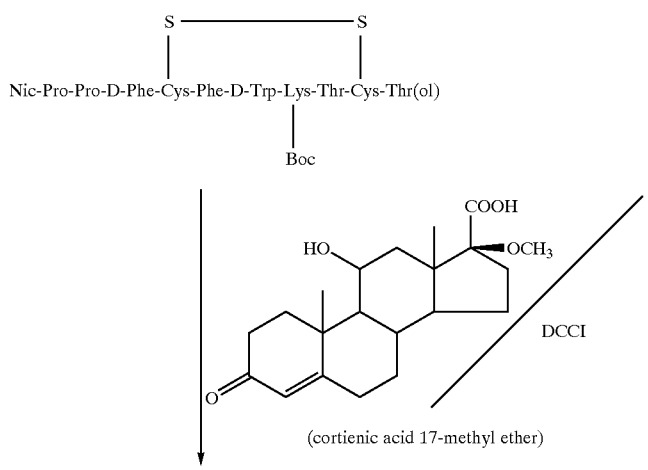

(cortienic acid 17-methyl ether) / DCCI

[SEQ ID NO.: 32]

Nic-Pro-Pro-D-Phe-Cys-Phe-D-Trp-Lys-Thr-Cys-NHCHCH(OH)CH$_3$
            |                                |
           Boc                              CH$_2$ (with S—S bridge between the two Cys residues)

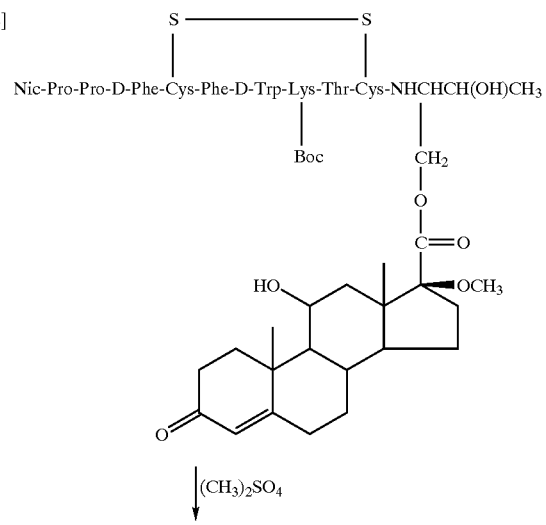

$(CH_3)_2SO_4$

[SEQ ID NO.: 33]

Trig-Pro-Pro-D-Phe-Cys-Phe-D-Trp-Lys-Thr-Cys-NHCHCH(OH)CH$_3$
            |                                 |
           Boc                               CH$_2$ (with S—S bridge between the two Cys residues)

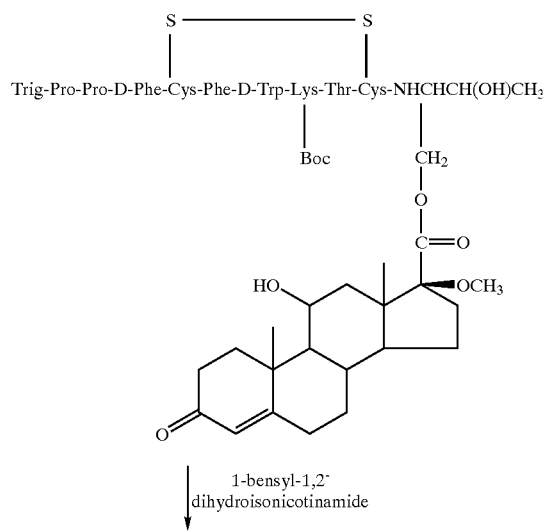

1-bensyl-1,2'-dihydroisonicotinamide

[SEQ ID NO.: 34]
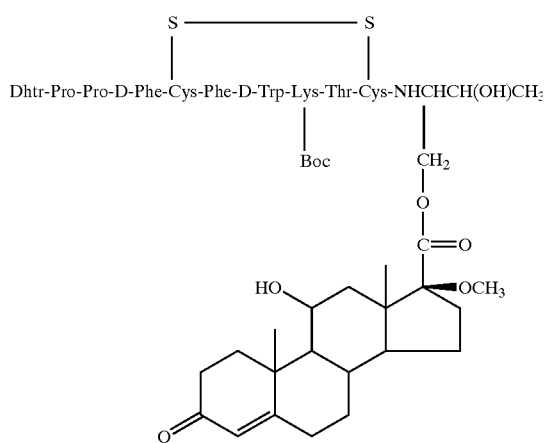
The trigonellinate quaternary salt predecessor of the CDS can also be represented as follows:
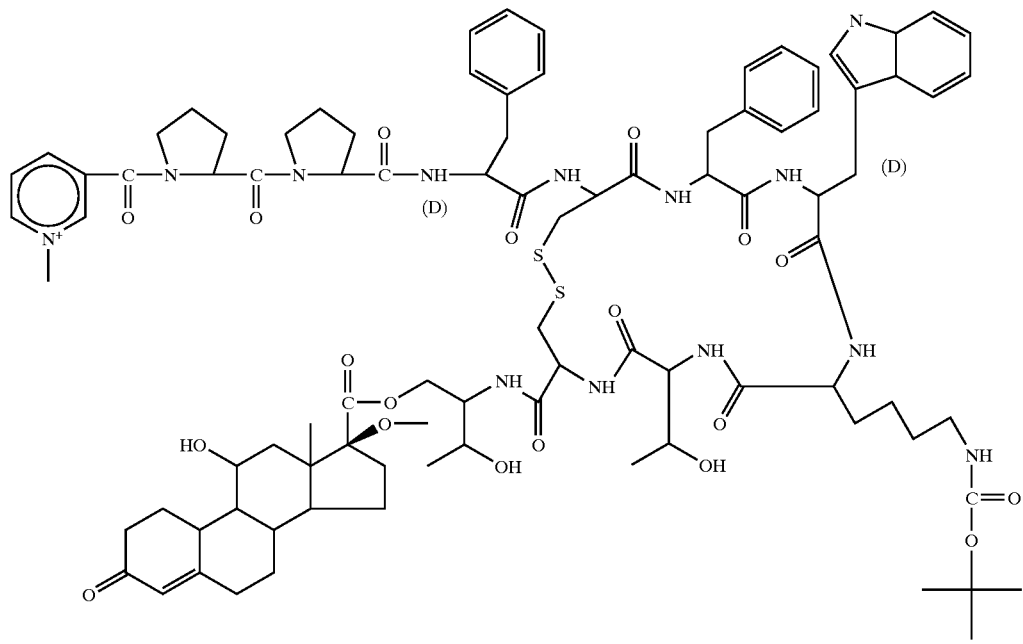

The final product, octreotide-CDS$_4$, can also be represented as follows:
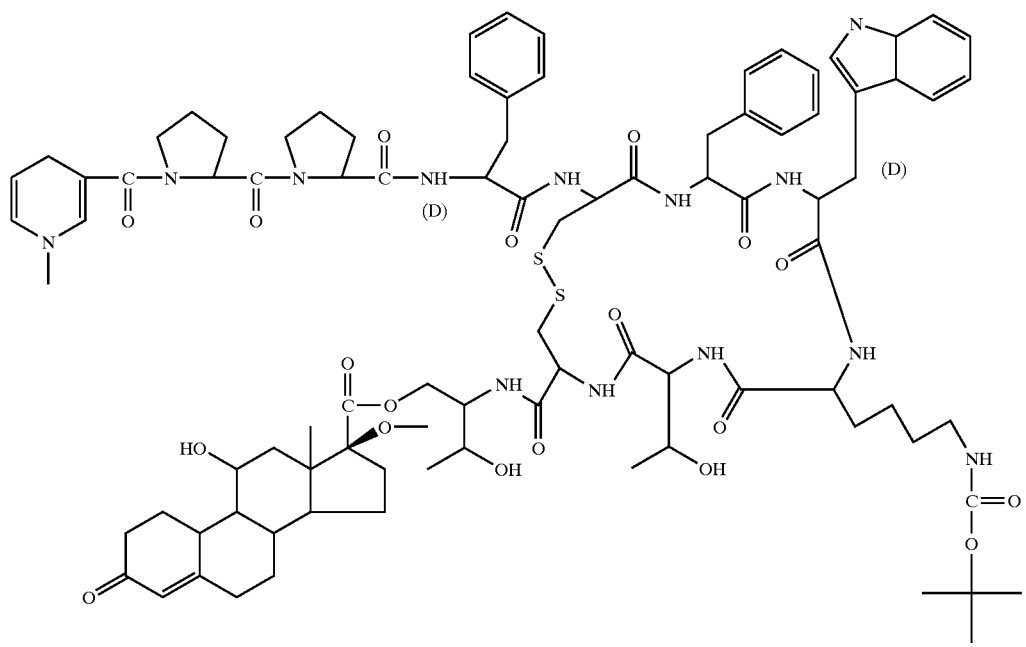
As with SCHEME I and the other schemes, SCHEME V can be modified to introduce other spacers, for example, -Ala-Ala-, and/or a different R$_4$ group can be utilized, for example by using 1-adamantaneacetic acid or Δ$^1$-cortienic acid 17-methyl ether in place of the cortienic acid 17-methyl ether used above.
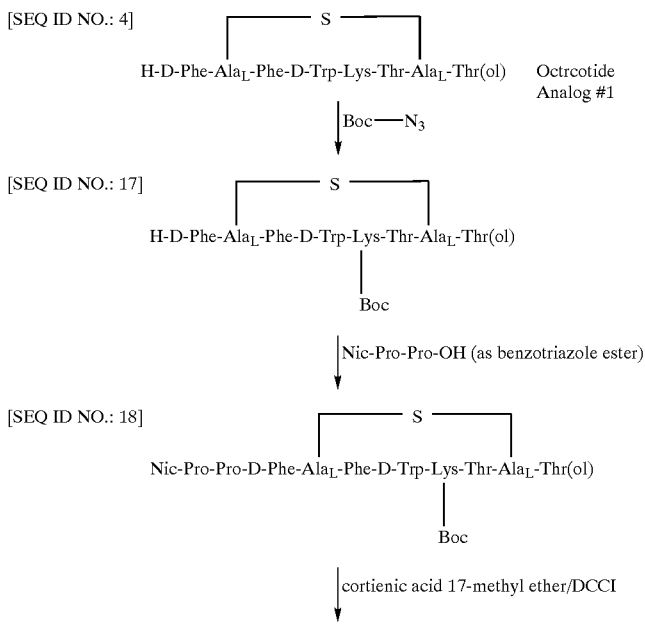

[SEQ ID NO.: 35]
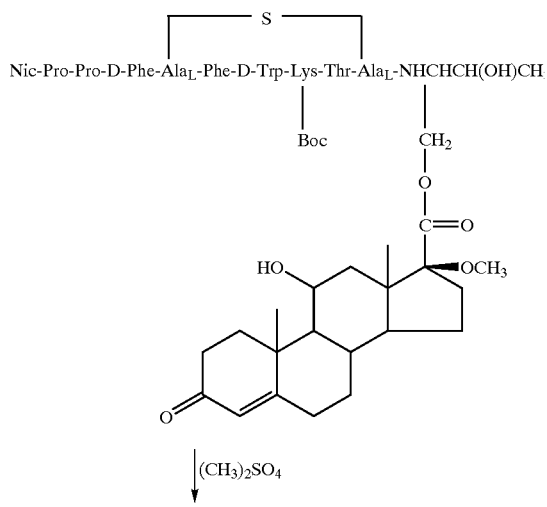
[SEQ ID NO.: 36]
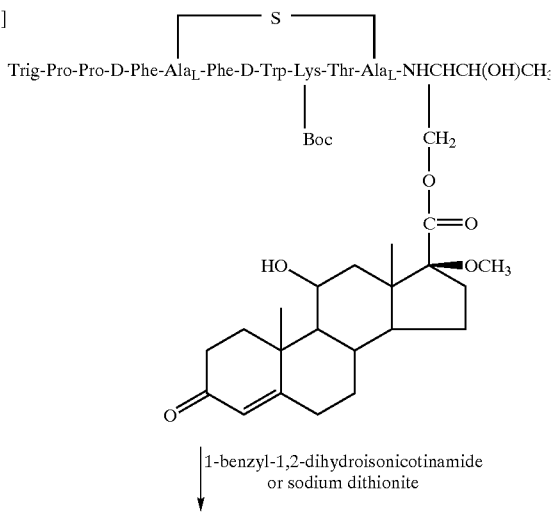
[SEQ ID NO.: 37]
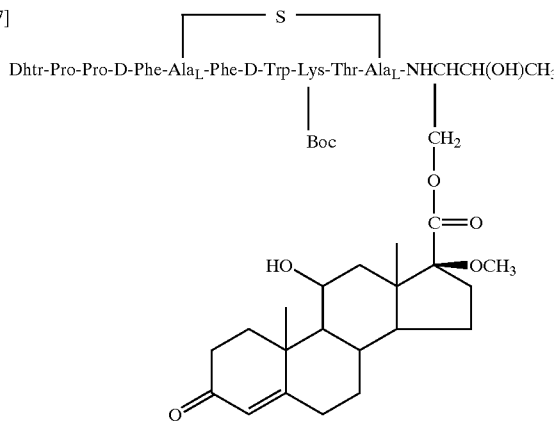
SCHEME VI, like the earlier schemes, can be modified to introduce other spacers, for example, -Ala-Ala-, and/or a different $R_4$ group can be utilized, for example, by using 1-adamantaneacetic acid or $\Delta^1$-cortienic acid 17-methyl ether in place of the cortienic acid 17-methyl ether used above.

SCHEME VII
Synthesis of lanreotide-CDS$_2$
[SEQ ID NO.: 38]
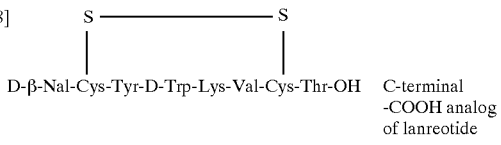   C-terminal
-COOH analog
of lanreotide
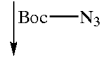 Boc—N$_3$
[SEQ ID NO.: 39]
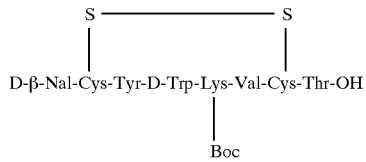
cholesterol + Fmoc-Gly-OH ⟶ Fmoc-Gly-O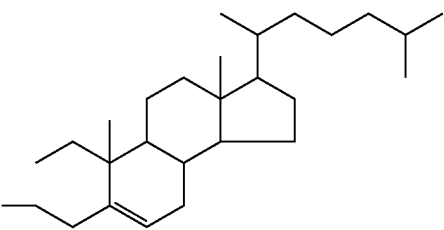
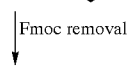 Fmoc removal
Gly-O-chol
[SEQ ID NO.: 40]
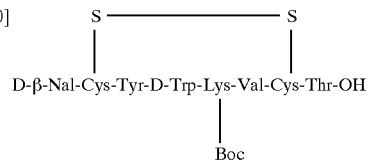
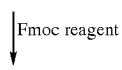 Fmoc reagent
[SEQ ID NO.: 41]
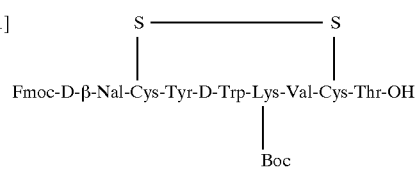
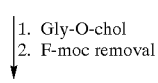 1. Gly-O-chol
2. F-moc removal
[SEQ ID NO.: 42]
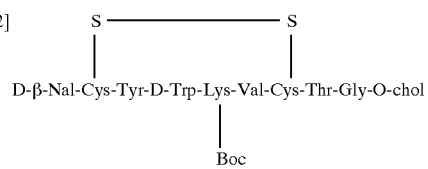
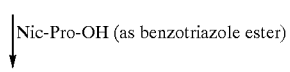 Nic-Pro-OH (as benzotriazole ester)

[SEQ ID NO.: 43]
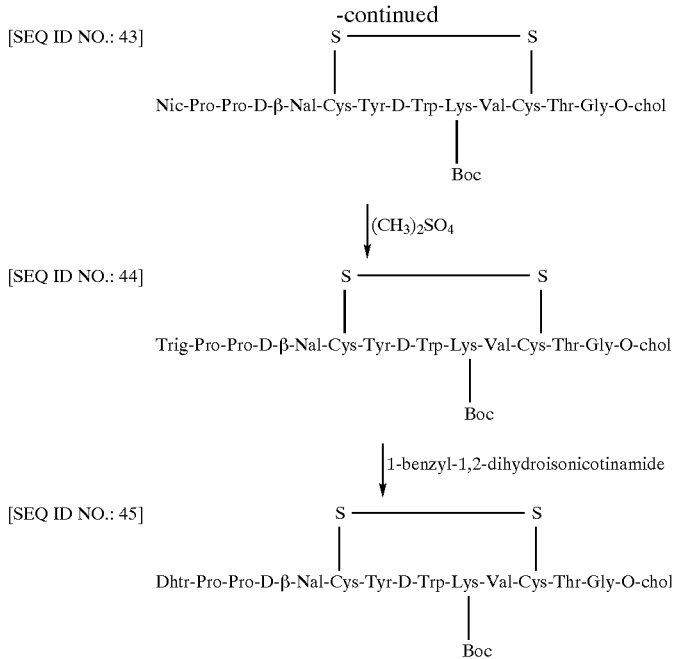
The trigonellinate quaternary salt predecessor of the CDS can also be represented as follows:
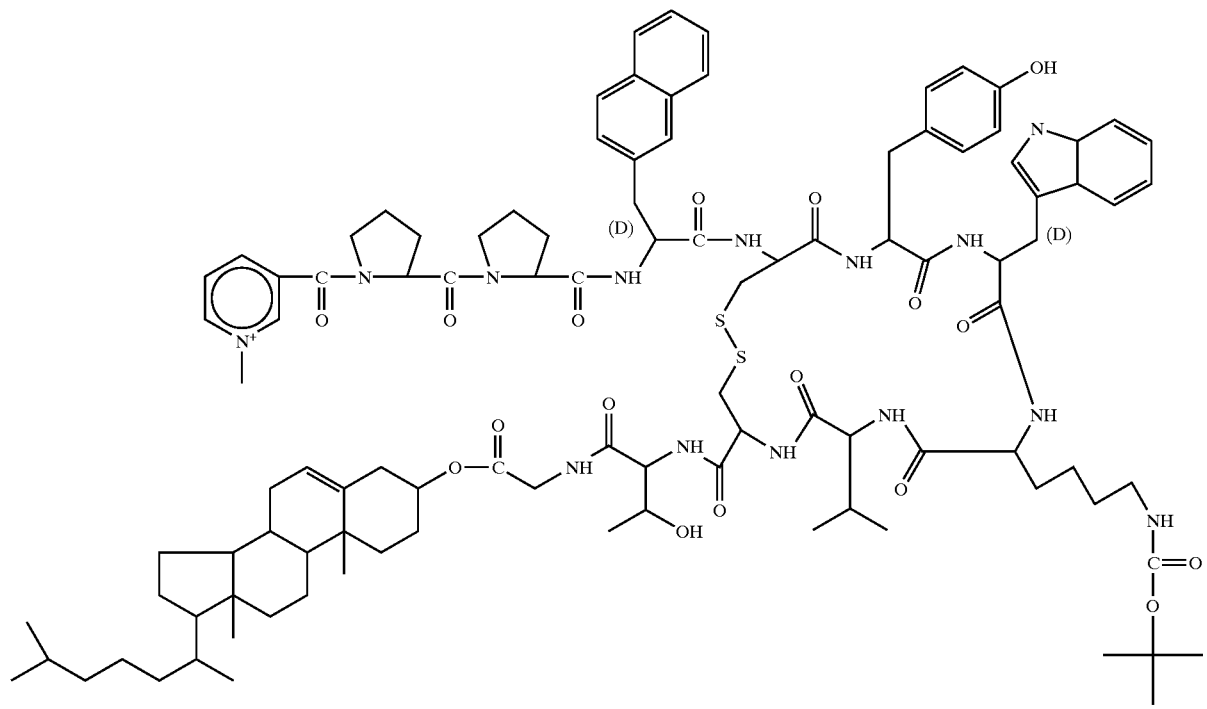

The final product, lanreotide-CDS$_2$, can also be represented as follows:

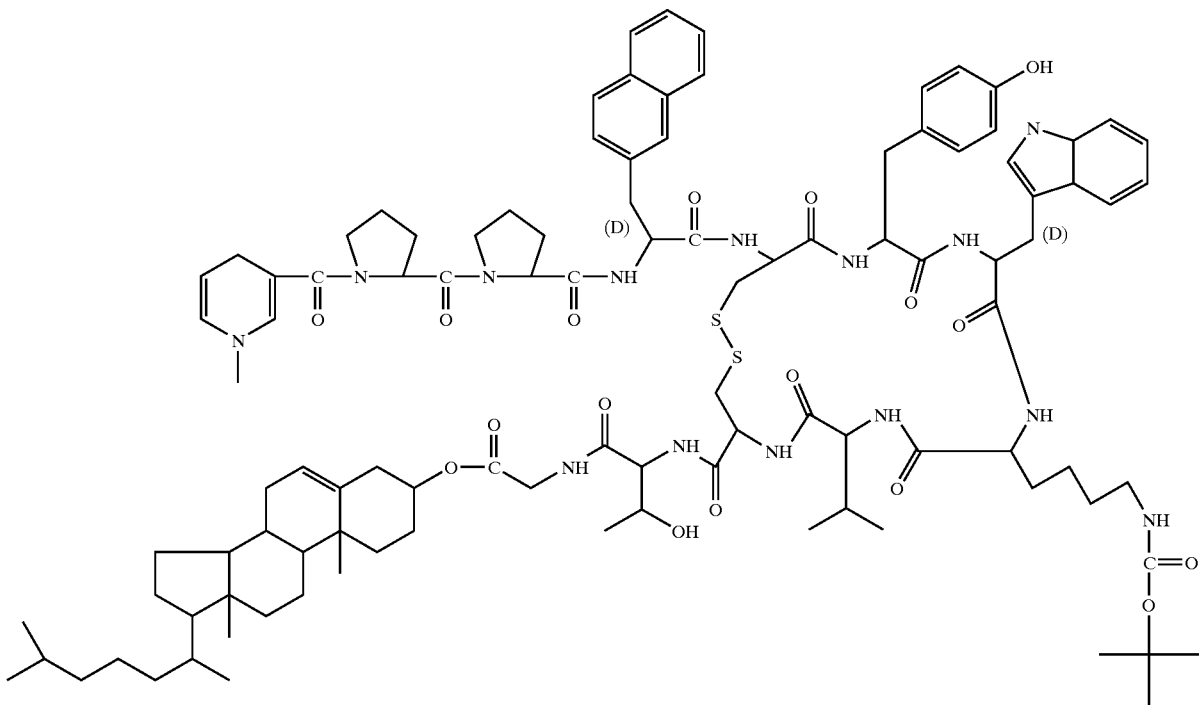

As with SCHEME I and the other schemes above, SCHEME VII can be modified to introduce other spacers, for example, -Ala-Ala-, and/or a different R$_4$ group can be utilized, for example, by using adamantaneethanol in place of cholesterol in the above.

Other general methods for preparing a CDS of lanreotide in which the C-terminal CH$_2$OH is replaced with a CH$_2$OCOR$_4$ group and the free amino group of the lysine residue is protected with a —COOR$_5$ group are described elsewhere in this specification.

SCHEME VIII

Synthesis of octreotide analog #2-CDS$_2$

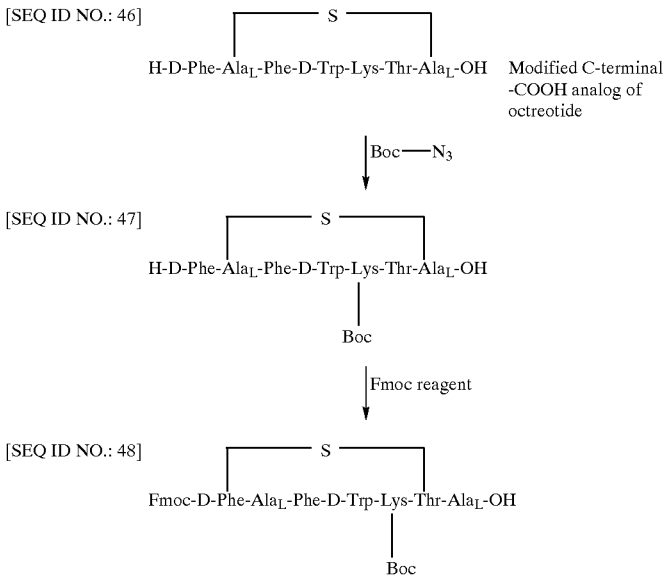

-continued

Gly-O-chol + Fmoc-Thr-OH ⟶ Fmoc-Thr-Gly-O-Chol

↓ Fmoc removal

Thr-Gly-O-chol

[SEQ ID NO.: 49]

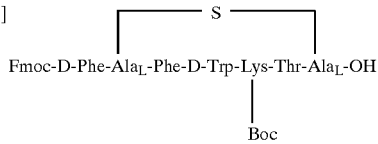
Fmoc-D-Phe-Ala$_L$-Phe-D-Trp-Lys-Thr-Ala$_L$-OH
|
Boc

↓ 1. Gly-O-chol
  2. Fmoc removal

[SEQ ID NO.: 50]

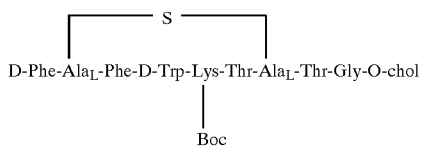
D-Phe-Ala$_L$-Phe-D-Trp-Lys-Thr-Ala$_L$-Thr-Gly-O-chol
|
Boc

↓ Nic-Pro-OH (as benzotriazole ester)

[SEQ ID NO.: 51]

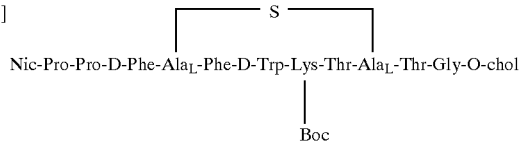
Nic-Pro-Pro-D-Phe-Ala$_L$-Phe-D-Trp-Lys-Thr-Ala$_L$-Thr-Gly-O-chol
|
Boc

↓ $(CH_3)_2SO_4$

[SEQ ID NO.: 52]

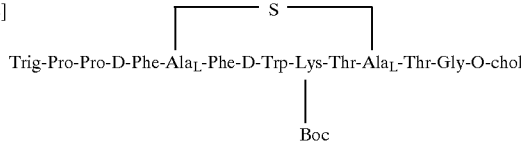
Trig-Pro-Pro-D-Phe-Ala$_L$-Phe-D-Trp-Lys-Thr-Ala$_L$-Thr-Gly-O-chol
|
Boc ↓ sodium dithionite or
1-benzyl-1,2-dihydroisonicotinamide

[SEQ ID NO.: 53]

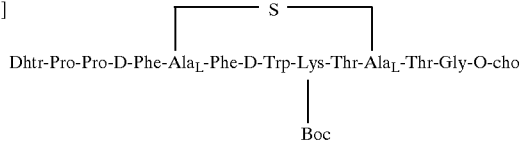
Dhtr-Pro-Pro-D-Phe-Ala$_L$-Phe-D-Trp-Lys-Thr-Ala$_L$-Thr-Gly-O-cho
|
Boc As with SCHEME I and the other schemes above, SCHEME VIII can be modified to introduce other spacers, for example, -Ala-Ala-, and/or a different $R_4$ group can be utilized.

SCHEME IX

Synthesis of octreotide analog #3-CDS

[SEQ ID NO.: 6]

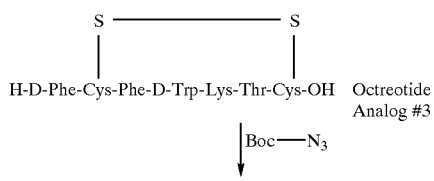
H-D-Phe-Cys-Phe-D-Trp-Lys-Thr-Cys-OH   Octreotide Analog #3
|
Boc—N$_3$
↓

-continued

[SEQ ID NO.: 54]

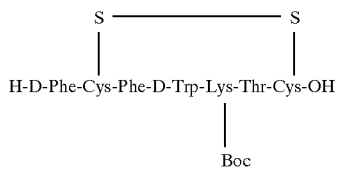
H-D-Phe-Cys-Phe-D-Trp-Lys-Thr-Cys-OH
|
Boc

↓ 1. Fmoc reagent
  2. Cholestrol/DCCI

77

-continued

[SEQ ID NO.: 55]

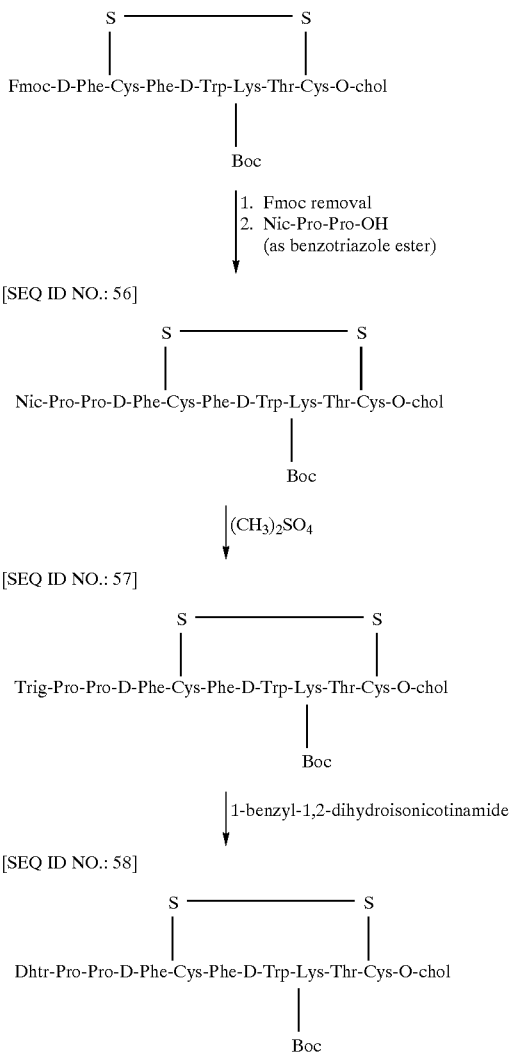

As with SCHEME I and the other schemes above, SCHEME IX can be modified to introduce other spacers, for example -Ala-Ala-, and/or a different R$_4$ group can be utilized, for example, by using adamantaneethanol in place of cholesterol above.

EXAMPLE 1

Synthesis of mono-Boc-sandostatin

Sandostatin (102 mg, 0.10 mmol) was dissolved in 80 ml of water, then mixed with 100 ml of freshly prepared pyridine and 10 ml of TEA. Then 20 ml of cold aqueous solution containing BocN$_3$ (1.50 ml, 10.60 mmol) was added at once and the solution was stirred at room temperature for 2 hours. At the end of this time, NH$_4$OH (3.4 ml, 50 mmol) was added to the solution, which was stirred for an additional 30 minutes. Another 3.4 ml of NH$_4$OH was then added and the solvent was removed on a rotary evaporator. The residue was washed once with 100 ml of ethyl ether and purified on a C-18 column, eluted with 50%–60% acetonitrile, 0.5% HOAc aqueous solution. Fractions containing product were freeze-dried, neutralized, and dried again. 90 mg of pale yellowish solid was obtained in a yield of 80.3%. HPLC showed it was pure and it was confirmed

78 by FAB-MS: [M+H$^+$] at m/z 1119. The product has the structure:

[SEQ ID NO.: 8]

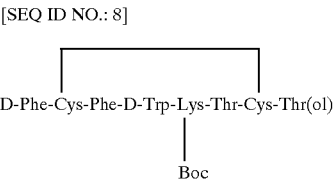

Synthesis of Nic-Pro-Pro-OH

Dried chlorotrityl resin (1.0 g, 1.3 mmol) was mixed with DIEA (81.5 mg, 0.64 mmol), 10 ml of methylene chloride solution containing Fmoc-Pro-OH (263 mg, 0.78 mmol) was added and the mixture was stirred at room temperature for 5 minutes. Then DIEA (170 μl, 1.34 mmol) was added and the mixture was stirred rapidly for a further 60 minutes. At the end of this time, 1 ml of HPLC pure methanol was added and the mixture was stirred for 10 minutes to end-cap the remaining trityl groups on the resin. The resin was washed successively with 3×20 ml methylene chloride, 2×20 ml isopropanol, 2×20 ml DMF, 2×20 ml isopropanol, 2×20 ml methanol and 2×20 ml ethyl ether. It was then dried over solid KOH. This Fmoc-Pro-resin was used for the synthesis of Nic-Pro-Pro-OH, according to the standard protocol of solid-phase peptide synthesis by using PyBOP as coupling agent. The preparation of active ester is described below.

Fmoc-Pro-OH (1.01 g, 3 mmol) was dissolved in 10 ml of DMA, PyBOP (1.56 g, 3 mmol), DIEA (1.04 ml, 6 mmol) were added, and the resultant mixture was added at once into the deprotected resin for the coupling reaction. The solution was bubbled gently for 30–60 minutes until the ninhydrin test (Kaiser test) was negative.

After completion of synthesis, the resin was dried and deprotected by treating with a mixture (2 ml HOAC, 2 ml TFE and 16 ml CH$_2$Cl$_2$) at room temperature for 30 minutes. The product was filtered and the solvent was removed on a rotary evaporator to afford 220 mg of white solid in a total yield of 74.8%. HPLC showed the product was pure (solvent: 20% acetonitrile, 0.1% TFA aqueous solution) and this was confirmed by FAB-MS [M+H$^+$] at m/z 318.

EXAMPLE 3

Synthesis of Nic-Pro-Pro-(mono-Boc-sandostatin)

TFA-Nic-Pro-Pro-OH (155.0 mg, 0.36 mmol) and HOBt (48.6 mg, 0.36 mmol) were dissolved in 5 ml of DMA, the solution was cooled to 0° C. and DIC (45.4 mg, 0.36 mmol) was added. The resultant solution was stirred at 0° C. for 10 minutes and then at room temperature for 20 minutes. Then, mono-Boc-sandostatin (214 mg, 0.18 mmol) was added and the pH was adjusted by 8–8.5 by adding DIEA. The reaction mixture was stirred at room temperature for 120 minutes. HPLC showed the reaction was complete within 1 hour. The mixture was diluted with 8 ml of 35% acetonitrile, 0.5% HOAc aqueous solution, applied to a C-18 column and eluted with 35–50% acetonitrile, 0.5% HOAc aqueous solution; fractions containing the product were combined and freeze dried twice. 165.0 mg of white solid (7.0 mg) was obtained in a yield of 64.7%. HPLC gave only one peak and the product was confirmed by the Electrospray ionization (ESI) mass: [M+H$^+$] at m/z 1419. The product has the structure:

[SEQ ID NO.: 9]

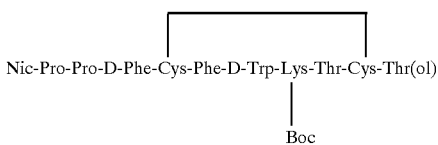

EXAMPLE 4

Synthesis of [SEQ ID NO.: 11]

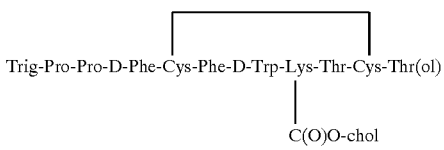

To a flask containing the product of EXAMPLE 3 (80.0 mg, 56 μmol), there was added a mixture of TFA (1.9 ml), H₂O (0.10 ml) and indole (19.5 mg, 167 μmol) under argon. The reaction mixture was stirred at room temperature for 20 minutes. The solvent was then removed with a stream of argon, EtOEt (30 ml) was then added, the mixture was stirred for another two minutes at room temperature and then was stored at −15° C. for 20 minutes. The white precipitate which formed was collected by centrifuging the cooled solution, and was then dried under vacuum over NaOH for 1 hour.

The residue was dissolved in DMA (1.4 ml), DIEA was then added until the pH was 8.5, and DMA solutions of cholesteryl chloroformate (28.3 mg, 63 μmol) and DIEA were added alternately (to maintain the pH at 8–9) over a period of 15 minutes. The mixture was then stirred at room temperature for 40 minutes. Ninhydrin test showed no free amino group was remaining.

This mixture was diluted with 7 ml of methylene chloride, then was applied directly onto a neutral alumina column (1.2×10 cm), and eluted successively with methylene chloride (15 ml), chloroform (20 ml), 60 ml 1% methanol/chloroform and 100 ml of 2% methanol/chloroform. Fractions containing TLC pure product were combined and evaporated on a rotary evaporator. 75 mg of yellowish solid was obtained; yield: 77.4%; TLC: CHCl₃/MeOH(10:1), Rf=0.70; ESI-MS, [M+H⁺] at m/z 1731.

EXAMPLE 5

Synthesis of [SEQ ID NO.: 11]

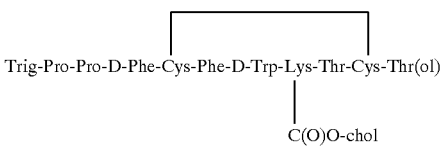

The product of EXAMPLE 4 (60.0 mg, 34.7 μmol) was dissolved in chloroform (5 ml) and a solution of dimethyl sulfate (310 mg, 2.46 mmol) in chloroform (3.8 ml) was added while stirring under argon. The mixture was stirred at room temperature for 14 hours. TLC showed that the starting material had disappeared. After removing most of the solvent on a rotary evaporator, EtOEt (8 ml) was added, the mixture was stirred for another 10 minutes and then was cooled to −15° C. for 10 minutes. Centrifugation gave 50 mg of pale yellowish solid; yield, 77.6%, ESI-MS, [M⁺] 1746. The product can also be represented as follows:

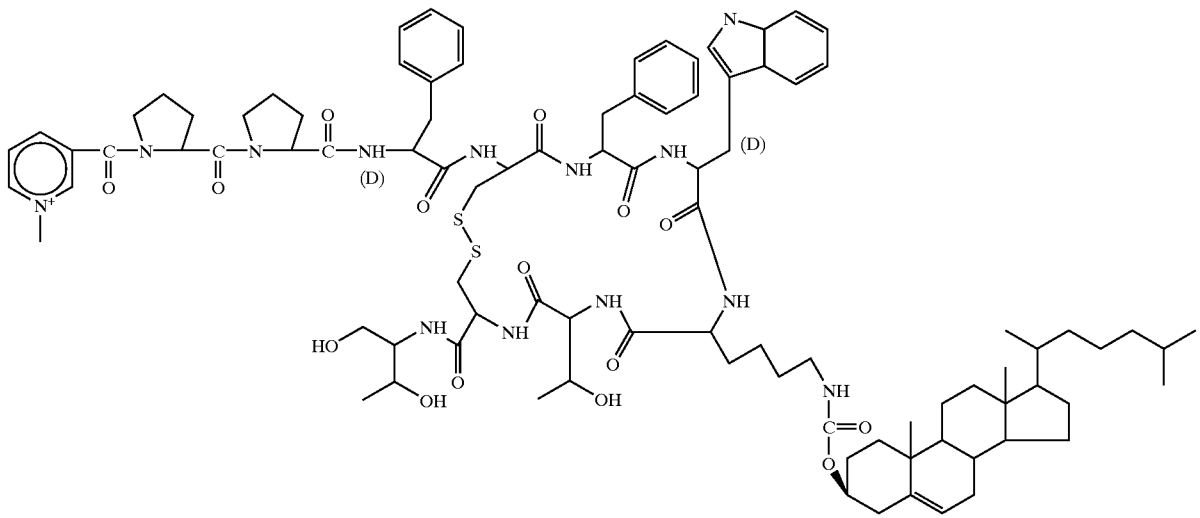

EXAMPLE 6

Synthesis of [SEQ ID NO.: 12]

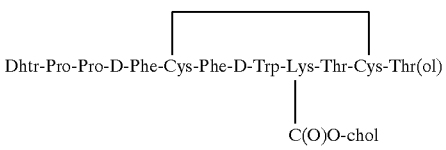

The product of EXAMPLE 5 (5.6 mg, 3 μmol) was dissolved in DMA (10 μl) and MeCN (10 μl), and a solution of DIEA (0.39 mg, 3 μmol) in MeCN (10 μl) was added while stirring under argon, followed by addition of a solution of 1-Bz-1,2-dihydroisonicotinamide (0.64 mg, 3 μmol)

in DMA (5 μl) and MeCN (5 μl). The mixture was stirred at room temperature for 2 hours. The MeCN was then removed by introducing a stream of argon and 400 μl of EtOAc was added. The precipitate which formed was removed by centrifugation and the clear solution was washed once with 200 μl of deaerated water, the EtOAc phase was dried over Na₂SO₄ and was dried under high vacuum. 2.0 mg of yellowish solid was obtained; yield, 38%. This residue reduces an alcoholic solution of silver nitrate slowly at room temperature, UV max=360 run, ESI-MS, [M⁺] 1746. The product can also be represented as follows:

yellowish solid was obtained in a yield of 58%. Compared with the NMR spectrum of pure 1,4-dihydrotrigonellinamide (which was prepared by the Na₂S₂O₄ reducing reaction), this product contained 70% 1,4-dihydrotrigonellinamide isomer.

EXAMPLE 8
Reducing Reaction of (Nic-Cys-OEt)₂

(Nic-Cys-OEt)₂ (8.1 mg, 0.016 mmol) was dissolved in 1 ml of DMA under argon and 1-benzyl-1,2-dihydroisonicotinamide (20.5 mg, 0.096 mmol) was added while stirring. 10 μl solution samples were taken at appro-

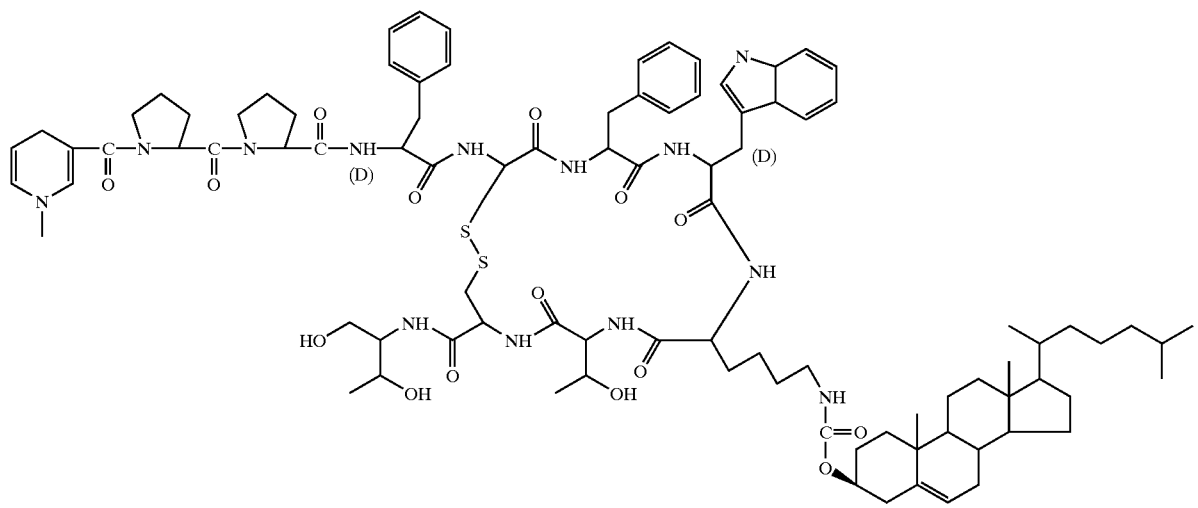

The following experiments were conducted to demonstrate that 1-benzyl-1,2-dihydroisonicotinamide can reduce the trigonelloyl group, without breaking the S—S bond during a two hour reaction in DMA or CH₃CN, while the concentration is 0.1 M.

In these experiments, trigonellinamide, (Trig-Cys-OEt)₂, (Nic-Cys-OEt)₂,

[SEQ ID NO.: 59]  Trig-Gly-Gly-Cys-Gly-Gly-Cys-Gly-OH,

[SEQ ID NO.: 60]  Nic-Gly-Gly-Cys-Gly-Gly-Cys-Gly-OH,  and

[SEQ ID NO.: 61]  Nic-Pro-Pro-D-Phe-Cys-Phe-D-Trp-Lys-Thr-Cys-Thr(ol
                                                              |
                                                             Boc were used as model molecules.

EXAMPLE 7
Reducing Reaction of Trigonellinamide

Trigonellinamide (372 mg, 1.5 mmol) was suspended in 15 ml of CH₃CN under argon, 1-benzyl-1,2-dihydroisonicotinamide (321 mg, 1.5 mmol) was added while stirring, and the reaction was monitored by UV. The $\lambda_{max}$ shifted from 371 nm to 361 nm during a period of 120 minutes (the $\lambda_{max}$ of 1-benzyl-1,2-dihydroisonicotinamide is 371 nm). After removing the solvent, the residue was flash chromatographed on a short column of neutral alumina, eluted with CH₃Cl and CH₃Cl/MeOH (10/1). Fractions containing the product were combined, after removing the solvent, the residue was extracted with EtOAc and dried over Na₂SO₄. The solvent was evaporated and 120 mg of priate time points, diluted with 2 ml of eluting solution (60% acetonitrile, 0.1% TFA aqueous solution) and analyzed by HPLC. No detectable decrease in the corresponding peak height was found during a period of 5 hours.

EXAMPLE 9
Reducing Reaction of (Trig-Cys-OEt)₂

(Trig-Cys-OEt)₂ (18.2 mg, 0.024 mmol) was dissolved in 0.5 ml of DMA under argon and 1-benzyl-1,2-dihydroisonicotinamide (10.3 mg, 0.048 mmol) was added while stirring. The reaction was monitored by UV. The $\lambda_{max}$ shifted from 370 nm to 359 run during a period of 120 minutes (the $\lambda_{max}$ of 1-benzyl-1,2-dihydroisonicotinamide is 370 nm).

EXAMPLE 10
Reducing Reaction of
[SEQ ID NO.: 60]

Nic- Gly-Gly-Cys-Gly-Gly-Cys-Gly-OH (7.3 mg, 0.01 mmol) was dissolved in 2 ml of DMA under argon and NaHCO₃ (2.0 mg, 0.024 mmol) was added, followed by the addition of 1-benzyl-1,2-dihydroisonicotinamide (42 mg, 0.20 mmol) while stirring. Solution samples (10 μl each) were taken at appropriate time points, diluted with 100 μl of eluting solution (20% acetonitrile, 0.1% TFA aqueous solution) and analyzed by HPLC. No detectable decrease in the corresponding peak height was found over a period of 5 hours.

EXAMPLE 11

Reducing Reaction of
[SEQ ID NO.: 59]

Trig- Gly-Gly-Cys-Gly-Gly-Cys-Gly-OH:
[SEQ ID NO.: 59]

Trig- Gly-Gly-Cys-Gly-Gly-Cys-Gly-OH (18.45 mg, 0.025 mmol) was dissolved in 1.0 ml of DMA under argon. DIEA was added to adjust the pH to 6.5, 1-benzyl-1,2-dihydroisonicotinamide (5.35 mg, 0.025 mmol) in 0.20 ml of DMA was added while stirring, and samples were taken at appropriate time points for UV analysis. The $\lambda_{max}$ shifted from 367 nm to 357 nm over a period of 10 hours.

EXAMPLE 12

Reducing Reaction of
[SEQ ID NO.: 61]

Nic-Pro-Pro-D-Phe-Cys-Phe-D-Trp-Lys-Cys-Thr(ol) inDMA
|
Boc
[SEQ ID NO.: 61]

Nic-Pro-Pro-D-Phe-Cys-Pre-D-Trp-Lys-Cys-Thr(ol)
|
Boc (5.7 mg, 4 µmol) was dissolved in 200 µl of DMA under argon and DIEA (0.5 mg, 4 µmol) was added, followed by the addition of 1-benzyl-1,2-dihydroisonicotinamide (8.5 mg, 40 µmol) in 200 µl of DMA with stirring. Solution samples (10 µl each) were taken at appropriate time points, diluted with 90 µl of eluting solution (60% acetonitrile, 0.1% TFA aqueous solution) and analyzed by HPLC. No detectable decrease in the corresponding peak height was found over a period of 5 hours. After purification by HPLC, the corresponding peak was collected and dried under high vacuum with argon protection. The MS spectrum showed that the S—S bond had not been broken.

EXAMPLE 13

Reducing Reaction of
[SEQ ID NO.: 61]

Nic-Pro-Pro-D-Phe-Cys-Pre-D-Trp-Lys-Cys-Thr(ol) in CH₃CN
|
Boc
[SEQ ID NO.: 61]

Nic-Pro-Pro-D-Phe-Cys-Pre-D-Trp-Lys-Cys-Thr(ol)
|
Boc (5.7 mg, 4 µmol) was dissolved in 20 µl of DMA and 200 µl of CH₃CN under argon. DIEA (0.5 mg, 4 µmol) was added, followed by 1-benzyl-1,2-dihydroisonicotinamide (8.5 mg, 40 µmol) in 200 µl of CH₃CN, with stirring. Solution samples (10 µl each) were taken at appropriate time points, diluted with 90 µl of eluting solution (60% acetonitrile, 0.1% TFA aqueous solution) and analyzed by HPLC. No detectable decrease in the corresponding peak height was found during a period of 4 hours. After purification by HPLC, the corresponding peak was collected and dried under high vacuum with argon protection. The MS spectrum showed that the S—S bond had not been broken.

While the invention has been described in terms of various preferred embodiments, the person skilled in the art will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. A compound of the formula

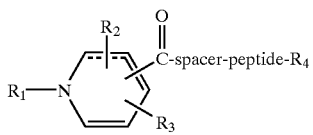

(I)

or a non-toxic pharmaceutically acceptable salt thereof, wherein:

$R_1$ is $C_1$–$C_7$ alkyl, $C_1$–$C_7$ haloalkyl or $C_7$–$C_{12}$ aralkyl;

$R_2$ and $R_3$, which are the same or different, are each selected from the group consisting of hydrogen, halo, cyano, $C_1$–$C_7$ alkyl, $C_1$–$C_7$ alkoxy, $C_2$–$C_8$ alkoxycarbonyl, $C_2$–$C_8$ alkanoyloxy, $C_1$–$C_7$ haloalkyl, $C_1$–$C_7$ alkylthio, $C_1$–$C_7$ alkylsulfinyl, $C_1$–$C_7$ alkylsulfonyl, —CH=NOR''' wherein R''' is hydrogen or $C_1$–$C_7$ alkyl, and —CONR'R'' wherein R' and R'', which are the same or different, are each hydrogen or $C_1$–$C_7$ alkyl;

or one of $R_2$ and $R_3$ together with the adjacent ring carbon atom forms a phenyl ring fused to the six-membered heterocyclic ring, which phenyl ring is unsubstituted or is substituted with one or two substituents, which are the same or different, selected from the group consisting of hydroxy, protected hydroxy, halo, cyano, $C_1$–$C_7$ alkyl, $C_1$–$C_7$ alkoxy, $C_2$–$C_8$ alkoxycarbonyl, $C_2$–$C_8$ alkanoyloxy, $C_1$–$C_7$ haloalkyl, $C_1$–$C_7$ alkylthio, $C_1$–$C_7$ alkylsulfinyl, $C_1$–$C_7$ alkylsulfonyl, —CH=NOR''' wherein R''' is hydrogen or $C_1$–$C_7$ alkyl, and —CONR'R'' wherein R' and R'', which are the same or different, are each hydrogen or $C_1$–$C_7$ alkyl;

the dotted lines represent a double bond in one of the two indicated positions, the depicted ring system being a 1,4- or 1,6-dihydropyridine, a 1,4- or 1,2-dihydroquinoline, or a 1,2-dihydroisoquinoline;

"spacer" is an L-amino acid unit or a di- or tripeptide consisting of 2 or 3 L-amino acid units, the N-terminal amino acid of said spacer being bonded to the depicted carbonyl carbon via an amide bond;

and "peptide" is a peptide having 2 to 20 amino acid units having growth factor inhibitory activity which is octreotide or lanreotide, wherein the N-terminal phenylalanine or napthylalanine of said peptide is bonded to the C-terminal amino acid of said spacer via a peptide bond, and wherein the C-terminal threonine of said peptide:

(a) has a C-terminal carboxyl group —COOH which has been replaced with a —COOR$_4$ group wherein R$_4$ is $C_6$–$C_{30}$ polycycloalkyl-$C_pH_{2p}$— wherein p is 0, 1, 2, or 3, or $C_6$–$C_{30}$ polycycloalkenyl-$C_pH_{2p}$— wherein p is defined as above;

(b) has a C-terminal —CH$_2$OH group which has been replaced with a —CH$_2$OCOR$_4$ group wherein R$_4$ is defined as above;

(c) has a C-terminal —CONH$_2$ group which has been replaced with a —CO-Gly-OR$_4$ group wherein R$_4$ is defined as above, said —CO-Gly-OR$_4$ group regenerating the C-terminal —CONH$_2$ group in vivo;

(d) has a C-terminal —CONH$_2$ group; or (e) has a C-terminal —CH$_2$OH group;

with the provisos that:

(1) when the C-terminal amino acid is as defined in (a), (b) or (c) above, the side chain —NH$_2$ group of lysine of the peptide is replaced with a —NHCOOR$_5$ group wherein R$_5$ is C$_1$–C$_7$ alkyl or benzyl; and (2) when the C-terminal amino acid is as defined in (d) or (e) above, then the side chain —NH$_2$ group of lysine of the peptide is replaced with a —NHCOOR$_4$ group wherein R$_4$ is defined as above.

2. A compound according to claim 1, wherein R$_1$ is methyl.

3. A compound according to claim 1, wherein the depicted ring system is a 1,4-dihydropyridine or 1,6-dihydropyridine.

4. A compound according to claim 1, wherein

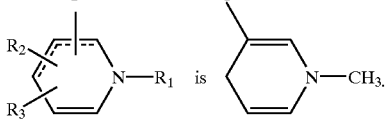

5. A compound according to claim 1, wherein "spacer" is an L-amino acid selected from the group consisting of alanine, proline, glycine and phenylalanine, or a dipeptide consisting of L-amino acid units selected from said group.

6. A compound according to claim 1, wherein the peptide is octreotide.

7. A compound according to claim 1, wherein R$_4$ is —C$_p$H$_{2p}$-steryl wherein p is 0.

8. A compound according to claim 7, wherein R$_4$ is a radical of the formula

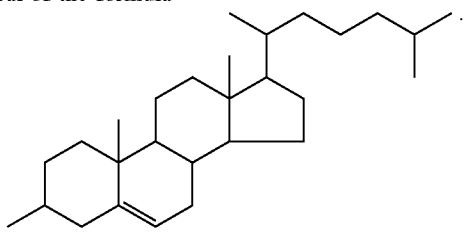

9. A compound of the formula

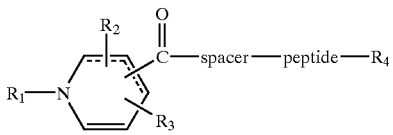

(I)

or a non-toxic pharmaceutically acceptable salt thereof, wherein:

R$_1$ is C$_1$–C$_7$ alkyl, C$_1$–C$_7$ haloalkyl or C$_7$–C$_{12}$ aralkyl;

R$_2$ and R$_3$, which are the same or different, are each selected from the group consisting of hydrogen, halo, cyano, C$_1$–C$_7$ alkyl, C$_1$–C$_7$ alkoxy, C$_2$–C$_8$ alkoxycarbonyl, C$_2$–C$_8$ alkanoyloxy, C$_1$–C$_7$ haloalkyl, C$_1$–C$_7$ alkylthio, C$_1$–C$_7$ alkylsulfinyl, C$_1$–C$_7$ alkylsulfonyl, —CH=NOR''' wherein R''' is hydrogen or C$_1$–C$_7$ alkyl, and —CONR'R'' wherein R' and R'', which are the same or different, are each hydrogen or C$_1$–C$_7$ alkyl;

or one of R$_2$ and R$_3$ together with the adjacent ring carbon atom forms a phenyl ring fused to the six-membered heterocyclic ring, which phenyl ring is unsubstiuted or is substituted with one or two substituents, which are the same or different, selected from the group consisting of hydroxy, protected hydroxy, halo, cyano, C$_1$–C$_7$ alkyl, C$_1$–C$_7$ alkoxy, C$_2$–C$_8$ alkoxycarbonyl, C$_2$–C$_8$ alkanoyloxy, C$_1$–C$_7$ haloalkyl, C$_1$–C$_7$ alkylthio, C$_1$–C$_7$ alkylsulfinyl, C$_1$–C$_7$ alkylsulfonyl, —CH=NOR''' wherein R''' is hydrogen or C$_1$–C$_7$ alkyl, and —CONR'R'' wherein R' and R'', which are the same or different, are each hydrogen or C$_1$–C$_7$ alkyl;

the dotted lines represent a double bond in one of the two indicated positions, the depicted ring system being a 1,4- or 1,6-dihydropyridine, a 1,4- or 1,2-dihydroquinoline, or a 1,2dihydroisoquinoline;

"spacer" is an L-amino acid selected from the group consisting of alanine and proline, or a dipeptide consisting of L-amino acid units selected from said group, the N-terminal amino acid of said spacer being bonded to the depicted carbonyl carbon via an amide bond;

and "peptide" is a peptide having 2 to 20 amino acid units having growth factor inhibitory activity which is octreotide or lanreotide, wherein the N-terminal phenylalanine or napthylalanine of said peptide is bonded to the C-terminal amino acid of said spacer via a peptide bond, and wherein the C-terminal threonine of said peptide:

(a) has a C-terminal carboxyl group —COOH which has been replaced with a —COOR$_4$ group wherein R$_4$ is C$_6$–C$_{30}$ polycycloalkyl-C$_p$H$_{2p}$— wherein p is 0, 1, 2 or 3, or C$_6$–C$_{30}$ polycycloalkenyl-C$_p$H$_{2p}$— wherein p is defined as above, (b) has a C-terminal —CH$_2$OH group which has been replaced with a —CH$_2$OCOR$_4$ group wherein R$_4$ is defined as above;

(c) has a C-terminal —CONH$_2$ group which has been replaced with a —CO-Gly-OR$_4$ group wherein R$_4$ is defined as above, said —CO-Gly-OR$_4$ group regenerating the C-terminal —CONH$_2$ group in vivo;

(d) has a C-terminal —CONH$_2$ group; or (e) has a C-terminal —CH$_2$OH group;

with the provisos that:

(1) when the C-terminal amino acid is as defined in (a), (b) or (c) above, the side chain —NH$_2$ group of lysine of the peptide is replaced with a —NHCOOR$_5$ group wherein R$_5$ is C$_1$–C$_7$ alkyl or benzyl; and (2) when the C-terminal amino acid is as defined in (d) or (e) above, then the side chain —NH$_2$ group of the peptide is replaced with a —NHCOOR$_4$ group wherein R$_4$ is defined as above.

10. A compound according to claim 9, wherein R$_1$ is methyl.

11. A compound according to claim 9, wherein the depicted ring system is a 1,4-dihydropyridine or 1,6-dihydropyridine.

12. A compound according to claim 9, wherein

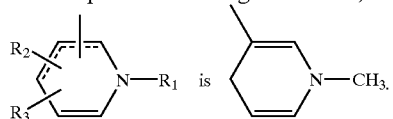

13. A compound according to claim 9, wherein the peptide is octreotide.

14. A compound according to claim 9, wherein R$_4$ is —C$_p$H$_{2p}$-steryl wherein p is 0.

15. A compound according to claim 14, wherein R$_4$ is a radical of the formula

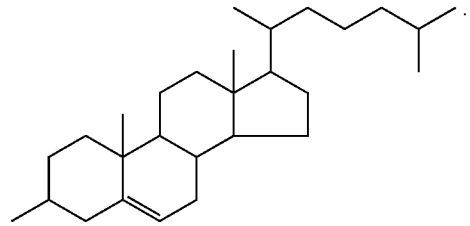

16. A compound according to claim 13, wherein R$_4$ is —C$_p$H$_{2p}$-steryl or —C$_p$H$_{2p}$-adamantyl.

17. A compound according to claim 13, wherein R$_4$ is —C$_p$H$_{2p}$-steryl or —C$_p$H$_{2p}$-adamantyl.

18. The compound according to claim 9, having the formula

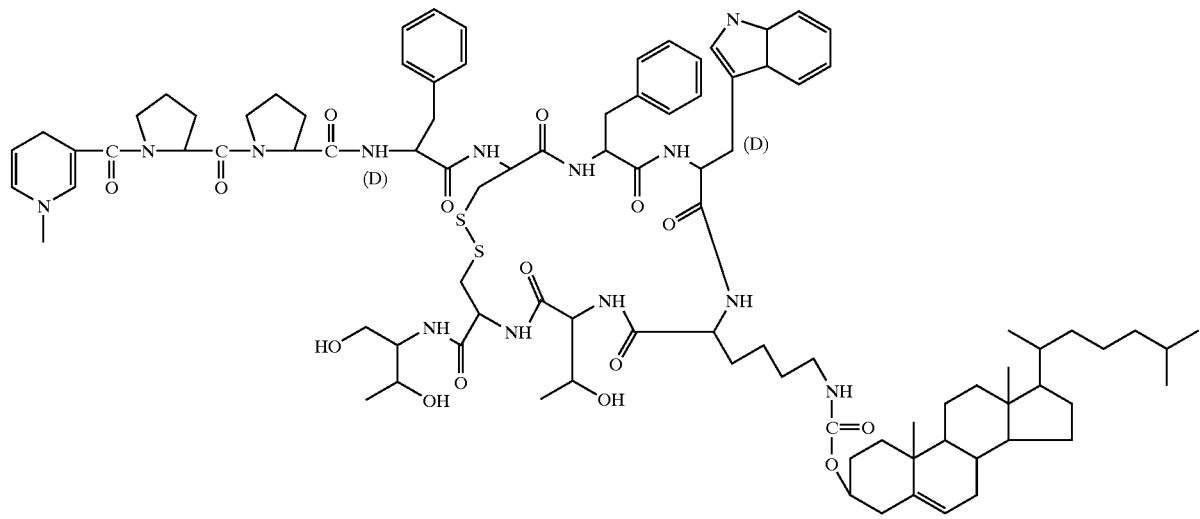
19. A pharmaceutical composition comprising a compound as claimed in claim 1 or claim 9 and a non-toxic, pharmaceutically acceptable carrier therefor.
* * * * *

SEQUENCE LISTING

```
<160> NUMBER OF SEQ ID NOS:  65

<210> SEQ ID NO 1
<211> LENGTH: 14
<212> TYPE: PRT
<213> ORGANISM: Unknown
<220> FEATURE:
<221> NAME/KEY: DISULFID
<222> LOCATION: (3)..(14)
<223> OTHER INFORMATION: Cysteine residues at positions 3 and 14 are
      attached by a non-peptidal disulfide bond.
<221> NAME/KEY: NP_BIND
<222> LOCATION: (8)..(9)
<223> OTHER INFORMATION: Tryptophan and lysine residues at positions 8
      and 9 are attached by a non-peptidal bond.
<223> OTHER INFORMATION: Description of Unknown Organism:peptide
      derivative

<400> SEQUENCE: 1
```

Ala Gly Cys Lys Asn Phe Phe Trp Lys Thr Phe Thr Ser Cys
 1               5                   10

<210> SEQ ID NO 2
<211> LENGTH: 8
<212> TYPE: PRT
<213> ORGANISM: Unknown
<220> FEATURE:
<221> NAME/KEY: PEPTIDE
<222> LOCATION: (1)
<223> OTHER INFORMATION: Amino acid 1 is Xaa wherein Xaa = D-Phe.
<221> NAME/KEY: PEPTIDE
<222> LOCATION: (4)
<223> OTHER INFORMATION: Amino acid 4 is Xaa wherein Xaa = D-Trp.
<221> NAME/KEY: PEPTIDE
<222> LOCATION: (8)
<223> OTHER INFORMATION: Amino acid 8 is Xaa wherein Xaa = Thr(ol).
<221> NAME/KEY: DISULFID
<222> LOCATION: (2)..(7)
<223> OTHER INFORMATION: Cysteine residues at positions 2 and 7 are
      attached by a non-peptidal disulfide bond.
<221> NAME/KEY: NP_BIND
<222> LOCATION: (4)..(5)
<223> OTHER INFORMATION: D-tryptophan and lysine residues at positions 4
      and 5 are attached by a non-peptidal bond.
<223> OTHER INFORMATION: Description of Unknown Organism:peptide
      derivative

<400> SEQUENCE: 2

Xaa Cys Phe Xaa Lys Thr Cys Xaa
 1               5

<210> SEQ ID NO 3
<211> LENGTH: 8
<212> TYPE: PRT
<213> ORGANISM: Unknown
<220> FEATURE:
<221> NAME/KEY: PEPTIDE
<222> LOCATION: (1)
<223> OTHER INFORMATION: Amino acid 1 is Xaa wherein Xaa = D beta Nal.
<221> NAME/KEY: PEPTIDE
<222> LOCATION: (4)
<223> OTHER INFORMATION: Amino acid 4 is Xaa wherein Xaa = D-Trp.
<221> NAME/KEY: PEPTIDE
<222> LOCATION: (8)
<223> OTHER INFORMATION: Amino acid 8 is attached by NH2.
<221> NAME/KEY: DISULFID
<222> LOCATION: (2)..(7)
<223> OTHER INFORMATION: Cysteine residues at positions 2 and 7 are
      attached by a non-peptidal disulfide bond.
<221> NAME/KEY: NP_BIND
<222> LOCATION: (4)..(5)
<223> OTHER INFORMATION: D-tryptophan and lysine residues at positions 4
      and 5 are attached by a non-peptidal bond.
<223> OTHER INFORMATION: Description of Unknown Organism:peptide
      derivative

<400> SEQUENCE: 3

Xaa Cys Tyr Xaa Lys Val Cys Thr
 1               5

<210> SEQ ID NO 4
<211> LENGTH: 8
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is Xaa wherein Xaa = D-Phe and is
      attached with a hydrogen bond.
<221> NAME/KEY: PEPTIDE
<222> LOCATION: (2)..(7)
<223> OTHER INFORMATION: Amino acids 2 and 7 are Xaa wherein

```
        Xaa = L-Ala.
<221> NAME/KEY: PEPTIDE
<222> LOCATION: (4)
<223> OTHER INFORMATION: Amino acid 4 is Xaa wherein Xaa = D-Trp.
<221> NAME/KEY: PEPTIDE
<222> LOCATION: (8)
<223> OTHER INFORMATION: Amino acid 8 is Xaa wherein Xaa = Thr(ol).
<221> NAME/KEY: BINDING
<222> LOCATION: (2)..(7)
<223> OTHER INFORMATION: L-alanine residues at positions 2 and 7 are
      linked by a sulfide bond.
<223> OTHER INFORMATION: Description of Unknown Organism:peptide
      derivative

<400> SEQUENCE: 4

Xaa Xaa Phe Xaa Lys Thr Xaa Xaa
  1               5

<210> SEQ ID NO 5
<211> LENGTH: 8
<212> TYPE: PRT
<213> ORGANISM: Unknown
<220> FEATURE:
<221> NAME/KEY: PEPTIDE
<222> LOCATION: (1)
<223> OTHER INFORMATION: Amino acid 1 is Xaa wherein Xaa = D-Phe and is
      attached with a hydrogen bond.
<221> NAME/KEY: PEPTIDE
<222> LOCATION: (2)..(7)
<223> OTHER INFORMATION: Amino acids 2 and 7 are Xaa wherein
      Xaa = L-Ala.
<221> NAME/KEY: PEPTIDE
<222> LOCATION: (4)
<223> OTHER INFORMATION: Amino acid 4 is Xaa wherein Xaa = D-Trp.
<221> NAME/KEY: BINDING
<222> LOCATION: (2)..(7)
<223> OTHER INFORMATION: L-alanine residues at positions 2 and 7 are
      linked by a sulfide bond.
<221> NAME/KEY: BINDING
<222> LOCATION: (8)
<223> OTHER INFORMATION: Amino acid 8 is attached by NH2.
<223> OTHER INFORMATION: Description of Unknown Organism:peptide
      derivative

<400> SEQUENCE: 5

Xaa Xaa Phe Xaa Lys Thr Xaa Thr
  1               5

<210> SEQ ID NO 6
<211> LENGTH: 7
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is Xaa wherein Xaa = D-Phe and is
      attached by a hydrogen bond.
<221> NAME/KEY: DISULFID
<222> LOCATION: (2)..(7)
<223> OTHER INFORMATION: Cysteine residues at positions 2 and 7 are
      linked by a disulfide bond.
<221> NAME/KEY: PEPTIDE
<222> LOCATION: (4)
<223> OTHER INFORMATION: Amino acid 4 is Xaa wherein Xaa = D-Trp.
<221> NAME/KEY: BINDING
<222> LOCATION: (7)
<223> OTHER INFORMATION: Amino acid 7 is attached by a hydroxide bond.
<223> OTHER INFORMATION: Description of Unknown Organism:peptide
      derivative

<400> SEQUENCE: 6

Xaa Cys Phe Xaa Lys Thr Cys
  1               5
```

```
<210> SEQ ID NO 7
<211> LENGTH: 11
<212> TYPE: PRT
<213> ORGANISM: Unknown
<220> FEATURE:
<221> NAME/KEY: PEPTIDE
<222> LOCATION: (3)
<223> OTHER INFORMATION: Amino acid 3 is Xaa wherein Xaa = D-beta-Nal.
<221> NAME/KEY: DISULFID
<222> LOCATION: (4)..(9)
<223> OTHER INFORMATION: Cysteine residues at positions 4 and 9 are
      attached by a non-peptidal disulfide bond.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (11)
<223> OTHER INFORMATION: Amino acid 11 is attached by an oxygen bond.
<223> OTHER INFORMATION: Description of Unknown Organism:peptide
      derivative

<400> SEQUENCE: 7

Pro Pro Xaa Cys Tyr Xaa Lys Val Cys Thr Gly
  1               5                  10

<210> SEQ ID NO 8
<211> LENGTH: 8
<212> TYPE: PRT
<213> ORGANISM: Unknown
<220> FEATURE:
<221> NAME/KEY: PEPTIDE
<222> LOCATION: (1)
<223> OTHER INFORMATION: Amino acid 1 is Xaa wherein Xaa = D-Phe.
<221> NAME/KEY: DISULFID
<222> LOCATION: (2)..(7)
<223> OTHER INFORMATION: Cysteine residues at positions 2 and 7 are
      attached by a non-peptidal disulfide bond.
<221> NAME/KEY: PEPTIDE
<222> LOCATION: (4)
<223> OTHER INFORMATION: Amino acid 4 is Xaa wherein Xaa = D-Trp.
<221> NAME/KEY: BINDING
<222> LOCATION: (5)
<223> OTHER INFORMATION: Amino acid 5 is attached by Boc.
<221> NAME/KEY: PEPTIDE
<222> LOCATION: (8)
<223> OTHER INFORMATION: Amino acid 8 is Xaa wherein Xaa = Thr(ol).
<223> OTHER INFORMATION: Description of Unknown Organism:peptide
      derivative

<400> SEQUENCE: 8

Xaa Cys Phe Xaa Lys Thr Cys Xaa
  1               5

<210> SEQ ID NO 9
<211> LENGTH: 10
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Nic.
<221> NAME/KEY: PEPTIDE
<222> LOCATION: (3)
<223> OTHER INFORMATION: Amino acid 3 is Xaa wherein Xaa = D-Phe.
<221> NAME/KEY: DISULFID
<222> LOCATION: (4)..(9)
<223> OTHER INFORMATION: Cysteine residues at positions 4 and 9 are
      attached by a non-peptidal disulfide bond.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by Boc.
```

```
<221> NAME/KEY: PEPTIDE
<222> LOCATION: (10)
<223> OTHER INFORMATION: Amino acid 10 is Xaa wherein Xaa = Thr(ol).
<223> OTHER INFORMATION: Description of Unknown Organism:peptide
      derivative

<400> SEQUENCE: 9

Pro Pro Xaa Cys Phe Xaa Lys Thr Cys Xaa
 1               5                  10

<210> SEQ ID NO 10
<211> LENGTH: 10
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Nic.
<221> NAME/KEY: PEPTIDE
<222> LOCATION: (3)
<223> OTHER INFORMATION: Amino acid 3 is Xaa wherein Xaa = D-Phe.
<221> NAME/KEY: DISULFID
<222> LOCATION: (4)..(9)
<223> OTHER INFORMATION: Cysteine residues at positions 4 and 9 are
      attached by a non-peptidal disulfide bond.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by C(O)O-chol.
<221> NAME/KEY: NP_BIND
<222> LOCATION: (10)
<223> OTHER INFORMATION: Amino acid 10 is Xaa wherein Xaa = Thr(ol).
<223> OTHER INFORMATION: Description of Unknown Organism:peptide
      derivative

<400> SEQUENCE: 10

Pro Pro Xaa Cys Phe Xaa Lys Thr Cys Xaa
 1               5                  10

<210> SEQ ID NO 11
<211> LENGTH: 10
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached with Trig.
<221> NAME/KEY: PEPTIDE
<222> LOCATION: (3)
<223> OTHER INFORMATION: Amino acid 3 is Xaa wherein Xaa = D-Phe.
<221> NAME/KEY: DISULFID
<222> LOCATION: (4)..(9)
<223> OTHER INFORMATION: Cysteine residues at positions 4 and 9 are
      attached by a non-peptidal disulfide bond.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by a bond with
      C(O)O-chol.
<221> NAME/KEY: PEPTIDE
<222> LOCATION: (10)
<223> OTHER INFORMATION: Amino acid 10 is Xaa wherein Xaa = Thr(ol).
<223> OTHER INFORMATION: Description of Unknown Organism:peptide
      derivative

<400> SEQUENCE: 11

Pro Pro Xaa Cys Phe Xaa Lys Thr Cys Xaa
 1               5                  10
```

```
<210> SEQ ID NO 12
<211> LENGTH: 10
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached with Dhtr.
<221> NAME/KEY: PEPTIDE
<222> LOCATION: (3)
<223> OTHER INFORMATION: Amino acid 3 is Xaa wherein Xaa = D-Phe.
<221> NAME/KEY: DISULFID
<222> LOCATION: (4)..(9)
<223> OTHER INFORMATION: Cysteine residues at positions 4 and 9 are
      attached by a non-peptidal disulfide bond.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by C(O)O-chol.
<221> NAME/KEY: PEPTIDE
<222> LOCATION: (10)
<223> OTHER INFORMATION: Amino acid 10 is Xaa wherein Xaa = Thr(ol).
<223> OTHER INFORMATION: Description of Unknown Organism:peptide
      derivative

<400> SEQUENCE: 12

Pro Pro Xaa Cys Phe Xaa Lys Thr Cys Xaa
 1               5                  10

<210> SEQ ID NO 13
<211> LENGTH: 10
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached with Trig.
<221> NAME/KEY: PEPTIDE
<222> LOCATION: (3)
<223> OTHER INFORMATION: Amino acid 3 is Xaa wherein Xaa = D-Phe.
<221> NAME/KEY: DISULFID
<222> LOCATION: (4)..(9)
<223> OTHER INFORMATION: Cysteine residues at positions 4 and 9 are
      attached by a non-peptidal disulfide bond.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by C(O)O-chol.
<221> NAME/KEY: PEPTIDE
<222> LOCATION: (10)
<223> OTHER INFORMATION: Amino acid 10 is Xaa wherein Xaa = Thr(ol).
<223> OTHER INFORMATION: Description of Unknown Organism:peptide
      derivative

<400> SEQUENCE: 13

Ala Ala Xaa Cys Phe Xaa Lys Thr Cys Xaa
 1               5                  10

<210> SEQ ID NO 14
<211> LENGTH: 10
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Dhtr.
<221> NAME/KEY: PEPTIDE
<222> LOCATION: (3)
<223> OTHER INFORMATION: Amino acid 3 is Xaa wherein Xaa = D-Phe.
<221> NAME/KEY: DISULFID
<222> LOCATION: (4)..(9)
```

```
<223> OTHER INFORMATION: Cysteine residues at positions 4 and 9 are
      attached by a non-peptidal disulfide bond.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by C(O)O-chol.
<221> NAME/KEY: PEPTIDE
<222> LOCATION: (10)
<223> OTHER INFORMATION: Amino acid 10 is Xaa wherein Xaa = Thr(ol).
<223> OTHER INFORMATION: Description of Unknown Organism:peptide
      derivative

<400> SEQUENCE: 14

Ala Ala Xaa Cys Phe Xaa Lys Thr Cys Xaa
 1               5                  10

<210> SEQ ID NO 15
<211> LENGTH: 10
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached with Trig.
<221> NAME/KEY: PEPTIDE
<222> LOCATION: (3)
<223> OTHER INFORMATION: Amino acid 3 is Xaa wherein Xaa = D-Phe.
<221> NAME/KEY: DISULFID
<222> LOCATION: (4)..(9)
<223> OTHER INFORMATION: Cysteine residues at positions 4 and 9 are
      attached by a non-peptidal disulfide bond.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by
      C(O)O-CH2-CH2-adamantane.
<221> NAME/KEY: PEPTIDE
<222> LOCATION: (10)
<223> OTHER INFORMATION: Amino acid 10 is Xaa wherein Xaa = Thr(ol).
<223> OTHER INFORMATION: Description of Unknown Organism:peptide
      derivative

<400> SEQUENCE: 15

Pro Pro Xaa Cys Phe Xaa Lys Thr Cys Xaa
 1               5                  10

<210> SEQ ID NO 16
<211> LENGTH: 10
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Dhtr.
<221> NAME/KEY: PEPTIDE
<222> LOCATION: (3)
<223> OTHER INFORMATION: Amino acid 3 is Xaa wherein Xaa = D-Phe.
<221> NAME/KEY: DISULFID
<222> LOCATION: (4)..(9)
<223> OTHER INFORMATION: Cysteine residues at positions 4 and 9 are
      attached by a non-peptidal disulfide bond.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by
      C(O)O-CH2-CH2-adamantane.
<221> NAME/KEY: PEPTIDE
<222> LOCATION: (10)
<223> OTHER INFORMATION: Amino acid 10 is Xaa wherein Xaa = Thr(ol).
```

```
<223> OTHER INFORMATION: Description of Unknown Organism:peptide
      derivative

<400> SEQUENCE: 16

Pro Pro Xaa Cys Phe Xaa Lys Thr Cys Xaa
 1               5                  10

<210> SEQ ID NO 17
<211> LENGTH: 8
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is Xaa wherein Xaa = D-Phe and is
      attached by a hydrogen bond.
<221> NAME/KEY: BINDING
<222> LOCATION: (2)..(7)
<223> OTHER INFORMATION: Amino acids 2 and 7 are Xaa wherein Xaa = L-Ala
      and are linked by a sulfide bond.
<221> NAME/KEY: PEPTIDE
<222> LOCATION: (4)
<223> OTHER INFORMATION: Amino acid 4 is Xaa wherein Xaa = D-Trp.
<221> NAME/KEY: BINDING
<222> LOCATION: (5)
<223> OTHER INFORMATION: Amino acid 5 is attached by Boc.
<221> NAME/KEY: PEPTIDE
<222> LOCATION: (8)
<223> OTHER INFORMATION: Amino acid 8 is Xaa wherein Xaa = Thr(ol).
<223> OTHER INFORMATION: Description of Unknown Organism:peptide
      derivative

<400> SEQUENCE: 17

Xaa Xaa Phe Xaa Lys Thr Xaa Xaa
 1               5

<210> SEQ ID NO 18
<211> LENGTH: 10
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Nic.
<221> NAME/KEY: PEPTIDE
<222> LOCATION: (3)
<223> OTHER INFORMATION: Amino acid 3 is Xaa wherein Xaa = D-Phe.
<221> NAME/KEY: BINDING
<222> LOCATION: (4)..(9)
<223> OTHER INFORMATION: Amino acids 4 and 9 are Xaa wherein Xaa - L-Ala
      and are linked by a sulfide bond.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by Boc.
<221> NAME/KEY: PEPTIDE
<222> LOCATION: (10)
<223> OTHER INFORMATION: Amino acid 10 is Xaa wherein Xaa = Thr(ol).
<223> OTHER INFORMATION: Description of Unknown Organism:peptide
      derivative

<400> SEQUENCE: 18

Pro Pro Xaa Xaa Phe Xaa Lys Thr Xaa Xaa
 1               5                  10

<210> SEQ ID NO 19
<211> LENGTH: 10
<212> TYPE: PRT
<213> ORGANISM: Unknown
<220> FEATURE:
<221> NAME/KEY: BINDING
```

```
<222> LOCATION: (1)
<223> OTHER INFORMATION: Amino acid 1 is attached by Nic.
<221> NAME/KEY: PEPTIDE
<222> LOCATION: (3)
<223> OTHER INFORMATION: Amino acid 3 is Xaa wherein Xaa = D-Phe.
<221> NAME/KEY: BINDING
<222> LOCATION: (4)..(9)
<223> OTHER INFORMATION: Amino acids 4 and 9 are Xaa wherein Xaa = L-Ala
      and are linked by a sulfide bond.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by C(O)O-chol.
<221> NAME/KEY: PEPTIDE
<222> LOCATION: (10)
<223> OTHER INFORMATION: Amino acid 10 is Xaa wherein Xaa = Thr(ol).
<223> OTHER INFORMATION: Description of Unknown Organism:peptide
      derivative

<400> SEQUENCE: 19

Pro Pro Xaa Xaa Phe Xaa Lys Thr Xaa Xaa
 1               5                  10

<210> SEQ ID NO 20
<211> LENGTH: 10
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Trig.
<221> NAME/KEY: PEPTIDE
<222> LOCATION: (3)
<223> OTHER INFORMATION: Amino acid 3 is Xaa wherein Xaa = D-Phe.
<221> NAME/KEY: BINDING
<222> LOCATION: (4)..(9)
<223> OTHER INFORMATION: Amino acids 4 and 9 are Xaa wherein Xaa = L-Ala
      and are linked by a sulfide bond.
<221> NAME/KEY: PEPTIDE
<222> LOCATION: (6)
<223> OTHER INFORMATION: Amino acid 6 is Xaa awherein Xaa = D-Trp.
<221> NAME/KEY: BINDING
<222> LOCATION: (7)
<223> OTHER INFORMATION: Amino acid 7 is attached by C(O)O-chol.
<221> NAME/KEY: PEPTIDE
<222> LOCATION: (10)
<223> OTHER INFORMATION: Amino acid 10 is Xaa wherein Xaa = Thr(ol).
<223> OTHER INFORMATION: Description of Unknown Organism:peptide
      derivative

<400> SEQUENCE: 20

Pro Pro Xaa Xaa Phe Xaa Lys Thr Xaa Xaa
 1               5                  10

<210> SEQ ID NO 21
<211> LENGTH: 10
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Dhtr.
<221> NAME/KEY: PEPTIDE
<222> LOCATION: (3)
<223> OTHER INFORMATION: Amino acid 3 is Xaa wherein Xaa = D-Phe.
<221> NAME/KEY: BINDING
<222> LOCATION: (4)..(9)
<223> OTHER INFORMATION: Amino acids 4 and 9 are Xaa wherein Xaa = L-Ala
      and are linked by a sulfide bond.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
```

```
<222> LOCATION: (7)
<223> OTHER INFORMATION: Amino acid 7 is attached by C(O)O-chol.
<221> NAME/KEY: PEPTIDE
<222> LOCATION: (10)
<223> OTHER INFORMATION: Amino acid 10 is Xaa wherein Xaa = Thr(ol).
<223> OTHER INFORMATION: Description of Unknown Organism:peptide
      derivative

<400> SEQUENCE: 21

Pro Pro Xaa Ala Phe Xaa Lys Thr Ala Xaa
  1               5                  10

<210> SEQ ID NO 22
<211> LENGTH: 8
<212> TYPE: PRT
<213> ORGANISM: Unknown
<220> FEATURE:
<221> NAME/KEY: PEPTIDE
<222> LOCATION: (1)
<223> OTHER INFORMATION: Amino acid 1 is Xaa wherein Xaa = D beta Nal.
<221> NAME/KEY: PEPTIDE
<222> LOCATION: (4)
<223> OTHER INFORMATION: Amino acid 4 is Xaa wherein Xaa = D-Trp.
<221> NAME/KEY: BINDING
<222> LOCATION: (5)
<223> OTHER INFORMATION: Amino acid 5 is attached by Boc.
<221> NAME/KEY: PEPTIDE
<222> LOCATION: (8)
<223> OTHER INFORMATION: Amino acid 8 is attached by NH2.
<221> NAME/KEY: DISULFID
<222> LOCATION: (2)..(7)
<223> OTHER INFORMATION: Cysteine residues at positions 2 and 7 are
      attached by a non-peptidal disulfide bond.
<223> OTHER INFORMATION: Description of Unknown Organism:peptide
      derivative

<400> SEQUENCE: 22

Xaa Cys Tyr Xaa Lys Val Cys Thr
  1               5

<210> SEQ ID NO 23
<211> LENGTH: 10
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Nic.
<221> NAME/KEY: PEPTIDE
<222> LOCATION: (3)
<223> OTHER INFORMATION: Amino acid 3 is Xaa wherein Xaa = D beta Nal.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by Boc.
<221> NAME/KEY: BINDING
<222> LOCATION: (10)
<223> OTHER INFORMATION: Amino acid 10 is atached by NH2.
<221> NAME/KEY: DISULFID
<222> LOCATION: (4)..(9)
<223> OTHER INFORMATION: Cysteine residues at positions 4 and 9 are
      attached by a non-peptidal disulfide bond.
<223> OTHER INFORMATION: Description of Unknown Organism:peptide
      derivative

<400> SEQUENCE: 23

Pro Pro Xaa Cys Tyr Xaa Lys Val Cys Thr
  1               5                  10

<210> SEQ ID NO 24
<211> LENGTH: 10
```

```
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Nic.
<221> NAME/KEY: PEPTIDE
<222> LOCATION: (3)
<223> OTHER INFORMATION: Amino acid 3 is Xaa wherein Xaa = D beta Nal.
<221> NAME/KEY: PEPTIDE
<222> LOCATION: (6)
<223> OTHER INFORMATION: Amino acid 6 is Xaa wherein xaa = D-Trp.
<221> NAME/KEY: PEPTIDE
<222> LOCATION: (7)
<223> OTHER INFORMATION: Amino acid 7 is attached by C(O)O-chol.
<221> NAME/KEY: BINDING
<222> LOCATION: (10)
<223> OTHER INFORMATION: Amino acid 10 is attached by NH2.
<221> NAME/KEY: DISULFID
<222> LOCATION: (4)..(9)
<223> OTHER INFORMATION: Cysteine residues at positions 4 and 9 are
      attached by a non-peptidal disulfide bond.
<223> OTHER INFORMATION: Description of Unknown Organism:peptide
      derivative

<400> SEQUENCE: 24

Pro Pro Xaa Cys Tyr Xaa Lys Val Cys Thr
 1               5                  10

<210> SEQ ID NO 25
<211> LENGTH: 10
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Trig.
<221> NAME/KEY: PEPTIDE
<222> LOCATION: (3)
<223> OTHER INFORMATION: Amino acid 3 is Xaa wherein Xaa = D beta Nal.
<221> NAME/KEY: PEPTIDE
<222> LOCATION: (6)
<223> OTHER INFORMATION: Amino acid 6 is Xaa wherein xaa = D-Trp.
<221> NAME/KEY: BINDING
<222> LOCATION: (7)
<223> OTHER INFORMATION: Amino acid 7 is attached by C(O)O-chol.
<221> NAME/KEY: BINDING
<222> LOCATION: (10)
<223> OTHER INFORMATION: Amino acid 10 is attached by NH2.
<221> NAME/KEY: DISULFID
<222> LOCATION: (4)..(9)
<223> OTHER INFORMATION: Cysteine residues at positions 4 and 9 are
      attached by a non-peptidal disulfide bond.
<223> OTHER INFORMATION: Description of Unknown Organism:peptide
      derivative

<400> SEQUENCE: 25

Pro Pro Xaa Cys Tyr Xaa Lys Val Cys Thr
 1               5                  10

<210> SEQ ID NO 26
<211> LENGTH: 10
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Dhtr.
<221> NAME/KEY: PEPTIDE
<222> LOCATION: (3)
<223> OTHER INFORMATION: Amino acid 3 is Xaa wherein Xaa = D beta Nal.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
```

```
<222> LOCATION: (7)
<223> OTHER INFORMATION: Amino acid 7 is attached by C(O)O-chol.
<221> NAME/KEY: BINDING
<222> LOCATION: (10)
<223> OTHER INFORMATION: Amino acid 10 is attached by NH2.
<221> NAME/KEY: DISULFID
<222> LOCATION: (4)..(9)
<223> OTHER INFORMATION: Cysteine residues at positions 4 and 9 are
      attached by a non-peptidal disulfide bond.
<223> OTHER INFORMATION: Description of Unknown Organism:peptide
      derivative

<400> SEQUENCE: 26

Pro Pro Xaa Cys Tyr Xaa Lys Val Cys Thr
 1               5                  10

<210> SEQ ID NO 27
<211> LENGTH: 8
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by a hydrogen bond.
<221> NAME/KEY: PEPTIDE
<222> LOCATION: (1)
<223> OTHER INFORMATION: Amino acid 1 is Xaa wherein Xaa = D-Phe.
<221> NAME/KEY: BINDING
<222> LOCATION: (2)..(7)
<223> OTHER INFORMATION: Amino acids 2 and 7 are Xaa wherein Xaa = L-Ala
      and are linked by a sulfide bond.
<221> NAME/KEY: PEPTIDE
<222> LOCATION: (4)
<223> OTHER INFORMATION: Amino acid 4 is Xaa wherein Xaa = D-Trp.
<221> NAME/KEY: BINDING
<222> LOCATION: (8)
<223> OTHER INFORMATION: Amino acid 8 is attached by NH2.
<223> OTHER INFORMATION: Description of Unknown Organism:peptide
      derivative

<400> SEQUENCE: 27

Xaa Xaa Phe Xaa Lys Thr Xaa Thr
 1               5

<210> SEQ ID NO 28
<211> LENGTH: 10
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Nic.
<221> NAME/KEY: PEPTIDE
<222> LOCATION: (3)
<223> OTHER INFORMATION: Amino acid 3 is Xaa wherein Xaa = D-Phe.
<221> NAME/KEY: BINDING
<222> LOCATION: (4)..(9)
<223> OTHER INFORMATION: Amino acids 4 and 9 are Xaa wherein Xaa = L-Ala
      and are linked by a sulfide bond.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by Boc.
<221> NAME/KEY: BINDING
<222> LOCATION: (10)
<223> OTHER INFORMATION: Amino acid 10 is attached by NH2.
<223> OTHER INFORMATION: Description of Unknown Organism:peptide
      derivative

<400> SEQUENCE: 28

Pro Pro Xaa Xaa Phe Xaa Lys Thr Xaa Thr
 1               5                  10
```

<210> SEQ ID NO 29
<211> LENGTH: 10
<212> TYPE: PRT
<213> ORGANISM: Unknown
<220> FEATURE:
<221> NAME/KEY: PEPTIDE
<222> LOCATION: (1)
<223> OTHER INFORMATION: Amino acid 1 is attached by Nic.
<221> NAME/KEY: PEPTIDE
<222> LOCATION: (3)
<223> OTHER INFORMATION: Amino acid 3 is Xaa wherein Xaa = D-Phe.
<221> NAME/KEY: BINDING
<222> LOCATION: (4)..(9)
<223> OTHER INFORMATION: Amino acids 4 and 9 are Xaa wherein Xaa = L-Ala and are linked by a sulfide bond.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by C(O)O-chol.
<221> NAME/KEY: BINDING
<222> LOCATION: (10)
<223> OTHER INFORMATION: Amino acid 10 is attached by NH2.
<223> OTHER INFORMATION: Description of Unknown Organism:peptide derivative

<400> SEQUENCE: 29

Pro Pro Xaa Xaa Phe Xaa Lys Thr Xaa Thr
 1               5                  10

<210> SEQ ID NO 30
<211> LENGTH: 10
<212> TYPE: PRT
<213> ORGANISM: Unknown
<220> FEATURE:
<221> NAME/KEY: PEPTIDE
<222> LOCATION: (1)
<223> OTHER INFORMATION: Amino acid 1 is attached by Trig.
<221> NAME/KEY: PEPTIDE
<222> LOCATION: (3)
<223> OTHER INFORMATION: Amino acid 3 is Xaa wherein Xaa = D-Phe.
<221> NAME/KEY: BINDING
<222> LOCATION: (4)..(9)
<223> OTHER INFORMATION: Amino acids 4 and 9 are Xaa wherein Xaa = L-Ala and are linked by a sulfide bond.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by C(O)O-chol.
<221> NAME/KEY: BINDING
<222> LOCATION: (10)
<223> OTHER INFORMATION: Amino acid 10 is attached by NH2.
<223> OTHER INFORMATION: Description of Unknown Organism:peptide derivative

<400> SEQUENCE: 30

Pro Pro Xaa Xaa Phe Xaa Lys Thr Xaa Thr
 1               5                  10

<210> SEQ ID NO 31
<211> LENGTH: 10
<212> TYPE: PRT
<213> ORGANISM: Unknown
<220> FEATURE:
<221> NAME/KEY: PEPTIDE
<222> LOCATION: (1)
<223> OTHER INFORMATION: Amino acid 1 is attached by Dhtr.
<221> NAME/KEY: PEPTIDE
<222> LOCATION: (3)
<223> OTHER INFORMATION: Amino acid 3 is Xaa wherein Xaa = D-Phe.

```
<221> NAME/KEY: BINDING
<222> LOCATION: (4)..(9)
<223> OTHER INFORMATION: Amino acids 4 and 9 are Xaa wherein Xaa = L-Ala
      and are linked by a sulfide bond.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by C(O)O-chol.
<221> NAME/KEY: BINDING
<222> LOCATION: (10)
<223> OTHER INFORMATION: Amino acid 10 is attached by NH2.
<223> OTHER INFORMATION: Description of Unknown Organism:peptide
      derivative

<400> SEQUENCE: 31

Pro Pro Xaa Xaa Phe Xaa Lys Thr Xaa Thr
 1               5                  10

<210> SEQ ID NO 32
<211> LENGTH: 9
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Nic.
<221> NAME/KEY: PEPTIDE
<222> LOCATION: (3)
<223> OTHER INFORMATION: Amino acid 3 is Xaa wherein Xaa = D-Phe.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by Boc.
<221> NAME/KEY: BINDING
<222> LOCATION: (9)
<223> OTHER INFORMATION: Amino acid 9 is attached by NHCH(CHOH)CH3-
      thr-O-contienyl.
<221> NAME/KEY: DISULFID
<222> LOCATION: (4)..(9)
<223> OTHER INFORMATION: Cysteine residues at positions 4 and 9 are
      attached by a non-peptidal disulfide bond.
<223> OTHER INFORMATION: Description of Unknown Organism:peptide
      derivative

<400> SEQUENCE: 32

Pro Pro Xaa Cys Phe Xaa Lys Thr Cys
 1               5

<210> SEQ ID NO 33
<211> LENGTH: 9
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Trig.
<221> NAME/KEY: PEPTIDE
<222> LOCATION: (3)
<223> OTHER INFORMATION: Amino acid 3 is Xaa wherein Xaa = D-Phe.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by Boc.
<221> NAME/KEY: BINDING
<222> LOCATION: (9)
<223> OTHER INFORMATION: Amino acid 9 is attached by NHCH(CHOH)CH3-
      thr-O-contienyl.
<221> NAME/KEY: DISULFID
<222> LOCATION: (4)..(9)
```

```
<223> OTHER INFORMATION: Cysteine residues at positions 4 and 9 are
      attached by a non-peptidal disulfide bond.
<223> OTHER INFORMATION: Description of Unknown Organism:peptide
      derivative

<400> SEQUENCE: 33

Pro Pro Xaa Cys Phe Xaa Lys Thr Cys
  1               5

<210> SEQ ID NO 34
<211> LENGTH: 9
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Dhtr.
<221> NAME/KEY: PEPTIDE
<222> LOCATION: (3)
<223> OTHER INFORMATION: Amino acid 3 is Xaa wherein Xaa = D-Phe.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by Boc.
<221> NAME/KEY: BINDING
<222> LOCATION: (9)
<223> OTHER INFORMATION: Amino acid 9 is attached by NHCH(CHOH)CH3-
      thr-O-contienyl.
<221> NAME/KEY: DISULFID
<222> LOCATION: (4)..(9)
<223> OTHER INFORMATION: Cysteine residues at positions 4 and 9 are
      attached by a non-peptidal disulfide bond.
<223> OTHER INFORMATION: Description of Unknown Organism:peptide
      derivative

<400> SEQUENCE: 34

Pro Pro Xaa Cys Phe Xaa Lys Thr Cys
  1               5

<210> SEQ ID NO 35
<211> LENGTH: 9
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Nic.
<221> NAME/KEY: PEPTIDE
<222> LOCATION: (3)
<223> OTHER INFORMATION: Amino acid 3 is Xaa wherein Xaa = D-Phe.
<221> NAME/KEY: BINDING
<222> LOCATION: (4)..(9)
<223> OTHER INFORMATION: Amino acids 4 and 9 are Xaa wherein Xaa = L-Ala
      and are linked by a sulfide bond.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by Boc.
<221> NAME/KEY: BINDING
<222> LOCATION: (9)
<223> OTHER INFORMATION: Amino acid 9 is attached by
      NHCH(CHOH)CH3-thr-O-contienyl.
<223> OTHER INFORMATION: Description of Unknown Organism:peptide
      derivative

<400> SEQUENCE: 35

Pro Pro Xaa Xaa Phe Xaa Lys Thr Xaa
  1               5
```

```
<210> SEQ ID NO 36
<211> LENGTH: 9
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Trig.
<221> NAME/KEY: PEPTIDE
<222> LOCATION: (3)
<223> OTHER INFORMATION: Amino acid 3 is Xaa wherein Xaa = D-Phe.
<221> NAME/KEY: BINDING
<222> LOCATION: (4)..(9)
<223> OTHER INFORMATION: Amino acids 4 and 9 are Xaa wherein Xaa = L-Ala
      and are linked by a sulfide bond.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by Boc.
<221> NAME/KEY: BINDING
<222> LOCATION: (9)
<223> OTHER INFORMATION: Amino acid 9 is attached by
      NHCH(CHOH)CH3-thr-O-contienyl.
<223> OTHER INFORMATION: Description of Unknown Organism:peptide
      derivative

<400> SEQUENCE: 36

Pro Pro Xaa Xaa Phe Xaa Lys Thr Xaa
 1               5

<210> SEQ ID NO 37
<211> LENGTH: 9
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Dhtr.
<221> NAME/KEY: PEPTIDE
<222> LOCATION: (3)
<223> OTHER INFORMATION: Amino acid 3 is Xaa wherein Xaa = D-Phe.
<221> NAME/KEY: BINDING
<222> LOCATION: (4)..(9)
<223> OTHER INFORMATION: Amino acids 4 and 9 are Xaa wherein Xaa = L-Ala
      and are linked by a sulfide bond.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by Boc.
<221> NAME/KEY: BINDING
<222> LOCATION: (9)
<223> OTHER INFORMATION: Amino acid 9 is attached by
      NHCH(CHOH)CH3-thr-O-contienyl.
<223> OTHER INFORMATION: Description of Unknown Organism:peptide
      derivative

<400> SEQUENCE: 37

Pro Pro Xaa Xaa Phe Xaa Lys Thr Xaa
 1               5

<210> SEQ ID NO 38
<211> LENGTH: 7
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by D-beta-Nal.
<221> NAME/KEY: PEPTIDE
<222> LOCATION: (3)
<223> OTHER INFORMATION: Amino acid 3 is Xaa wherein Xaa = D-Trp.
```

```
<221> NAME/KEY: BINDING
<222> LOCATION: (7)
<223> OTHER INFORMATION: Amino acid 7 is attached by a hydroxide bond.
<221> NAME/KEY: DISULFID
<222> LOCATION: (1)..(6)
<223> OTHER INFORMATION: Cysteine residues at positions 1 and 6 are
      attached by a non-peptidal disulfide bond.
<223> OTHER INFORMATION: Description of Unknown Organism:peptide
      derivative

<400> SEQUENCE: 38

Cys Tyr Xaa Lys Val Cys Thr
 1               5

<210> SEQ ID NO 39
<211> LENGTH: 7
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by D-beta-Nal.
<221> NAME/KEY: PEPTIDE
<222> LOCATION: (3)
<223> OTHER INFORMATION: Amino acid 3 is Xaa wherein Xaa = D-Trp.
<221> NAME/KEY: BINDING
<222> LOCATION: (4)
<223> OTHER INFORMATION: Amino acid 4 is attached by Boc.
<221> NAME/KEY: BINDING
<222> LOCATION: (7)
<223> OTHER INFORMATION: Amino acid 7 is attached by a hydroxide bond.
<221> NAME/KEY: DISULFID
<222> LOCATION: (1)..(6)
<223> OTHER INFORMATION: Cysteine residues at positions 1 and 6 are
      attached by a non-peptidal disulfide bond.
<223> OTHER INFORMATION: Description of Unknown Organism:peptide
      derivative

<400> SEQUENCE: 39

Cys Tyr Xaa Lys Val Cys Thr
 1               5

<210> SEQ ID NO 40
<211> LENGTH: 7
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by D-beta-Nal.
<221> NAME/KEY: PEPTIDE
<222> LOCATION: (3)
<223> OTHER INFORMATION: Amino acid 3 is Xaa wherein Xaa = D-Trp.
<221> NAME/KEY: BINDING
<222> LOCATION: (4)
<223> OTHER INFORMATION: Amino acid 4 is attached by Boc.
<221> NAME/KEY: BINDING
<222> LOCATION: (7)
<223> OTHER INFORMATION: Amino acid 7 is attached by a hydroxide bond.
<221> NAME/KEY: DISULFID
<222> LOCATION: (1)..(6)
<223> OTHER INFORMATION: Cysteine residues at positions 1 and 6 are
      attached by a non-peptidal disulfide bond.
<223> OTHER INFORMATION: Description of Unknown Organism:peptide
      derivative

<400> SEQUENCE: 40

Cys Tyr Xaa Lys Val Cys Thr
 1               5

<210> SEQ ID NO 41
<211> LENGTH: 7
<212> TYPE: PRT
```

```
<213> ORGANISM: Unknown
<220> FEATURE:
<221> NAME/KEY: BINDING
<222> LOCATION: (1)
<223> OTHER INFORMATION: Amino acid 1 is attached by Fmoc-D-beta-Nal.
<221> NAME/KEY: PEPTIDE
<222> LOCATION: (3)
<223> OTHER INFORMATION: Amino acid 3 is Xaa wherein Xaa = D-Trp.
<221> NAME/KEY: BINDING
<222> LOCATION: (4)
<223> OTHER INFORMATION: Amino acid 4 is attached by Boc.
<221> NAME/KEY: BINDING
<222> LOCATION: (7)
<223> OTHER INFORMATION: Amino acid 7 is attached by a hydroxide bond.
<221> NAME/KEY: DISULFID
<222> LOCATION: (1)..(6)
<223> OTHER INFORMATION: Cysteine residues at positions 1 and 6 are
      attached by a non-peptidal disulfide bond.
<223> OTHER INFORMATION: Description of Unknown Organism:peptide
      derivative

<400> SEQUENCE: 41

Cys Tyr Xaa Lys Val Cys Thr
 1               5

<210> SEQ ID NO 42
<211> LENGTH: 8
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by D-beta-Nal.
<221> NAME/KEY: PEPTIDE
<222> LOCATION: (3)
<223> OTHER INFORMATION: Amino acid 3 is Xaa wherein Xaa = D-Trp.
<221> NAME/KEY: BINDING
<222> LOCATION: (4)
<223> OTHER INFORMATION: Amino acid 4 is attached by Boc.
<221> NAME/KEY: BINDING
<222> LOCATION: (8)
<223> OTHER INFORMATION: Amino acid 8 is attached by O-chol.
<221> NAME/KEY: DISULFID
<222> LOCATION: (1)..(6)
<223> OTHER INFORMATION: Cysteine residues at positions 1 and 6 are
      attached by a non-peptidal disulfide bond.
<223> OTHER INFORMATION: Description of Unknown Organism:peptide
      derivative

<400> SEQUENCE: 42

Cys Tyr Xaa Lys Val Cys Thr Gly
 1               5

<210> SEQ ID NO 43
<211> LENGTH: 11
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Nic.
<221> NAME/KEY: PEPTIDE
<222> LOCATION: (3)
<223> OTHER INFORMATION: Amino acid 3 is Xaa wherein Xaa = D-beta-Nal.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by Boc.
<221> NAME/KEY: BINDING
<222> LOCATION: (11)
<223> OTHER INFORMATION: Amino acid 11 is attached by O-chol.
<221> NAME/KEY: DISULFID
<222> LOCATION: (4)..(9)
```

```
<223> OTHER INFORMATION: Cysteine residues at positions 4 and 9 are
      attached by a non-peptidal disulfide bond.
<223> OTHER INFORMATION: Description of Unknown Organism:peptide
      derivative

<400> SEQUENCE: 43

Pro Pro Xaa Cys Tyr Xaa Lys Val Cys Thr Gly
  1               5                  10

<210> SEQ ID NO 44
<211> LENGTH: 11
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Trig.
<221> NAME/KEY: PEPTIDE
<222> LOCATION: (3)
<223> OTHER INFORMATION: Amino acid 3 is Xaa wherein Xaa = D-beta-Nal.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by Boc.
<221> NAME/KEY: BINDING
<222> LOCATION: (11)
<223> OTHER INFORMATION: Amino acid 11 is attached by O-chol.
<221> NAME/KEY: DISULFID
<222> LOCATION: (4)..(9)
<223> OTHER INFORMATION: Cysteine residues at positions 4 and 9 are
      attached by a non-peptidal disulfide bond.
<223> OTHER INFORMATION: Description of Unknown Organism:peptide
      derivative

<400> SEQUENCE: 44

Pro Pro Xaa Cys Tyr Xaa Lys Val Cys Thr Gly
  1               5                  10

<210> SEQ ID NO 45
<211> LENGTH: 11
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Dhtr.
<221> NAME/KEY: PEPTIDE
<222> LOCATION: (3)
<223> OTHER INFORMATION: Amino acid 3 is Xaa wherein Xaa = D-beta-Nal.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by Boc.
<221> NAME/KEY: BINDING
<222> LOCATION: (11)
<223> OTHER INFORMATION: Amino acid 11 is attached by O-chol.
<221> NAME/KEY: DISULFID
<222> LOCATION: (4)..(9)
<223> OTHER INFORMATION: Cysteine residues at positions 4 and 9 are
      attached by a non-peptidal disulfide bond.
<223> OTHER INFORMATION: Description of Unknown Organism:peptide
      derivative

<400> SEQUENCE: 45

Pro Pro Xaa Cys Tyr Xaa Lys Val Cys Thr Gly
  1               5                  10

<210> SEQ ID NO 46
<211> LENGTH: 7
```

```
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is Xaa wherein Xaa = D-Phe and is
      attached by a hydrogen bond.
<221> NAME/KEY: BINDING
<222> LOCATION: (2)..(7)
<223> OTHER INFORMATION: Amino acids 2 and 7 are Xaa wherein Xaa = L-Ala
      and are linked by a sulfide bond.
<221> NAME/KEY: PEPTIDE
<222> LOCATION: (4)
<223> OTHER INFORMATION: Amino acid 4 is Xaa wherein Xaa = D-Trp.
<221> NAME/KEY: BINDING
<222> LOCATION: (7)
<223> OTHER INFORMATION: Amino acid 7 is attached by a hydroxide bond.
<223> OTHER INFORMATION: Description of Unknown Organism:peptide
      derivative

<400> SEQUENCE: 46

Xaa Xaa Phe Xaa Lys Thr Xaa
 1               5

<210> SEQ ID NO 47
<211> LENGTH: 7
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is Xaa wherein Xaa = D-Phe and is
      attached by a hydrogen bond.
<221> NAME/KEY: BINDING
<222> LOCATION: (2)..(7)
<223> OTHER INFORMATION: Amino acids 2 and 7 are Xaa wherein Xaa = L-Ala
      and are linked by a sulfide bond.
<221> NAME/KEY: PEPTIDE
<222> LOCATION: (4)
<223> OTHER INFORMATION: Amino acid 4 is Xaa wherein Xaa = D-Trp.
<221> NAME/KEY: BINDING
<222> LOCATION: (5)
<223> OTHER INFORMATION: Amino acid 5 is attached by Boc.
<221> NAME/KEY: BINDING
<222> LOCATION: (7)
<223> OTHER INFORMATION: Amino acid 7 is attached by a hydroxide bond.
<223> OTHER INFORMATION: Description of Unknown Organism:peptide
      derivative

<400> SEQUENCE: 47

Xaa Xaa Phe Xaa Lys Thr Xaa
 1               5

<210> SEQ ID NO 48
<211> LENGTH: 7
<212> TYPE: PRT
<213> ORGANISM: Unknown
<220> FEATURE:
<221> NAME/KEY: PEPTIDE
<222> LOCATION: (1)
<223> OTHER INFORMATION: Amino acid 1 is Xaa wherein Xaa = D-Phe and
      is attached by Fmoc.
<221> NAME/KEY: BINDING
<222> LOCATION: (2)..(7)
<223> OTHER INFORMATION: Amino acids 2 and 7 are Xaa wherein Xaa = L-Ala
      and are linked by a sulfide bond.
<221> NAME/KEY: PEPTIDE
<222> LOCATION: (4)
<223> OTHER INFORMATION: Amino acid 4 is Xaa wherein Xaa = D-Trp.
<221> NAME/KEY: BINDING
<222> LOCATION: (5)
<223> OTHER INFORMATION: Amino acid 5 is attached by Boc.
<221> NAME/KEY: BINDING
<222> LOCATION: (7)
<223> OTHER INFORMATION: Amino acid 7 is attached by a hydroxide bond.
```

<223> OTHER INFORMATION: Description of Unknown Organism:peptide
      derivative

<400> SEQUENCE: 48

Xaa Xaa Phe Xaa Lys Thr Xaa
 1               5

<210> SEQ ID NO 49
<211> LENGTH: 7
<212> TYPE: PRT
<213> ORGANISM: Unknown
<220> FEATURE:
<221> NAME/KEY: PEPTIDE
<222> LOCATION: (1)
<223> OTHER INFORMATION: Amino acid 1 is Xaa wherein Xaa = D-Phe and
      is attached by Fmoc.
<221> NAME/KEY: BINDING
<222> LOCATION: (2)..(7)
<223> OTHER INFORMATION: Amino acids 2 and 7 are Xaa wherein Xaa = L-Ala
      and are linked by a sulfide bond.
<221> NAME/KEY: PEPTIDE
<222> LOCATION: (4)
<223> OTHER INFORMATION: Amino acid 4 is Xaa wherein Xaa = D-Trp.
<221> NAME/KEY: BINDING
<222> LOCATION: (5)
<223> OTHER INFORMATION: Amino acid 5 is attached by Boc.
<221> NAME/KEY: BINDING
<222> LOCATION: (7)
<223> OTHER INFORMATION: Amino acid 7 is attached by a hydroxide bond.
<223> OTHER INFORMATION: Description of Unknown Organism:peptide
      derivative

<400> SEQUENCE: 49

Xaa Xaa Phe Xaa Lys Thr Xaa
 1               5

<210> SEQ ID NO 50
<211> LENGTH: 9
<212> TYPE: PRT
<213> ORGANISM: Unknown
<220> FEATURE:
<221> NAME/KEY: PEPTIDE
<222> LOCATION: (1)
<223> OTHER INFORMATION: Amino acid 1 is Xaa wherein Xaa = D-Phe.
<221> NAME/KEY: BINDING
<222> LOCATION: (2)..(7)
<223> OTHER INFORMATION: Amino acids 2 and 7 are Xaa wherein Xaa = L-Ala
      and are linked by a sulfide bond.
<221> NAME/KEY: PEPTIDE
<222> LOCATION: (4)
<223> OTHER INFORMATION: Amino acid 4 is Xaa wherein Xaa = D-Trp.
<221> NAME/KEY: BINDING
<222> LOCATION: (5)
<223> OTHER INFORMATION: Amino acid 5 is attached by Boc.
<221> NAME/KEY: BINDING
<222> LOCATION: (9)
<223> OTHER INFORMATION: Amino acid 9 is attached by O-chol.
<223> OTHER INFORMATION: Description of Unknown Organism:peptide
      derivative

<400> SEQUENCE: 50

Xaa Xaa Phe Xaa Lys Thr Xaa Thr Gly
 1               5

<210> SEQ ID NO 51
<211> LENGTH: 11
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Nic.
<221> NAME/KEY: PEPTIDE

```
<222> LOCATION: (3)
<223> OTHER INFORMATION: Amino acid 3 is Xaa wherein Xaa = D-Phe.
<221> NAME/KEY: BINDING
<222> LOCATION: (4)..(9)
<223> OTHER INFORMATION: Amino acids 4 and 9 are Xaa wherein Xaa = L-Ala
      and are linked by a sulfide bond.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by Boc.
<221> NAME/KEY: BINDING
<222> LOCATION: (11)
<223> OTHER INFORMATION: Amino acid 11 is attached by O-chol.
<223> OTHER INFORMATION: Description of Unknown Organism:peptide
      derivative

<400> SEQUENCE: 51

Pro Pro Xaa Xaa Phe Xaa Lys Thr Xaa Thr Gly
 1               5                   10

<210> SEQ ID NO 52
<211> LENGTH: 11
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Trig.
<221> NAME/KEY: PEPTIDE
<222> LOCATION: (3)
<223> OTHER INFORMATION: Amino acid 3 is Xaa wherein Xaa = D-Phe.
<221> NAME/KEY: BINDING
<222> LOCATION: (4)..(9)
<223> OTHER INFORMATION: Amino acids 4 and 9 are Xaa wherein Xaa = L-Ala
      and are linked by a sulfide bond.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by Boc.
<221> NAME/KEY: BINDING
<222> LOCATION: (11)
<223> OTHER INFORMATION: Amino acid 11 is attached by O-chol.
<223> OTHER INFORMATION: Description of Unknown Organism:peptide
      derivative

<400> SEQUENCE: 52

Pro Pro Xaa Xaa Phe Xaa Lys Thr Xaa Thr Gly
 1               5                   10

<210> SEQ ID NO 53
<211> LENGTH: 11
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Dhtr.
<221> NAME/KEY: PEPTIDE
<222> LOCATION: (3)
<223> OTHER INFORMATION: Amino acid 3 is Xaa wherein Xaa = D-Phe.
<221> NAME/KEY: BINDING
<222> LOCATION: (4)..(9)
<223> OTHER INFORMATION: Amino acids 4 and 9 are Xaa wherein Xaa = L-Ala
      and are linked by a sulfide bond.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by Boc.
<221> NAME/KEY: BINDING
```

```
<222> LOCATION: (11)
<223> OTHER INFORMATION: Amino acid 11 is attached by O-chol.
<223> OTHER INFORMATION: Description of Unknown Organism:peptide
      derivative

<400> SEQUENCE: 53

Pro Pro Xaa Xaa Phe Xaa Lys Thr Xaa Thr Gly
  1               5                  10

<210> SEQ ID NO 54
<211> LENGTH: 7
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is Xaa wherein Xaa = D-Phe
      and is attached by a hydrogen bond.
<221> NAME/KEY: PEPTIDE
<222> LOCATION: (4)
<223> OTHER INFORMATION: Amino acid 4 is Xaa wherein Xaa = D-Trp.
<221> NAME/KEY: BINDING
<222> LOCATION: (5)
<223> OTHER INFORMATION: Amino acid 5 is attached by Boc.
<221> NAME/KEY: BINDING
<222> LOCATION: (7)
<223> OTHER INFORMATION: Amino acid 7 is attached by a hydroxide bond.
<221> NAME/KEY: DISULFID
<222> LOCATION: (2)..(7)
<223> OTHER INFORMATION: Cysteine residues at positions 2 and 7 are
      attached to a non-peptidal disulfide bond.
<223> OTHER INFORMATION: Description of Unknown Organism:peptide
      derivative

<400> SEQUENCE: 54

Xaa Cys Phe Xaa Lys Thr Cys
  1               5

<210> SEQ ID NO 55
<211> LENGTH: 7
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is Xaa wherein Xaa = D-Phe
      and is attached by Fmoc.
<221> NAME/KEY: PEPTIDE
<222> LOCATION: (4)
<223> OTHER INFORMATION: Amino acid 4 is Xaa wherein Xaa = D-Trp.
<221> NAME/KEY: BINDING
<222> LOCATION: (5)
<223> OTHER INFORMATION: Amino acid 5 is attached by Boc.
<221> NAME/KEY: BINDING
<222> LOCATION: (7)
<223> OTHER INFORMATION: Amino acid 7 is attached by O-chol
<221> NAME/KEY: DISULFID
<222> LOCATION: (2)..(7)
<223> OTHER INFORMATION: Cysteine residues at positions 2 and 7 are
      attached to a non-peptidal disulfide bond.
<223> OTHER INFORMATION: Description of Unknown Organism:peptide
      derivative

<400> SEQUENCE: 55

Xaa Cys Phe Xaa Lys Thr Cys
  1               5

<210> SEQ ID NO 56
<211> LENGTH: 9
<212> TYPE: PRT
<213> ORGANISM: Unknown
<220> FEATURE:
<221> NAME/KEY: BINDING
```

```
<222> LOCATION: (1)
<223> OTHER INFORMATION: Amino acid 1 is attached by Nic.
<221> NAME/KEY: PEPTIDE
<222> LOCATION: (3)
<223> OTHER INFORMATION: Amino acid 3 is Xaa wherein Xaa = D-Phe.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by Boc.
<221> NAME/KEY: BINDING
<222> LOCATION: (9)
<223> OTHER INFORMATION: Amino acid 9 is attached by O-chol.
<221> NAME/KEY: DISULFID
<222> LOCATION: (4)..(9)
<223> OTHER INFORMATION: Cysteine residues at positions 4 and 9 are
      attached to a non-peptidal disulfide bond.
<223> OTHER INFORMATION: Description of Unknown Organism:peptide
      derivative

<400> SEQUENCE: 56

Pro Pro Xaa Cys Phe Xaa Lys Thr Cys
  1               5

<210> SEQ ID NO 57
<211> LENGTH: 9
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Trig.
<221> NAME/KEY: PEPTIDE
<222> LOCATION: (3)
<223> OTHER INFORMATION: Amino acid 3 is Xaa wherein Xaa = D-Phe.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by Boc.
<221> NAME/KEY: BINDING
<222> LOCATION: (9)
<223> OTHER INFORMATION: Amino acid 9 is attached by O-chol.
<221> NAME/KEY: DISULFID
<222> LOCATION: (4)..(9)
<223> OTHER INFORMATION: Cysteine residues at positions 4 and 9 are
      attached to a non-peptidal disulfide bond.
<223> OTHER INFORMATION: Description of Unknown Organism:peptide
      derivative

<400> SEQUENCE: 57

Pro Pro Xaa Cys Phe Xaa Lys Thr Cys
  1               5

<210> SEQ ID NO 58
<211> LENGTH: 9
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Dhtr.
<221> NAME/KEY: PEPTIDE
<222> LOCATION: (3)
<223> OTHER INFORMATION: Amino acid 3 is Xaa wherein Xaa = D-Phe.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by Boc.
<221> NAME/KEY: BINDING
<222> LOCATION: (9)
```

```
<223> OTHER INFORMATION: Amino acid 9 is attached by O-chol.
<221> NAME/KEY: DISULFID
<222> LOCATION: (4)..(9)
<223> OTHER INFORMATION: Cysteine residues at positions 4 and 9 are
      attached to a non-peptidal disulfide bond.
<223> OTHER INFORMATION: Description of Unknown Organism:peptide
      derivative

<400> SEQUENCE: 58

Pro Pro Xaa Cys Phe Xaa Lys Thr Cys
  1               5

<210> SEQ ID NO 59
<211> LENGTH: 7
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Trig.
<221> NAME/KEY: BINDING
<222> LOCATION: (7)
<223> OTHER INFORMATION: Amino acid 7 is attached by a hydroxide bond.
<221> NAME/KEY: DISULFID
<222> LOCATION: (3)..(6)
<223> OTHER INFORMATION: Cysteine residues at positions 3 and 6 are
      attached by a non-peptidal disulfide bond.
<223> OTHER INFORMATION: Description of Unknown Organism:peptide
      derivative

<400> SEQUENCE: 59

Gly Gly Cys Gly Gly Cys Gly
  1               5

<210> SEQ ID NO 60
<211> LENGTH: 7
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Nic.
<221> NAME/KEY: BINDING
<222> LOCATION: (7)
<223> OTHER INFORMATION: Amino acid 7 is attached by a hydroxide bond.
<221> NAME/KEY: DISULFIDE
<222> LOCATION: (3)..(6)
<223> OTHER INFORMATION: Cysteine residues at positions 3 and 6 are
      attached by a non-peptidal disulfide bond.
<223> OTHER INFORMATION: Description of Unknown Organism:peptide
      derivative

<400> SEQUENCE: 60

Gly Gly Cys Gly Gly Cys Gly
  1               5

<210> SEQ ID NO 61
<211> LENGTH: 9
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Nic.
<221> NAME/KEY: PEPTIDE
<222> LOCATION: (3)
<223> OTHER INFORMATION: Amino acid 3 is Xaa wherein Xaa = D-Phe.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (7)
<223> OTHER INFORMATION: Amino acid 7 is attached by Boc.
```

```
<221> NAME/KEY: BINDING
<222> LOCATION: (9)
<223> OTHER INFORMATION: Amino acid 9 is attached by Thr(ol).
<221> NAME/KEY: DISULFID
<222> LOCATION: (4)..(9)
<223> OTHER INFORMATION: Amino acid 9 is attached by Thr(ol).
<223> OTHER INFORMATION: Description of Unknown Organism:peptide
      derivative

<400> SEQUENCE: 61

Pro Pro Xaa Cys Phe Xaa Lys Thr Cys
  1               5

<210> SEQ ID NO 62
<211> LENGTH: 7
<212> TYPE: PRT
<213> ORGANISM: Unknown
<220> FEATURE:
<221> NAME/KEY: BINDING
<222> LOCATION: (1)
<223> OTHER INFORMATION: Amino acid 1 is attached by Nic.
<221> NAME/KEY: BINDING
<222> LOCATION: (7)
<223> OTHER INFORMATION: Amino acid 7 is attached by a hydroxide bond.
<221> NAME/KEY: DISULFID
<222> LOCATION: (3)..(6)
<223> OTHER INFORMATION: Cysteine residues at positions 3 and 6 are
      attached by a non-peptidal disulfide bond.
<223> OTHER INFORMATION: Description of Unknown Organism:peptide
      derivative

<400> SEQUENCE: 62

Gly Gly Cys Gly Gly Cys Gly
  1               5

<210> SEQ ID NO 63
<211> LENGTH: 11
<212> TYPE: PRT
<213> ORGANISM: Unknown
<220> FEATURE:
<221> NAME/KEY: PEPTIDE
<222> LOCATION: (3)
<223> OTHER INFORMATION: Amino acid 3 is Xaa wherein Xaa = D-beta-Nal.
<221> NAME/KEY: DISULFID
<222> LOCATION: (4)..(9)
<223> OTHER INFORMATION: Cysteine residues at positions 4 and 9 are
      attached by a non-peptidal disulfide bond.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (11)
<223> OTHER INFORMATION: Amino acid 11 is attached by an oxygen bond.
<223> OTHER INFORMATION: Description of Unknown Organism:peptide
      derivative

<400> SEQUENCE: 63

Ala Ala Xaa Cys Tyr Xaa Lys Val Cys Thr Gly
  1               5                  10

<210> SEQ ID NO 64
<211> LENGTH: 11
<212> TYPE: PRT
<213> ORGANISM: Unknown
<220> FEATURE:
<221> NAME/KEY: PEPTIDE
<222> LOCATION: (3)
<223> OTHER INFORMATION: Amino acid 3 is Xaa wherein Xaa = D-beta-Nal.
<221> NAME/KEY: DISULFID
<222> LOCATION: (4)..(9)
<223> OTHER INFORMATION: Cysteine residues at positions 4 and 9 are
      attached by a non-peptidal disulfide bond.
<221> NAME/KEY: PEPTIDE
```

```
<222> LOCATION: (6)
<223> OTHER INFORMATION: Amino acid 6 is Xaa wherein Xaa = D-Trp.
<221> NAME/KEY: BINDING
<222> LOCATION: (11)
<223> OTHER INFORMATION: Amino acid 11 is attached by an oxygen bond.
<223> OTHER INFORMATION: Description of Unknown Organism:peptide
      derivative

<400> SEQUENCE: 64

Pro Ala Xaa Cys Tyr Xaa Lys Val Cys Thr Gly
 1               5                  10

<210> SEQ ID NO 65
<211> LENGTH: 11
<212> TYPE: PRT
<213> ORGANISM: Unknown
<220> FEATURE:
<221> NAME/KEY: PEPTIDE
<222> LOCATION: (3)
<223> OTHER INFORMATION: Amino acid 3 is Xaa wherein Xaa = D-beta-Nal.
<221> NAME/KEY: DISULFID
<222> LOCATION: (4)..(9)
<223> OTHER INFORMATION: Cysteine residues at positions 4 and 9 are
      attached by a non-peptidal disulfide bond.
<221> NAME/KEY: PEPTIDE
<222> LOCATION: (6)
<223> OTHER INFORMATION: Amino acid 6 is Xaa wherein Xaa = D-Trp.
<221> NAME/KEY: BINDING
<222> LOCATION: (11)
<223> OTHER INFORMATION: Amino acid 11 is attached by an oxygen bond.
<223> OTHER INFORMATION: Description of Unknown Organism:peptide
      derivative

<400> SEQUENCE: 65

Ala Pro Xaa Cys Tyr Xaa Lys Val Cys Thr Gly
 1               5                  10
```